United States Patent
Broomer et al.

(10) Patent No.: US 9,309,565 B2
(45) Date of Patent: Apr. 12, 2016

(54) KARYOTYPING ASSAY

(75) Inventors: Adam Broomer, Carlsbad, CA (US);
Kelly Li, San Jose, CA (US); Andreas R. Tobler, Fremont, CA (US); Caifu Chen, Palo Alto, CA (US); David N. Keys, Jr., Oakland, CA (US)

(73) Assignee: Life Technologies Corporation, Carlsbad, CA (US)

( * ) Notice: Subject to any disclaimer, the term of this patent is extended or adjusted under 35 U.S.C. 154(b) by 998 days.

(21) Appl. No.: 13/107,786

(22) Filed: May 13, 2011

(65) Prior Publication Data

US 2011/0281755 A1    Nov. 17, 2011

Related U.S. Application Data

(60) Provisional application No. 61/334,658, filed on May 14, 2010.

(51) Int. Cl.
*C12Q 1/68* (2006.01)

(52) U.S. Cl.
CPC ..................... *C12Q 1/6844* (2013.01)

(58) Field of Classification Search
CPC .................................................. C12Q 1/6844
See application file for complete search history.

(56) References Cited

U.S. PATENT DOCUMENTS

| 4,257,774 A | 3/1981 | Richardson et al. |
|---|---|---|
| 4,683,195 A | 7/1987 | Mullis et al. |
| 4,683,202 A | 7/1987 | Mullis |
| 4,889,818 A | 12/1989 | Gelfand et al. |
| 4,965,188 A | 10/1990 | Mullis et al. |
| 5,035,996 A | 7/1991 | Hartley |
| 5,079,352 A | 1/1992 | Gelfand et al. |
| 5,210,015 A | 5/1993 | Gelfand et al. |
| 5,436,134 A | 7/1995 | Haugland et al. |
| 5,487,972 A | 1/1996 | Gelfand et al. |
| 5,538,848 A | 7/1996 | Livak et al. |
| 5,618,711 A | 4/1997 | Gelfand et al. |
| 5,658,751 A | 8/1997 | Yue et al. |
| 5,677,152 A | 10/1997 | Birch et al. |
| 5,723,591 A | 3/1998 | Livak et al. |
| 5,773,258 A | 6/1998 | Birch et al. |
| 5,789,224 A | 8/1998 | Gelfand et al. |
| 5,801,155 A | 9/1998 | Kutyavin et al. |
| 5,804,375 A | 9/1998 | Gelfand et al. |
| 5,854,033 A | 12/1998 | Lizardi |
| 5,876,930 A | 3/1999 | Livak et al. |
| 5,994,056 A | 11/1999 | Higuchi |

(Continued)

FOREIGN PATENT DOCUMENTS

| EP | 0070685 A2 | 1/1983 |
|---|---|---|
| WO | WO-2006/081222 | 8/2006 |

(Continued)

OTHER PUBLICATIONS

Kim et al., Disruption of Neurexin 1 Associated with Autism Spectrum Disorder, The American Journal of Human Genetics 82, 199-207, Jan. 2008.*

(Continued)

*Primary Examiner* — Reza Ghafoorian
(74) *Attorney, Agent, or Firm* — Life Technologies Corporation

(57) ABSTRACT

This disclosure relates to methods and kits for karyotyping in which chromosomes are interrogated by amplifying loci that are not within copy number variable regions thereof.

21 Claims, 8 Drawing Sheets

(56) References Cited

U.S. PATENT DOCUMENTS

| | | | |
|---|---|---|---|
| 6,030,787 | A | 2/2000 | Livak et al. |
| 6,084,102 | A | 7/2000 | Kutyavin et al. |
| 6,127,155 | A | 10/2000 | Gelfand et al. |
| 6,171,785 | B1 | 1/2001 | Higuchi |
| 6,180,349 | B1* | 1/2001 | Ginzinger et al. ............ 435/6.11 |
| 6,214,979 | B1 | 4/2001 | Gelfand et al. |
| 6,258,569 | B1 | 7/2001 | Livak et al. |
| 6,814,934 | B1 | 11/2004 | Higuchi |
| 6,821,727 | B1 | 11/2004 | Livak et al. |
| RE39,007 | E | 3/2006 | Dattagupta et al. |
| 7,141,377 | B2 | 11/2006 | Gelfand et al. |
| 7,387,887 | B2 | 6/2008 | Wittwer et al. |
| 7,445,900 | B2 | 11/2008 | Gelfand et al. |
| 2004/0265897 | A1 | 12/2004 | Lizardi |
| 2008/0118925 | A1* | 5/2008 | Cuppens et al. ................... 435/6 |
| 2008/0286783 | A1* | 11/2008 | Hosono et al. ..................... 435/6 |
| 2009/0197254 | A1 | 8/2009 | Lee |
| 2010/0317916 | A1 | 12/2010 | Scott et al. |

FOREIGN PATENT DOCUMENTS

| | | |
|---|---|---|
| WO | WO-2006/087574 | 8/2006 |
| WO | 2006/128195 | 11/2006 |
| WO | 2009/153568 | 12/2009 |

OTHER PUBLICATIONS

Berggren et al., Detecting Homozygous Deletions in the CDKN2A(p16INK4a)/ARF(p14ARF) Gene in Urinary Bladder Cancer Using Real-Time Quantitative PCR, Clinical Cancer Research, vol. 9, 235-242, Jan. 2003.*

Schmittgen et al., Analyzing real-time PCR data by the comparative CT method, Nature Protocols, vol. 3, No. 6, 2008, 1101-1108.*

Bubner, B. et al., "Use of Real-Time PCR for Determining Copy Number and Zygosity in Transgenic Plants", *Plant Cell Reports*, vol. 23(5), 2004, 263-271.

Gouas, L. et al., "Gene Dosage Methods as Diagnostic Tools for the Identification of Chromosome Abnormalities", *Pathologie-Biologie*, vol. 56(6), 2008, 345-353.

Jeon, J. P. et al., "A Comprehensive Profile of DNA Copy Number Variations in a Korean Population: Identification of Copy Number Invariant Regions Among Koreans", *Experimental & Molecular Medicine*, vol. 41(9), 2009, 618-628.

International Search Report along with the Written Opinion for International Application No. PCT/US2011/036516 date mailed Feb. 9, 2012.

*Nature Genetics*, vol. 39, Jul. 2007, pp. S1-S54, entire issue.

Afonina, I. A., "Minor Groove Binder-Conjugated DNA Probes for Quantitative DNA Detection by Hybridization-Triggered Fluorescence", *BioTechniques*, vol. 32, 2002, 940-949.

Baner, Johan, "Signal Amplification of PadlockProbes by Rolling Circle Replication," *Nucleic Acids Research*, vol. 26, No. 22 1998, 5073-5078.

Barany, "Genetic Disease Detection and DNA Amplification Using Cloned Thermostable Ligase," *Proceedings of the National Academy of Sciences (PNAS)* vol. 88, Issue 1 1991, 189-193.

Cardullo, Richard A., "Detection of Nucleic Acid Hybridization by Non Radiative Fluorescence Resonance Energy Transfer", *Proceedings of the National Academy of Sciences (PNAS)*, vol. 85 1988, 8790-8794.

Cikos, Stefan, "Transformation of Real-Time PCR Fluorescence Data to Target Gene Quantity," *Analytical Biochemistry*, vol. 384, 2009, 1-10.

Feuk, Lars, "Structural Variation in the Human Genome," *Nature Reviews Genetics*, vol. 7(2), 2006, 85-97.

Fiandaca, Mark J., "Self-Reporting PNA/DNA Primers for PCR Analysis", *Genome Research*, vol. 11, 2001, 609-613.

Freeman, Jennifer L., "Copy Number Variation: New Insights in Genome Diversity", *Genome Research*, vol. 16, 2006, 949-961.

French, D.J., "HyBeacon™ Probes: A New Tool for DNA Sequence Detection and Allele Discrimination", *Molecular and Cellular Probes*, vol. 15, 2001, 363-374.

Jain, S. C., "Stereochemistry of Actinomycin Binding to DNA", *Journal of Molecular Biology*, vol. 68, 1972, 1-20.

Johnston, Brian H., "Characterization of the Photoreaction Between DNA and Aminomethyl-Trimethylpsoralen Using Absorption and Fluorescence Spectroscopy", *Photochemistry and Photobiology*, vol. 33, 1981, 785-791.

Kapuscinski, Jan, "Interactions of 4', 6-diamidine-2-phenylindole with Synthetic Polynucleotides", *Nucl. Acids Res.*, vol. 6, No. 11, 1979, 3519-3534.

Li, Qingge, "A New Class of Homogeneous Nucleic Acid Probes Based on Specific Displacement Hybridization," *Nucleic Acids Research*, vol. 30, No. 2, e5, 2002, 1-9.

Little, Michael C., "Strand Displacement Amplification and Homogeneous Real-Time Detection Incorporated in a Second-Generation DNA Probe System, BDProbeTecET", *Clinical Chemistry*, vol. 45(6), 1999, 777-784.

Livak, Kenneth J., "Analysis of Relative Gene Expression Data Using Real-Time Quantitative PCR and the 2-ΔΔcT Method," *Methods*, vol. 25, 2001, 402-408.

Lizardi, "Mutation Detection and Single-Molecule Counting Using Isothermal Rolling-Circle Amplification", *Nature Genetics* vol. 19, Jul. 1998, 225-232.

Morrison, Larry E., "Solution-phase detection of polynucleotides using interacting fluorescent labels and competitive hybridization", *Anal. Biochem.*, vol. 183, No. 2, 1989, 231-244.

Nazarenko, Irina A., "A Closed Tube Format for Amplification and Detection of DNA Based on Energy Transfer", *Nucleic Acids Research*, vol. 25, No. 12, Oxford University Press, 1997, 2516-2521.

Nazarenko, Irina, "Multiplex quantitative PCR using self quenched primers labeled with a single fluorophore", *Nucleic Acids Research*, vol. 30, No. 9, e37 2002, 1-7.

Nutiu, Razvan, "Tripartite Molecular Beacon," *Nucleic Acids Research*, vol. 30, e94, 2002, 1-9.

Oser, Andreas, "Nonradioactive Assay of DNA Hybridization by DNA-Template-Mediated Formation of a Ternary Tblll Complex in Pure Liquid Phase", *Angewandte Chemie International Edition in English*, vol. 29, No. 10, 1990, 1167-1169.

Pellestor, Franck, "The Peptide Nucleic Acids (PNAs), Powerful Tools for Molecular Genetics and Cytogenetics", *European Journal of Human Genetics*, vol. 12, 2004, 694-700.

Redon, Richard, "Global Variation in Copy Number in the Human Genome", *Nature*, vol. 444, 2006, 444-454.

Searle, Mark S., "Sequence-specific interaction of Hoescht 33258 with the minor grooVe of an adenine-tract DNA duplex studied in solution by 1H NMR spectroscopy", *Nucl. Acids. Res.*, vol. 18, No. 13, Oxford University Press, 1990, 3753-3762.

Sharp, Andrew J., "Structural Variation of the Human Genome," *Annual Rev. Genomics & Human Genet.*, vol. 7, 2006, 407-442.

Singh, S., "LNA (locked nucleic acids): synthesis and high-affinity nucleic acid recognition", *Chem. Commun.*, vol. 4, 1998, 455-456.

Speicher, Michael R., "The New Cytogenetics: Blurring the Boundaries with Molecular Biology," *Nature Reviews Genetics*, vol. 6, 2005, 782-792.

Svanvik, Nicke, "Light-Up Probes: Thiazole Orange-Conjugated Peptide Nucleic Acid for Detection of Target Nucleic Acid in Homogeneous Solution", *Analytical Biochemistry* vol. 281, 2000, 26-35.

Todd, Alison V., "DzyNA-PCR: Use of DNAzymes to Detect and Quantify Nucleic Acid Sequences in a Real-Time Fluorescent Format", *Clinical Chemistry*, vol. 46, No. 5, 2000, 625-630.

Trask, Barbara J., "Human Cytogenetics: 46 Chromosomes, 46 Years and Counting," *Nature Reviews Genetics*, vol. 3, 2002, 769-778.

Tyagi, Sanjay, "Molecular Beacons: Probes that Fluoresce upon Hybridization", *Nature Biotechnology*, vol. 14, Mar. 1996, 303-308.

Whitcombe, David, "Detection of PCR products using self-probing amplicons and fluorescence", *Nature Biotechnology*, vol. 17, Aug. 1999, 804-807.

Wu, Dan Y., "The Ligation Amplification Reaction (LAR)-Amplification of Specific DNA Sequences Using Sequential Rounds of Template-Dependent Ligation," *Genomics*, vol. 4, 1989, 560-569.

(56) References Cited

OTHER PUBLICATIONS

EP 11781377.4; Extended European Search Report mailed Mar. 12, 2014.

Jeon, et al., "Copy Number variation at leptin receptor gene locus associated with metabolic traits and the risk of type 2 diabetes mellitus", *BMC Genomics*, vol. 11, No. 426, downloaded from http://www.biomedcentral.com/1471-2164/11/426, 2010, 10 pages.

PCT/US2011/036516; International Preliminary Report on Patentability mailed Nov. 20, 2012.

* cited by examiner

*Chromosome 2*

*Chromosome 3*

*Chromosome 5*

*Chromosome 20*

*Chromosome 20*

*Chromosome 22*

```
                          SEQUENCE LISTING

<160> NUMBER OF SEQ ID NOS: 384

<210> SEQ ID NO 1
<211> LENGTH: 20
<212> TYPE: DNA
<213> ORGANISM: Artificial Sequence
<220> FEATURE:
<223> OTHER INFORMATION: Forward Primer sequence

<400> SEQUENCE: 1
ccagggctgc ctattgactt                                                 20

<210> SEQ ID NO 2
<211> LENGTH: 18
<212> TYPE: DNA
<213> ORGANISM: Artificial Sequence
<220> FEATURE:
<223> OTHER INFORMATION: Reverse Primer sequence

<400> SEQUENCE: 2
gctgatccgg cagacact                                                   18

<210> SEQ ID NO 3
<211> LENGTH: 17
<212> TYPE: DNA
<213> ORGANISM: Artificial Sequence
<220> FEATURE:
<223> OTHER INFORMATION: Forward Primer sequence

<400> SEQUENCE: 3
cccacggcct tcaggat                                                    17

<210> SEQ ID NO 4
<211> LENGTH: 16
<212> TYPE: DNA
<213> ORGANISM: Artificial Sequence
<220> FEATURE:
<223> OTHER INFORMATION: Reverse Primer sequence

<400> SEQUENCE: 4
gggctctgca caccca                                                     16

<210> SEQ ID NO 5
<211> LENGTH: 19
<212> TYPE: DNA
<213> ORGANISM: Artificial Sequence
```

<220> FEATURE:
<223> OTHER INFORMATION: Forward Primer sequence

<400> SEQUENCE: 5
aacccaccag cctgaactg                                              19

<210> SEQ ID NO 6
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 6
tgagctcagt cagtacatca gagat                                       25

<210> SEQ ID NO 7
<211> LENGTH: 21
<212> TYPE: DNA
<213> ORGANISM: Artificial Sequence
<220> FEATURE:
<223> OTHER INFORMATION: Forward Primer sequence

<400> SEQUENCE: 7
cacaatgctg cctgacatca t                                           21

<210> SEQ ID NO 8
<211> LENGTH: 21
<212> TYPE: DNA
<213> ORGANISM: Artificial Sequence
<220> FEATURE:
<223> OTHER INFORMATION: Reverse Primer sequence

<400> SEQUENCE: 8
tgctttgttg gcagctggat a                                           21

<210> SEQ ID NO 9
<211> LENGTH: 26
<212> TYPE: DNA
<213> ORGANISM: Artificial Sequence
<220> FEATURE:
<223> OTHER INFORMATION: Forward Primer sequence

<400> SEQUENCE: 9
tgacagcttt tggctcagaa attaga                                      26

<210> SEQ ID NO 10
<211> LENGTH: 24
<212> TYPE: DNA
<213> ORGANISM: Artificial Sequence
<220> FEATURE:
<223> OTHER INFORMATION: Reverse Primer sequence

<400> SEQUENCE: 10
cctgtcactg ggaggaaatc cata                                        24

<210> SEQ ID NO 11
<211> LENGTH: 22
<212> TYPE: DNA
<213> ORGANISM: Artificial Sequence
<220> FEATURE:
<223> OTHER INFORMATION: Forward Primer sequence

<400> SEQUENCE: 11
cacgatgagg gttgagggaa aa                                          22

-continued

<210> SEQ ID NO 12
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 12
gattcttgag ccagcagctg ta                                            22

<210> SEQ ID NO 13
<211> LENGTH: 21
<212> TYPE: DNA
<213> ORGANISM: Artificial Sequence
<220> FEATURE:
<223> OTHER INFORMATION: Forward Primer sequence

<400> SEQUENCE: 13
gccaggatgc tccatgtagt a                                             21

<210> SEQ ID NO 14
<211> LENGTH: 27
<212> TYPE: DNA
<213> ORGANISM: Artificial Sequence
<220> FEATURE:
<223> OTHER INFORMATION: Reverse Primer sequence

<400> SEQUENCE: 14
aaggattatt ctgacggttc atgttgt                                       27

<210> SEQ ID NO 15
<211> LENGTH: 32
<212> TYPE: DNA
<213> ORGANISM: Artificial Sequence
<220> FEATURE:
<223> OTHER INFORMATION: Forward Primer sequence

<400> SEQUENCE: 15
aggtgaaaaa agtacttatg aggatgatga at                                 32

<210> SEQ ID NO 16
<211> LENGTH: 28
<212> TYPE: DNA
<213> ORGANISM: Artificial Sequence
<220> FEATURE:
<223> OTHER INFORMATION: Reverse Primer sequence

<400> SEQUENCE: 16
ttgatcaaag cttatggctc tatcaact                                      28

<210> SEQ ID NO 17
<211> LENGTH: 29
<212> TYPE: DNA
<213> ORGANISM: Artificial Sequence
<220> FEATURE:
<223> OTHER INFORMATION: Forward Primer sequence

<400> SEQUENCE: 17
aaacaggaga atgaatgaat gaatatgct                                     29

<210> SEQ ID NO 18
<211> LENGTH: 25
<212> TYPE: DNA
<213> ORGANISM: Artificial Sequence
<220> FEATURE:
<223> OTHER INFORMATION: Reverse Primer sequence

```
<400> SEQUENCE: 18
ccatagacag attagcctgc ttctt                                              25

<210> SEQ ID NO 19
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 19
ccatagacag attagcctgc ttctt                                              25

<210> SEQ ID NO 20
<211> LENGTH: 18
<212> TYPE: DNA
<213> ORGANISM: Artificial Sequence
<220> FEATURE:
<223> OTHER INFORMATION: Reverse Primer sequence

<400> SEQUENCE: 20
tgggtttggt gcctcaca                                                      18

<210> SEQ ID NO 21
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 21
tggcatgtga gatgtgttca agaaa                                              25

<210> SEQ ID NO 22
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 22
aaagggtacc actagagagg ca                                                 22

<210> SEQ ID NO 23
<211> LENGTH: 29
<212> TYPE: DNA
<213> ORGANISM: Artificial Sequence
<220> FEATURE:
<223> OTHER INFORMATION: Forward Primer sequence

<400> SEQUENCE: 23
tccctcaagt ttattcagtc tccttatgt                                          29

<210> SEQ ID NO 24
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 24
agagcaagac gtccaaattg aagta                                              25

<210> SEQ ID NO 25
```

```
<211> LENGTH: 28
<212> TYPE: DNA
<213> ORGANISM: Artificial Sequence
<220> FEATURE:
<223> OTHER INFORMATION: Forward Primer sequence

<400> SEQUENCE: 25
catttccaag tacagtaact ccacagta                                          28

<210> SEQ ID NO 26
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 26
cctcagtggt gcaaaaacag tt                                                22

<210> SEQ ID NO 27
<211> LENGTH: 22
<212> TYPE: DNA
<213> ORGANISM: Artificial Sequence
<220> FEATURE:
<223> OTHER INFORMATION: Forward Primer sequence

<400> SEQUENCE: 27
cccaagcacc tgtagcatca tc                                                22

<210> SEQ ID NO 28
<211> LENGTH: 24
<212> TYPE: DNA
<213> ORGANISM: Artificial Sequence
<220> FEATURE:
<223> OTHER INFORMATION: Reverse Primer sequence

<400> SEQUENCE: 28
cctcaaacat ctgccttcat gtgt                                              24

<210> SEQ ID NO 29
<211> LENGTH: 23
<212> TYPE: DNA
<213> ORGANISM: Artificial Sequence
<220> FEATURE:
<223> OTHER INFORMATION: Forward Primer sequence

<400> SEQUENCE: 29
ggaatgttac cacgttgcta agc                                               23

<210> SEQ ID NO 30
<211> LENGTH: 24
<212> TYPE: DNA
<213> ORGANISM: Artificial Sequence
<220> FEATURE:
<223> OTHER INFORMATION: Reverse Primer sequence

<400> SEQUENCE: 30
cagctgtctt catccagttt ctca                                              24

<210> SEQ ID NO 31
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 31
```
tttctgggag ccatctgaat catc                                        24

<210> SEQ ID NO 32
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 32
cagcgaatca aatagcccct ctt                                         23

<210> SEQ ID NO 33
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 33
ggtatgacct ggacacatta agca                                        24

<210> SEQ ID NO 34
<211> LENGTH: 33
<212> TYPE: DNA
<213> ORGANISM: Artificial Sequence
<220> FEATURE:
<223> OTHER INFORMATION: Reverse Primer sequence

<400> SEQUENCE: 34
aggagggaga taaaataat gagaaatgta agc                               33

<210> SEQ ID NO 35
<211> LENGTH: 20
<212> TYPE: DNA
<213> ORGANISM: Artificial Sequence
<220> FEATURE:
<223> OTHER INFORMATION: Forward Primer sequence

<400> SEQUENCE: 35
gcaagccaca ggaagaggaa                                             20

<210> SEQ ID NO 36
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 36
tgtacaattt gacttggtgc cagaa                                       25

<210> SEQ ID NO 37
<211> LENGTH: 20
<212> TYPE: DNA
<213> ORGANISM: Artificial Sequence
<220> FEATURE:
<223> OTHER INFORMATION: Forward Primer sequence

<400> SEQUENCE: 37
gcggaacaag ccagactgaa                                             20

<210> SEQ ID NO 38
<211> LENGTH: 19
<212> TYPE: DNA

```
<213> ORGANISM: Artificial Sequence
<220> FEATURE:
<223> OTHER INFORMATION: Reverse Primer sequence

<400> SEQUENCE: 38
gaggttcgag cgctgttct                                                    19

<210> SEQ ID NO 39
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 39
gttttagaag gaagagggct aggaa                                             25

<210> SEQ ID NO 40
<211> LENGTH: 24
<212> TYPE: DNA
<213> ORGANISM: Artificial Sequence
<220> FEATURE:
<223> OTHER INFORMATION: Reverse Primer sequence

<400> SEQUENCE: 40
agaatgtgca gtcaacactc agaa                                              24

<210> SEQ ID NO 41
<211> LENGTH: 21
<212> TYPE: DNA
<213> ORGANISM: Artificial Sequence
<220> FEATURE:
<223> OTHER INFORMATION: Forward Primer sequence

<400> SEQUENCE: 41
gtataggcag cgacagcact t                                                 21

<210> SEQ ID NO 42
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 42
agatctccac aggactcacc aa                                                22

<210> SEQ ID NO 43
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 43
gaaaaccaaa gcaacaaggt gagt                                              24

<210> SEQ ID NO 44
<211> LENGTH: 24
<212> TYPE: DNA
<213> ORGANISM: Artificial Sequence
<220> FEATURE:
<223> OTHER INFORMATION: Reverse Primer sequence

<400> SEQUENCE: 44
gggagatggg agtaagttcc aaac                                              24
```

<210> SEQ ID NO 45
<211> LENGTH: 19
<212> TYPE: DNA
<213> ORGANISM: Artificial Sequence
<220> FEATURE:
<223> OTHER INFORMATION: Forward Primer sequence

<400> SEQUENCE: 45
gggttgcagg gatggtgta                                           19

<210> SEQ ID NO 46
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 46
tgcattcatt ctgatcttcc acaca                                    25

<210> SEQ ID NO 47
<211> LENGTH: 23
<212> TYPE: DNA
<213> ORGANISM: Artificial Sequence
<220> FEATURE:
<223> OTHER INFORMATION: Forward Primer sequence

<400> SEQUENCE: 47
gggatctgta acttgaccaa ggt                                      23

<210> SEQ ID NO 48
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 48
gcagcacagc aaagtgtttc ag                                       22

<210> SEQ ID NO 49
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 49
gatggtatct cccacaagtc actac                                    25

<210> SEQ ID NO 50
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 50
caatttgcag cacaaggagc ta                                       22

<210> SEQ ID NO 51
<211> LENGTH: 25
<212> TYPE: DNA
<213> ORGANISM: Artificial Sequence
<220> FEATURE:

<223> OTHER INFORMATION: Forward Primer sequence

<400> SEQUENCE: 51
ctgtctgatt gttaagaggg cttgt                                  25

<210> SEQ ID NO 52
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 52
gtcacaactt gttcttggga gtttg                                  25

<210> SEQ ID NO 53
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 53
gatagatggc ctggcagtaa gaac                                   24

<210> SEQ ID NO 54
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 54
gccttctagg gactgacttc aa                                     22

<210> SEQ ID NO 55
<211> LENGTH: 23
<212> TYPE: DNA
<213> ORGANISM: Artificial Sequence
<220> FEATURE:
<223> OTHER INFORMATION: Forward Primer sequence

<400> SEQUENCE: 55
tgaacctttg acaccttccc aaa                                    23

<210> SEQ ID NO 56
<211> LENGTH: 26
<212> TYPE: DNA
<213> ORGANISM: Artificial Sequence
<220> FEATURE:
<223> OTHER INFORMATION: Reverse Primer sequence

<400> SEQUENCE: 56
tgacagcaaa tattaccgaa ggtgat                                 26

<210> SEQ ID NO 57
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 57
gatctcctct tctgtgccta catc                                   24

```
<210> SEQ ID NO 58
<211> LENGTH: 31
<212> TYPE: DNA
<213> ORGANISM: Artificial Sequence
<220> FEATURE:
<223> OTHER INFORMATION: Reverse Primer sequence

<400> SEQUENCE: 58
tgtgatgaca aaaacataaa tgagactgag t                              31

<210> SEQ ID NO 59
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 59
gttctctctg gccgtcaata tctt                                      24

<210> SEQ ID NO 60
<211> LENGTH: 20
<212> TYPE: DNA
<213> ORGANISM: Artificial Sequence
<220> FEATURE:
<223> OTHER INFORMATION: Reverse Primer sequence

<400> SEQUENCE: 60
cacttctgca gaggctggaa                                           20

<210> SEQ ID NO 61
<211> LENGTH: 22
<212> TYPE: DNA
<213> ORGANISM: Artificial Sequence
<220> FEATURE:
<223> OTHER INFORMATION: Forward Primer sequence

<400> SEQUENCE: 61
gggacctggg tttcctgata ct                                        22

<210> SEQ ID NO 62
<211> LENGTH: 21
<212> TYPE: DNA
<213> ORGANISM: Artificial Sequence
<220> FEATURE:
<223> OTHER INFORMATION: Reverse Primer sequence

<400> SEQUENCE: 62
acccagagtc gagtggacaa t                                         21

<210> SEQ ID NO 63
<211> LENGTH: 22
<212> TYPE: DNA
<213> ORGANISM: Artificial Sequence
<220> FEATURE:
<223> OTHER INFORMATION: Forward Primer sequence

<400> SEQUENCE: 63
tggagagaac cccaggcttt at                                        22

<210> SEQ ID NO 64
<211> LENGTH: 28
<212> TYPE: DNA
<213> ORGANISM: Artificial Sequence
<220> FEATURE:
<223> OTHER INFORMATION: Reverse Primer sequence
```

<400> SEQUENCE: 64
ctaaagcaat gtgtgtgatt cataagca                                          28

<210> SEQ ID NO 65
<211> LENGTH: 26
<212> TYPE: DNA
<213> ORGANISM: Artificial Sequence
<220> FEATURE:
<223> OTHER INFORMATION: Forward Primer sequence

<400> SEQUENCE: 65
agatgggatc aagggtaaat cagagt                                            26

<210> SEQ ID NO 66
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 66
gggcacataa acttctctac atcca                                             25

<210> SEQ ID NO 67
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 67
tggccatagc agggaataat ttca                                              24

<210> SEQ ID NO 68
<211> LENGTH: 20
<212> TYPE: DNA
<213> ORGANISM: Artificial Sequence
<220> FEATURE:
<223> OTHER INFORMATION: Reverse Primer sequence

<400> SEQUENCE: 68
accagacaca tgtgcaccaa                                                   20

<210> SEQ ID NO 69
<211> LENGTH: 27
<212> TYPE: DNA
<213> ORGANISM: Artificial Sequence
<220> FEATURE:
<223> OTHER INFORMATION: Forward Primer sequence

<400> SEQUENCE: 69
ggatgggcaa ttttaggtaa tctccaa                                           27

<210> SEQ ID NO 70
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 70
atctcttaag cacctaccct ggt                                               23

<210> SEQ ID NO 71
<211> LENGTH: 19

```
<212> TYPE: DNA
<213> ORGANISM: Artificial Sequence
<220> FEATURE:
<223> OTHER INFORMATION: Forward Primer sequence

<400> SEQUENCE: 71
ccagtgcctt gtgcaggat                                              19

<210> SEQ ID NO 72
<211> LENGTH: 21
<212> TYPE: DNA
<213> ORGANISM: Artificial Sequence
<220> FEATURE:
<223> OTHER INFORMATION: Reverse Primer sequence

<400> SEQUENCE: 72
cctccctgag ctcacaagat t                                           21

<210> SEQ ID NO 73
<211> LENGTH: 36
<212> TYPE: DNA
<213> ORGANISM: Artificial Sequence
<220> FEATURE:
<223> OTHER INFORMATION: Forward Primer sequence

<400> SEQUENCE: 73
aaatagaata tgagacatga gtaaatatgc cctttt                           36

<210> SEQ ID NO 74
<211> LENGTH: 24
<212> TYPE: DNA
<213> ORGANISM: Artificial Sequence
<220> FEATURE:
<223> OTHER INFORMATION: Reverse Primer sequence

<400> SEQUENCE: 74
tcaagttgta gtcagtgcca caaa                                        24

<210> SEQ ID NO 75
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 75
caaaagctac aagccagaga tacga                                       25

<210> SEQ ID NO 76
<211> LENGTH: 26
<212> TYPE: DNA
<213> ORGANISM: Artificial Sequence
<220> FEATURE:
<223> OTHER INFORMATION: Reverse Primer sequence

<400> SEQUENCE: 76
acacatatgt acagagagac caggaa                                      26

<210> SEQ ID NO 77
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 77
```

-continued aagacaatgt gcagcaaaag atagc                                              25

<210> SEQ ID NO 78
<211> LENGTH: 24
<212> TYPE: DNA
<213> ORGANISM: Artificial Sequence
<220> FEATURE:
<223> OTHER INFORMATION: Reverse Primer sequence

<400> SEQUENCE: 78
ggcctcttcc tgtatttgca gttt                                               24

<210> SEQ ID NO 79
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 79
caaattttac ccacacagcc tgaaa                                              25

<210> SEQ ID NO 80
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 80
gcttaagttg tatgtgtgca gagtt                                              25

<210> SEQ ID NO 81
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 81
aaaacaagta gggcactgga agaa                                               24

<210> SEQ ID NO 82
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 82 tgcccttca actgctgatt ctaat                                               25

<210> SEQ ID NO 83
<211> LENGTH: 22
<212> TYPE: DNA
<213> ORGANISM: Artificial Sequence
<220> FEATURE:
<223> OTHER INFORMATION: Forward Primer sequence

<400> SEQUENCE: 83
cattgcagaa ctccagggaa ct                                                 22

<210> SEQ ID NO 84
<211> LENGTH: 18
<212> TYPE: DNA
<213> ORGANISM: Artificial Sequence

```
<220> FEATURE:
<223> OTHER INFORMATION: Reverse Primer sequence

<400> SEQUENCE: 84
ctgtctgcga cgggaaga                                              18

<210> SEQ ID NO 85
<211> LENGTH: 16
<212> TYPE: DNA
<213> ORGANISM: Artificial Sequence
<220> FEATURE:
<223> OTHER INFORMATION: Forward Primer sequence

<400> SEQUENCE: 85
ccccggcttc ggttct                                                16

<210> SEQ ID NO 86
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 86
agtacaagga ggaggcaagg aa                                         22

<210> SEQ ID NO 87
<211> LENGTH: 21
<212> TYPE: DNA
<213> ORGANISM: Artificial Sequence
<220> FEATURE:
<223> OTHER INFORMATION: Forward Primer sequence

<400> SEQUENCE: 87
ggaatccagg aggtggtgat g                                          21

<210> SEQ ID NO 88
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 88
cagccaacta aactgtatgc tctgt                                      25

<210> SEQ ID NO 89
<211> LENGTH: 26
<212> TYPE: DNA
<213> ORGANISM: Artificial Sequence
<220> FEATURE:
<223> OTHER INFORMATION: Forward Primer sequence

<400> SEQUENCE: 89
aagaaattag aagtggccat ggaaga                                     26

<210> SEQ ID NO 90
<211> LENGTH: 27
<212> TYPE: DNA
<213> ORGANISM: Artificial Sequence
<220> FEATURE:
<223> OTHER INFORMATION: Reverse Primer sequence

<400> SEQUENCE: 90
gggtgctttt gtacagtaat tataggt                                    27
```

<210> SEQ ID NO 91
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 91
caggtcaatc tactgctaag ggatt                25

<210> SEQ ID NO 92
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 92
ccgctactga aagataaagc cactt                25

<210> SEQ ID NO 93
<211> LENGTH: 18
<212> TYPE: DNA
<213> ORGANISM: Artificial Sequence
<220> FEATURE:
<223> OTHER INFORMATION: Forward Primer sequence

<400> SEQUENCE: 93
aggctggtgg aggctagt                18

<210> SEQ ID NO 94
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 94
gaaaccctgg gaaaccatac cat                23

<210> SEQ ID NO 95
<211> LENGTH: 29
<212> TYPE: DNA
<213> ORGANISM: Artificial Sequence
<220> FEATURE:
<223> OTHER INFORMATION: Forward Primer sequence

<400> SEQUENCE: 95
cttgggatgt tttataagtg tctgtctgt                29

<210> SEQ ID NO 96
<211> LENGTH: 21
<212> TYPE: DNA
<213> ORGANISM: Artificial Sequence
<220> FEATURE:
<223> OTHER INFORMATION: Reverse Primer sequence

<400> SEQUENCE: 96
gggaagggac ctgaggatag g                21

<210> SEQ ID NO 97
<211> LENGTH: 24
<212> TYPE: DNA
<213> ORGANISM: Artificial Sequence
<220> FEATURE:
<223> OTHER INFORMATION: Forward Primer sequence

```
<400> SEQUENCE: 97
ttgacatgag gccatttgct atca                                          24

<210> SEQ ID NO 98
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 98
gcacctaaca acattgtagc ctcaa                                         25

<210> SEQ ID NO 99
<211> LENGTH: 22
<212> TYPE: DNA
<213> ORGANISM: Artificial Sequence
<220> FEATURE:
<223> OTHER INFORMATION: Forward Primer sequence

<400> SEQUENCE: 99
agatctggga caaggtctgt gt                                            22

<210> SEQ ID NO 100
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 100
gctaatgtca acgatgtcca tcaag                                         25

<210> SEQ ID NO 101
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 101
acttctccag ttgaaagggt atcca                                         25

<210> SEQ ID NO 102
<211> LENGTH: 26
<212> TYPE: DNA
<213> ORGANISM: Artificial Sequence
<220> FEATURE:
<223> OTHER INFORMATION: Reverse Primer sequence

<400> SEQUENCE: 102
ggtaatggag actcatgaat gacact                                        26

<210> SEQ ID NO 103
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 103
gcctagaata tcctgcagtg gtaga                                         25

<210> SEQ ID NO 104
```

```
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 104
tgcttccagt cttggcatct ttt                                              23

<210> SEQ ID NO 105
<211> LENGTH: 19
<212> TYPE: DNA
<213> ORGANISM: Artificial Sequence
<220> FEATURE:
<223> OTHER INFORMATION: Forward Primer sequence

<400> SEQUENCE: 105
ggaggaaggc cagcagaag                                                   19

<210> SEQ ID NO 106
<211> LENGTH: 19
<212> TYPE: DNA
<213> ORGANISM: Artificial Sequence
<220> FEATURE:
<223> OTHER INFORMATION: Reverse Primer sequence

<400> SEQUENCE: 106
acaacagcag ctccaacca                                                   19

<210> SEQ ID NO 107
<211> LENGTH: 23
<212> TYPE: DNA
<213> ORGANISM: Artificial Sequence
<220> FEATURE:
<223> OTHER INFORMATION: Forward Primer sequence

<400> SEQUENCE: 107
cagccttttc accaaccttc aaa                                              23

<210> SEQ ID NO 108
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 108
accagacacc acctatgatt gga                                              23

<210> SEQ ID NO 109
<211> LENGTH: 20
<212> TYPE: DNA
<213> ORGANISM: Artificial Sequence
<220> FEATURE:
<223> OTHER INFORMATION: Forward Primer sequence

<400> SEQUENCE: 109
gataggcgca ccaggaatga                                                  20

<210> SEQ ID NO 110
<211> LENGTH: 24
<212> TYPE: DNA
<213> ORGANISM: Artificial Sequence
<220> FEATURE:
<223> OTHER INFORMATION: Reverse Primer sequence

<400> SEQUENCE: 110
```

```
cagtggccaa acacgaatta aagt                                          24

<210> SEQ ID NO 111
<211> LENGTH: 22
<212> TYPE: DNA
<213> ORGANISM: Artificial Sequence
<220> FEATURE:
<223> OTHER INFORMATION: Forward Primer sequence

<400> SEQUENCE: 111
catccactca ccactgtatc ca                                            22

<210> SEQ ID NO 112
<211> LENGTH: 19
<212> TYPE: DNA
<213> ORGANISM: Artificial Sequence
<220> FEATURE:
<223> OTHER INFORMATION: Reverse Primer sequence

<400> SEQUENCE: 112
ggcatgaggc ttggaagca                                                19

<210> SEQ ID NO 113
<211> LENGTH: 19
<212> TYPE: DNA
<213> ORGANISM: Artificial Sequence
<220> FEATURE:
<223> OTHER INFORMATION: Forward Primer sequence

<400> SEQUENCE: 113
gagcacccac tgtgtacga                                                19

<210> SEQ ID NO 114
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 114
acaccagcag aattatgcca tactt                                         25

<210> SEQ ID NO 115
<211> LENGTH: 28
<212> TYPE: DNA
<213> ORGANISM: Artificial Sequence
<220> FEATURE:
<223> OTHER INFORMATION: Forward Primer sequence

<400> SEQUENCE: 115
gggatggatt taccagaaag atgatcag                                      28

<210> SEQ ID NO 116
<211> LENGTH: 23
<212> TYPE: DNA
<213> ORGANISM: Artificial Sequence
<220> FEATURE:
<223> OTHER INFORMATION: Reverse Primer sequence]

<400> SEQUENCE: 116
agctgaccaa gcatttcatg agt                                           23

<210> SEQ ID NO 117
<211> LENGTH: 29
<212> TYPE: DNA
```

```
<213> ORGANISM: Artificial Sequence
<220> FEATURE:
<223> OTHER INFORMATION: Forward Primer sequence

<400> SEQUENCE: 117
actcaggctt accatatttg tttgtactt                                          29

<210> SEQ ID NO 118
<211> LENGTH: 21
<212> TYPE: DNA
<213> ORGANISM: Artificial Sequence
<220> FEATURE:
<223> OTHER INFORMATION: Reverse Primer sequence

<400> SEQUENCE: 118
tgcatggcaa aggaaatccc a                                                  21

<210> SEQ ID NO 119
<211> LENGTH: 33
<212> TYPE: DNA
<213> ORGANISM: Artificial Sequence
<220> FEATURE:
<223> OTHER INFORMATION: Forward Primer sequence

<400> SEQUENCE: 119
aggtgataaa tagcttacat tttagagttt gct                                     33

<210> SEQ ID NO 120
<211> LENGTH: 21
<212> TYPE: DNA
<213> ORGANISM: Artificial Sequence
<220> FEATURE:
<223> OTHER INFORMATION: Reverse Primer sequence

<400> SEQUENCE: 120
ccatacctga acgtgatgcc a                                                  21

<210> SEQ ID NO 121
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 121
tgatggtttt ctggtgtccc tttag                                              25

<210> SEQ ID NO 122
<211> LENGTH: 21
<212> TYPE: DNA
<213> ORGANISM: Artificial Sequence
<220> FEATURE:
<223> OTHER INFORMATION: Reverse Primer sequence

<400> SEQUENCE: 122
ccacttccct gggattgaac t                                                  21

<210> SEQ ID NO 123
<211> LENGTH: 19
<212> TYPE: DNA
<213> ORGANISM: Artificial Sequence
<220> FEATURE:
<223> OTHER INFORMATION: Forward Primer sequence

<400> SEQUENCE: 123
gcccaagagc ctgagttct                                                     19
```

<210> SEQ ID NO 124
<211> LENGTH: 19
<212> TYPE: DNA
<213> ORGANISM: Artificial Sequence
<220> FEATURE:
<223> OTHER INFORMATION: Reverse Primer sequence

<400> SEQUENCE: 124
ccgggccatc gatgaagag                                              19

<210> SEQ ID NO 125
<211> LENGTH: 23
<212> TYPE: DNA
<213> ORGANISM: Artificial Sequence
<220> FEATURE:
<223> OTHER INFORMATION: Forward Primer sequence

<400> SEQUENCE: 125
ccatcgtaag gcttggaatc gaa                                         23

<210> SEQ ID NO 126
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 126
ggctacttcc cagcaaggta at                                          22

<210> SEQ ID NO 127
<211> LENGTH: 20
<212> TYPE: DNA
<213> ORGANISM: Artificial Sequence
<220> FEATURE:
<223> OTHER INFORMATION: Forward Primer sequence

<400> SEQUENCE: 127
ggtccagccc ttctcaacac                                             20

<210> SEQ ID NO 128
<211> LENGTH: 19
<212> TYPE: DNA
<213> ORGANISM: Artificial Sequence
<220> FEATURE:
<223> OTHER INFORMATION: Reverse Primer sequence

<400> SEQUENCE: 128
accagcactc accgctaaa                                              19

<210> SEQ ID NO 129
<211> LENGTH: 23
<212> TYPE: DNA
<213> ORGANISM: Artificial Sequence
<220> FEATURE:
<223> OTHER INFORMATION: Forward Primer sequence

<400> SEQUENCE: 129
tcctggtagg gatacagctc att                                         23

<210> SEQ ID NO 130
<211> LENGTH: 20
<212> TYPE: DNA
<213> ORGANISM: Artificial Sequence
<220> FEATURE:

<223> OTHER INFORMATION: Reverse Primer sequence

<400> SEQUENCE: 130
gtctggtttg cagggacact                                          20

<210> SEQ ID NO 131
<211> LENGTH: 18
<212> TYPE: DNA
<213> ORGANISM: Artificial Sequence
<220> FEATURE:
<223> OTHER INFORMATION: Forward Primer sequence

<400> SEQUENCE: 131
ggcagccgat ggtcagta                                            18

<210> SEQ ID NO 132
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 132
ggccttgggc agaacagtaa ata                                      23

<210> SEQ ID NO 133
<211> LENGTH: 21
<212> TYPE: DNA
<213> ORGANISM: Artificial Sequence
<220> FEATURE:
<223> OTHER INFORMATION: Forward Primer sequence

<400> SEQUENCE: 133
ccctctgctg gcacctttaa g                                        21

<210> SEQ ID NO 134
<211> LENGTH: 18
<212> TYPE: DNA
<213> ORGANISM: Artificial Sequence
<220> FEATURE:
<223> OTHER INFORMATION: Reverse Primer sequence

<400> SEQUENCE: 134
gcccaggtgg gactgaga                                            18

<210> SEQ ID NO 135
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 135
gcttagagcc tccatttctt tcct                                     24

<210> SEQ ID NO 136
<211> LENGTH: 24
<212> TYPE: DNA
<213> ORGANISM: Artificial Sequence
<220> FEATURE:
<223> OTHER INFORMATION: Reverse Primer sequence

<400> SEQUENCE: 136
agactttcca tccagtgaga tcca                                     24

```
<210> SEQ ID NO 137
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 137
gattgacaaa tttcgtgacc cacaa                                               25

<210> SEQ ID NO 138
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 138
tcagcctgct cataagactc aaatg                                               25

<210> SEQ ID NO 139
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 139
tccagagctt tagaggaaga cacat                                               25

<210> SEQ ID NO 140
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 140
gtggtctgct tctgtcctct ttt                                                 23

<210> SEQ ID NO 141
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 141
tgctgtcctt actcattcca catc                                                24

<210> SEQ ID NO 142
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 142
gcctaagttt gcagaccctc aa                                                  22

<210> SEQ ID NO 143
<211> LENGTH: 25
<212> TYPE: DNA
<213> ORGANISM: Artificial Sequence
<220> FEATURE:
<223> OTHER INFORMATION: Forward Primer sequence
```

<400> SEQUENCE: 143
gtggtccata tggtcccttc ttaaa  25

<210> SEQ ID NO 144
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 144
aaagggactc ttccggttct tg  22

<210> SEQ ID NO 145
<211> LENGTH: 19
<212> TYPE: DNA
<213> ORGANISM: Artificial Sequence
<220> FEATURE:
<223> OTHER INFORMATION: Forward Primer sequence

<400> SEQUENCE: 145
ccgttcgacc cttgatgct  19

<210> SEQ ID NO 146
<211> LENGTH: 30
<212> TYPE: DNA
<213> ORGANISM: Artificial Sequence
<220> FEATURE:
<223> OTHER INFORMATION: Reverse Primer sequence

<400> SEQUENCE: 146
actacgaaac aaatatactg agatcctcct  30

<210> SEQ ID NO 147
<211> LENGTH: 21
<212> TYPE: DNA
<213> ORGANISM: Artificial Sequence
<220> FEATURE:
<223> OTHER INFORMATION: Forward Primer sequence

<400> SEQUENCE: 147
ggtgactcac tgggcagatt c  21

<210> SEQ ID NO 148
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 148
gagtgcctac agcaaagaaa tgg  23

<210> SEQ ID NO 149
<211> LENGTH: 18
<212> TYPE: DNA
<213> ORGANISM: Artificial Sequence
<220> FEATURE:
<223> OTHER INFORMATION: Forward Primer sequence

<400> SEQUENCE: 149
gctctgccga tgtcctca  18

<210> SEQ ID NO 150
<211> LENGTH: 20

```
<212> TYPE: DNA
<213> ORGANISM: Artificial Sequence
<220> FEATURE:
<223> OTHER INFORMATION: Reverse Primer sequence

<400> SEQUENCE: 150
cagtgtgggc attgcagttc                                               20

<210> SEQ ID NO 151
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 151
cagtactggt gagggaaatc tgtt                                          24

<210> SEQ ID NO 152
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 152
tccaggctta taacgtagga cacta                                         25

<210> SEQ ID NO 153
<211> LENGTH: 23
<212> TYPE: DNA
<213> ORGANISM: Artificial Sequence
<220> FEATURE:
<223> OTHER INFORMATION: Forward Primer sequence

<400> SEQUENCE: 153
ccacttccct caatcatgtg aca                                           23

<210> SEQ ID NO 154
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 154
gggttttgcc aactttttct ggatt                                         25

<210> SEQ ID NO 155
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 155
gtgcgaaggt tagtttctga ggaa                                          24

<210> SEQ ID NO 156
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 156
```
gagaggaacc cagcaagtta gtt                                                    23

<210> SEQ ID NO 157
<211> LENGTH: 20
<212> TYPE: DNA
<213> ORGANISM: Artificial Sequence
<220> FEATURE:
<223> OTHER INFORMATION: Forward Primer sequence

<400> SEQUENCE: 157
cccatgggag atgctcttga                                                        20

<210> SEQ ID NO 158
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 158
ggtctcctgg ttccatctct tc                                                     22

<210> SEQ ID NO 159
<211> LENGTH: 18
<212> TYPE: DNA
<213> ORGANISM: Artificial Sequence
<220> FEATURE:
<223> OTHER INFORMATION: Forward Primer sequence

<400> SEQUENCE: 159
gccctgtccc tgcttctg                                                          18

<210> SEQ ID NO 160
<211> LENGTH: 19
<212> TYPE: DNA
<213> ORGANISM: Artificial Sequence
<220> FEATURE:
<223> OTHER INFORMATION: Reverse Primer sequence

<400> SEQUENCE: 160
aggtgcccct tagccagta                                                         19

<210> SEQ ID NO 161
<211> LENGTH: 20
<212> TYPE: DNA
<213> ORGANISM: Artificial Sequence
<220> FEATURE:
<223> OTHER INFORMATION: Forward Primer sequence

<400> SEQUENCE: 161
caggcagctt cttggtcaga                                                        20

<210> SEQ ID NO 162
<211> LENGTH: 18
<212> TYPE: DNA
<213> ORGANISM: Artificial Sequence
<220> FEATURE:
<223> OTHER INFORMATION: Reverse Primer sequence

<400> SEQUENCE: 162
gtgtcccggc atggatgt                                                          18

<210> SEQ ID NO 163
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 163
agcatcctat gcctttgaca aaga                                          24

<210> SEQ ID NO 164
<211> LENGTH: 21
<212> TYPE: DNA
<213> ORGANISM: Artificial Sequence
<220> FEATURE:
<223> OTHER INFORMATION: Reverse Primer sequence

<400> SEQUENCE: 164
cagtaagcaa gcaggctagg t                                             21

<210> SEQ ID NO 165
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 165
gttctgattt ctactcctcc acaca                                         25

<210> SEQ ID NO 166
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 166
ggaatcagtc tttgcatttg catct                                         25

<210> SEQ ID NO 167
<211> LENGTH: 22
<212> TYPE: DNA
<213> ORGANISM: Artificial Sequence
<220> FEATURE:
<223> OTHER INFORMATION: Forward Primer sequence

<400> SEQUENCE: 167
ctgatgtgtc ttggcaggtc at                                            22

<210> SEQ ID NO 168
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 168
ccatggatca ggacgtcgaa ag                                            22

<210> SEQ ID NO 169
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 169
ccttacccat cccaactagc ctta                                          24

```
<210> SEQ ID NO 170
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 170
gtagagtgag tgtgacgttg gat                                         23

<210> SEQ ID NO 171
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 171
cctcctgatc atactctggt acct                                        24

<210> SEQ ID NO 172
<211> LENGTH: 21
<212> TYPE: DNA
<213> ORGANISM: Artificial Sequence
<220> FEATURE:
<223> OTHER INFORMATION: Reverse Primer sequence

<400> SEQUENCE: 172
cacattccct ggcaggagta g                                           21

<210> SEQ ID NO 173
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 173
cacatgaggc tttcggagga ataa                                        24

<210> SEQ ID NO 174
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 174
ccttgatgcc ctggatagct tttac                                       25

<210> SEQ ID NO 175
<211> LENGTH: 19
<212> TYPE: DNA
<213> ORGANISM: Artificial Sequence
<220> FEATURE:
<223> OTHER INFORMATION: Forward Primer sequence

<400> SEQUENCE: 175
ccatccctct ccacagcaa                                              19

<210> SEQ ID NO 176
<211> LENGTH: 21
<212> TYPE: DNA
<213> ORGANISM: Artificial Sequence
<220> FEATURE:
<223> OTHER INFORMATION: Reverse Primer sequence
```

-continued

```
<400> SEQUENCE: 176
gtctgggaac tcgccaatca t                                              21

<210> SEQ ID NO 177
<211> LENGTH: 23
<212> TYPE: DNA
<213> ORGANISM: Artificial Sequence
<220> FEATURE:
<223> OTHER INFORMATION: Forward Primer sequence

<400> SEQUENCE: 177
ggaaattgtc aggtcagctc agt                                            23

<210> SEQ ID NO 178
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 178
cccatttcat gtcctctcag aagaa                                          25

<210> SEQ ID NO 179
<211> LENGTH: 21
<212> TYPE: DNA
<213> ORGANISM: Artificial Sequence
<220> FEATURE:
<223> OTHER INFORMATION: Forward Primer sequence

<400> SEQUENCE: 179
tgctttaggc aggtgtgaac t                                              21

<210> SEQ ID NO 180
<211> LENGTH: 23
<212> TYPE: DNA
<213> ORGANISM: Artificial Sequence
<220> FEATURE:
<223> OTHER INFORMATION: Reverse Primer sequence

<400> SEQUENCE: 180
gggccaagaa ggtacaggaa ttt                                            23

<210> SEQ ID NO 181
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 181
ccccatggtc aacacaaaat gtag                                           24

<210> SEQ ID NO 182
<211> LENGTH: 19
<212> TYPE: DNA
<213> ORGANISM: Artificial Sequence
<220> FEATURE:
<223> OTHER INFORMATION: Reverse Primer sequence

<400> SEQUENCE: 182
catcacccca gaggctgtt                                                 19

<210> SEQ ID NO 183
```

```
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 183
ggtcagaaag ttaccaggac ttgt                                            24

<210> SEQ ID NO 184
<211> LENGTH: 22
<212> TYPE: DNA
<213> ORGANISM: Artificial Sequence
<220> FEATURE:
<223> OTHER INFORMATION: Reverse Primer sequence

<400> SEQUENCE: 184
ccagtgtctg cagtggacaa aa                                              22

<210> SEQ ID NO 185
<211> LENGTH: 26
<212> TYPE: DNA
<213> ORGANISM: Artificial Sequence
<220> FEATURE:
<223> OTHER INFORMATION: Forward Primer sequence

<400> SEQUENCE: 185
gtgatctgaa tgatgttgaa caagca                                          26

<210> SEQ ID NO 186
<211> LENGTH: 26
<212> TYPE: DNA
<213> ORGANISM: Artificial Sequence
<220> FEATURE:
<223> OTHER INFORMATION: Reverse Primer sequence

<400> SEQUENCE: 186
acacggatag ccagacaatg aaatac                                          26

<210> SEQ ID NO 187
<211> LENGTH: 25
<212> TYPE: DNA
<213> ORGANISM: Artificial Sequence
<220> FEATURE:
<223> OTHER INFORMATION: Forward Primer sequence

<400> SEQUENCE: 187
tcctgcaaaa tgacttgagt tggta                                           25

<210> SEQ ID NO 188
<211> LENGTH: 27
<212> TYPE: DNA
<213> ORGANISM: Artificial Sequence
<220> FEATURE:
<223> OTHER INFORMATION: Reverse Primer sequence

<400> SEQUENCE: 188
acatgtcagg cctttttatt ttgtagc                                         27

<210> SEQ ID NO 189
<211> LENGTH: 24
<212> TYPE: DNA
<213> ORGANISM: Artificial Sequence
<220> FEATURE:
<223> OTHER INFORMATION: Forward Primer sequence

<400> SEQUENCE: 189
```
cttccaggga aattcacctc ttct                                          24

<210> SEQ ID NO 190
<211> LENGTH: 25
<212> TYPE: DNA
<213> ORGANISM: Artificial Sequence
<220> FEATURE:
<223> OTHER INFORMATION: Reverse Primer sequence

<400> SEQUENCE: 190
gtttccctgt tgagaatgtt tccat                                         25

<210> SEQ ID NO 191
<211> LENGTH: 22
<212> TYPE: DNA
<213> ORGANISM: Artificial Sequence
<220> FEATURE:
<223> OTHER INFORMATION: Forward Primer sequence

<400> SEQUENCE: 191
gaaagggaag agcacacagt ct                                            22

<210> SEQ ID NO 192
<211> LENGTH: 20
<212> TYPE: DNA
<213> ORGANISM: Artificial Sequence
<220> FEATURE:
<223> OTHER INFORMATION: Reverse Primer sequence

<400> SEQUENCE: 192
ggcctcaaag tcccacacaa                                               20

<210> SEQ ID NO 193
<211> LENGTH: 22
<212> TYPE: DNA
<213> ORGANISM: Artificial Sequence
<220> FEATURE:
<223> OTHER INFORMATION: Probe sequence

<400> SEQUENCE: 193
tcttccaaga cctgcacatc cg                                            22

<210> SEQ ID NO 194
<211> LENGTH: 22
<212> TYPE: DNA
<213> ORGANISM: Artificial Sequence
<220> FEATURE:
<223> OTHER INFORMATION: Probe sequence

<400> SEQUENCE: 194
caggagacag tgagtgagca cc                                            22

<210> SEQ ID NO 195
<211> LENGTH: 19
<212> TYPE: DNA
<213> ORGANISM: Artificial Sequence
<220> FEATURE:
<223> OTHER INFORMATION: Probe sequence

<400> SEQUENCE: 195
ccccagcttc agcagcttg                                                19

<210> SEQ ID NO 196
<211> LENGTH: 22
<212> TYPE: DNA

```
<213> ORGANISM: Artificial Sequence
<220> FEATURE:
<223> OTHER INFORMATION: Probe sequence

<400> SEQUENCE: 196
ccgtgccaag atcactgact ta                                              22

<210> SEQ ID NO 197
<211> LENGTH: 21
<212> TYPE: DNA
<213> ORGANISM: Artificial Sequence
<220> FEATURE:
<223> OTHER INFORMATION: Probe sequence

<400> SEQUENCE: 197
aaccaccaac aaagggattc t                                               21

<210> SEQ ID NO 198
<211> LENGTH: 22
<212> TYPE: DNA
<213> ORGANISM: Artificial Sequence
<220> FEATURE:
<223> OTHER INFORMATION: Probe sequence

<400> SEQUENCE: 198
accttcccag tttgataagc ac                                              22

<210> SEQ ID NO 199
<211> LENGTH: 19
<212> TYPE: DNA
<213> ORGANISM: Artificial Sequence
<220> FEATURE:
<223> OTHER INFORMATION: Probe sequence

<400> SEQUENCE: 199
ctggcctgtg tgtacttct                                                  19

<210> SEQ ID NO 200
<211> LENGTH: 22
<212> TYPE: DNA
<213> ORGANISM: Artificial Sequence
<220> FEATURE:
<223> OTHER INFORMATION: Probe sequence

<400> SEQUENCE: 200
acccatgcct ctttctaata ac                                              22

<210> SEQ ID NO 201
<211> LENGTH: 22
<212> TYPE: DNA
<213> ORGANISM: Artificial Sequence
<220> FEATURE:
<223> OTHER INFORMATION: Probe sequence

<400> SEQUENCE: 201
cctgcctacc aaagaggata ca                                              22

<210> SEQ ID NO 202
<211> LENGTH: 19
<212> TYPE: DNA
<213> ORGANISM: Artificial Sequence
<220> FEATURE:
<223> OTHER INFORMATION: Probe sequence

<400> SEQUENCE: 202
tcccagccca ctgtaaatg                                                  19
```

<210> SEQ ID NO 203
<211> LENGTH: 21
<212> TYPE: DNA
<213> ORGANISM: Artificial Sequence
<220> FEATURE:
<223> OTHER INFORMATION: Probe sequence

<400> SEQUENCE: 203
aatgccacca gtgaccttca g                                              21

<210> SEQ ID NO 204
<211> LENGTH: 22
<212> TYPE: DNA
<213> ORGANISM: Artificial Sequence
<220> FEATURE:
<223> OTHER INFORMATION: Probe sequence

<400> SEQUENCE: 204
tcttctttgc tcctgagacc tc                                             22

<210> SEQ ID NO 205
<211> LENGTH: 22
<212> TYPE: DNA
<213> ORGANISM: Artificial Sequence
<220> FEATURE:
<223> OTHER INFORMATION: Probe sequence

<400> SEQUENCE: 205
ataggtgtcc ctgtaaagca ac                                             22

<210> SEQ ID NO 206
<211> LENGTH: 20
<212> TYPE: DNA
<213> ORGANISM: Artificial Sequence
<220> FEATURE:
<223> OTHER INFORMATION: Probe sequence

<400> SEQUENCE: 206
tcctgctgcc cactgacctg                                                20

<210> SEQ ID NO 207
<211> LENGTH: 22
<212> TYPE: DNA
<213> ORGANISM: Artificial Sequence
<220> FEATURE:
<223> OTHER INFORMATION: Probe sequence

<400> SEQUENCE: 207
ccacacaggc tccttggagt aa                                             22

<210> SEQ ID NO 208
<211> LENGTH: 20
<212> TYPE: DNA
<213> ORGANISM: Artificial Sequence
<220> FEATURE:
<223> OTHER INFORMATION: Probe sequence

<400> SEQUENCE: 208
ttgctgttgg ctgaatcact                                                20

<210> SEQ ID NO 209
<211> LENGTH: 20
<212> TYPE: DNA
<213> ORGANISM: Artificial Sequence
<220> FEATURE:

```
<223> OTHER INFORMATION: Probe sequence

<400> SEQUENCE: 209
aatggagaag ggaaaattac                                              20

<210> SEQ ID NO 210
<211> LENGTH: 22
<212> TYPE: DNA
<213> ORGANISM: Artificial Sequence
<220> FEATURE:
<223> OTHER INFORMATION: Probe sequence

<400> SEQUENCE: 210
cagggagaca aaacagaaat at                                           22

<210> SEQ ID NO 211
<211> LENGTH: 17
<212> TYPE: DNA
<213> ORGANISM: Artificial Sequence
<220> FEATURE:
<223> OTHER INFORMATION: Probe sequence

<400> SEQUENCE: 211
ccggagccgc tgcacat                                                 17

<210> SEQ ID NO 212
<211> LENGTH: 20
<212> TYPE: DNA
<213> ORGANISM: Artificial Sequence
<220> FEATURE:
<223> OTHER INFORMATION: Probe sequence

<400> SEQUENCE: 212
ctaggtactg cgccactttt                                              20

<210> SEQ ID NO 213
<211> LENGTH: 21
<212> TYPE: DNA
<213> ORGANISM: Artificial Sequence
<220> FEATURE:
<223> OTHER INFORMATION: Probe sequence

<400> SEQUENCE: 213
atgcaactca tgctgaattt a                                            21

<210> SEQ ID NO 214
<211> LENGTH: 21
<212> TYPE: DNA
<213> ORGANISM: Artificial Sequence
<220> FEATURE:
<223> OTHER INFORMATION: Probe sequence

<400> SEQUENCE: 214
cctcaagctc cgacccctcc t                                            21

<210> SEQ ID NO 215
<211> LENGTH: 22
<212> TYPE: DNA
<213> ORGANISM: Artificial Sequence
<220> FEATURE:
<223> OTHER INFORMATION: Probe sequence

<400> SEQUENCE: 215
catgtatagc tgcatagatt tc                                           22
```

```
<210> SEQ ID NO 216
<211> LENGTH: 22
<212> TYPE: DNA
<213> ORGANISM: Artificial Sequence
<220> FEATURE:
<223> OTHER INFORMATION: Probe sequence

<400> SEQUENCE: 216
cagtctgatg gtcccaagtt ga                                                22

<210> SEQ ID NO 217
<211> LENGTH: 21
<212> TYPE: DNA
<213> ORGANISM: Artificial Sequence
<220> FEATURE:
<223> OTHER INFORMATION: Probe sequence

<400> SEQUENCE: 217 ccacccttc tacatttctc c                                                  21

<210> SEQ ID NO 218
<211> LENGTH: 22
<212> TYPE: DNA
<213> ORGANISM: Artificial Sequence
<220> FEATURE:
<223> OTHER INFORMATION: Probe sequence

<400> SEQUENCE: 218
tccttgccaa ctagaaacta tg                                                22

<210> SEQ ID NO 219
<211> LENGTH: 22
<212> TYPE: DNA
<213> ORGANISM: Artificial Sequence
<220> FEATURE:
<223> OTHER INFORMATION: Probe sequence

<400> SEQUENCE: 219
aaagaatcag gcaggtaaag ct                                                22

<210> SEQ ID NO 220
<211> LENGTH: 22
<212> TYPE: DNA
<213> ORGANISM: Artificial Sequence
<220> FEATURE:
<223> OTHER INFORMATION: Probe sequence

<400> SEQUENCE: 220
acgctgggct atttcatcat ct                                                22

<210> SEQ ID NO 221
<211> LENGTH: 22
<212> TYPE: DNA
<213> ORGANISM: Artificial Sequence
<220> FEATURE:
<223> OTHER INFORMATION: Probe sequence

<400> SEQUENCE: 221
cttcccccag caaagttagt tg                                                22

<210> SEQ ID NO 222
<211> LENGTH: 22
<212> TYPE: DNA
<213> ORGANISM: Artificial Sequence
<220> FEATURE:
<223> OTHER INFORMATION: Probe sequence
```

```
<400> SEQUENCE: 222
ccacggtcca ctctgtccac gt                                              22

<210> SEQ ID NO 223
<211> LENGTH: 22
<212> TYPE: DNA
<213> ORGANISM: Artificial Sequence
<220> FEATURE:
<223> OTHER INFORMATION: Probe sequence

<400> SEQUENCE: 223
acaaggcaag acagagatgt ac                                              22

<210> SEQ ID NO 224
<211> LENGTH: 22
<212> TYPE: DNA
<213> ORGANISM: Artificial Sequence
<220> FEATURE:
<223> OTHER INFORMATION: Probe sequence

<400> SEQUENCE: 224
ctttgacctc agtgttaatt tt                                              22

<210> SEQ ID NO 225
<211> LENGTH: 22
<212> TYPE: DNA
<213> ORGANISM: Artificial Sequence
<220> FEATURE:
<223> OTHER INFORMATION: Probe sequence

<400> SEQUENCE: 225
ctccagtctc aacagccatt cc                                              22

<210> SEQ ID NO 226
<211> LENGTH: 21
<212> TYPE: DNA
<213> ORGANISM: Artificial Sequence
<220> FEATURE:
<223> OTHER INFORMATION: Probe sequence

<400> SEQUENCE: 226
ccaaggaaga cagcactatt c                                               21

<210> SEQ ID NO 227
<211> LENGTH: 22
<212> TYPE: DNA
<213> ORGANISM: Artificial Sequence
<220> FEATURE:
<223> OTHER INFORMATION: Probe sequence

<400> SEQUENCE: 227
ctgctgagta attcactttc cc                                              22

<210> SEQ ID NO 228
<211> LENGTH: 18
<212> TYPE: DNA
<213> ORGANISM: Artificial Sequence
<220> FEATURE:
<223> OTHER INFORMATION: Probe sequence

<400> SEQUENCE: 228
cctgcccagg agctagtg                                                   18

<210> SEQ ID NO 229
<211> LENGTH: 20
```

```
<212> TYPE: DNA
<213> ORGANISM: Artificial Sequence
<220> FEATURE:
<223> OTHER INFORMATION: Probe sequence

<400> SEQUENCE: 229
acaaccagcc acatggattc                                               20

<210> SEQ ID NO 230
<211> LENGTH: 22
<212> TYPE: DNA
<213> ORGANISM: Artificial Sequence
<220> FEATURE:
<223> OTHER INFORMATION: Probe sequence

<400> SEQUENCE: 230
ctgagcaagc atttgatcct gc                                            22

<210> SEQ ID NO 231
<211> LENGTH: 21
<212> TYPE: DNA
<213> ORGANISM: Artificial Sequence
<220> FEATURE:
<223> OTHER INFORMATION: Probe sequence

<400> SEQUENCE: 231
cttcacagac cgagataaac g                                             21

<210> SEQ ID NO 232
<211> LENGTH: 19
<212> TYPE: DNA
<213> ORGANISM: Artificial Sequence
<220> FEATURE:
<223> OTHER INFORMATION: Probe sequence

<400> SEQUENCE: 232
tcggtcttct gcatcttcc                                                19

<210> SEQ ID NO 233
<211> LENGTH: 22
<212> TYPE: DNA
<213> ORGANISM: Artificial Sequence
<220> FEATURE:
<223> OTHER INFORMATION: Probe sequence

<400> SEQUENCE: 233
acccaacaca acagcattaa gt                                            22

<210> SEQ ID NO 234
<211> LENGTH: 18
<212> TYPE: DNA
<213> ORGANISM: Artificial Sequence
<220> FEATURE:
<223> OTHER INFORMATION: Probe sequence

<400> SEQUENCE: 234
caagggctgg cactccca                                                 18

<210> SEQ ID NO 235
<211> LENGTH: 22
<212> TYPE: DNA
<213> ORGANISM: Artificial Sequence
<220> FEATURE:
<223> OTHER INFORMATION: Probe sequence

<400> SEQUENCE: 235
```

```
tttcggttgt ttcggcgatt tg                                          22

<210> SEQ ID NO 236
<211> LENGTH: 18
<212> TYPE: DNA
<213> ORGANISM: Artificial Sequence
<220> FEATURE:
<223> OTHER INFORMATION: Probe sequence

<400> SEQUENCE: 236
atcaggcagc caggattt                                               18

<210> SEQ ID NO 237
<211> LENGTH: 23
<212> TYPE: DNA
<213> ORGANISM: Artificial Sequence
<220> FEATURE:
<223> OTHER INFORMATION: Probe sequence

<400> SEQUENCE: 237
acctcttcat ctgctaatcc ttc                                         23

<210> SEQ ID NO 238
<211> LENGTH: 21
<212> TYPE: DNA
<213> ORGANISM: Artificial Sequence
<220> FEATURE:
<223> OTHER INFORMATION: Probe sequence

<400> SEQUENCE: 238
cagcccagca aatgcacaca t                                           21

<210> SEQ ID NO 239
<211> LENGTH: 20
<212> TYPE: DNA
<213> ORGANISM: Artificial Sequence
<220> FEATURE:
<223> OTHER INFORMATION: Probe sequence

<400> SEQUENCE: 239
ctgcgggctt taggactcca                                             20

<210> SEQ ID NO 240
<211> LENGTH: 22
<212> TYPE: DNA
<213> ORGANISM: Artificial Sequence
<220> FEATURE:
<223> OTHER INFORMATION: Probe sequence

<400> SEQUENCE: 240
acttcctatg acagccaatc ac                                          22

<210> SEQ ID NO 241
<211> LENGTH: 21
<212> TYPE: DNA
<213> ORGANISM: Artificial Sequence
<220> FEATURE:
<223> OTHER INFORMATION: Probe sequence

<400> SEQUENCE: 241
aagccatcac taggaacttc t                                           21

<210> SEQ ID NO 242
<211> LENGTH: 19
<212> TYPE: DNA
<213> ORGANISM: Artificial Sequence
```

-continued

<220> FEATURE:
<223> OTHER INFORMATION: Probe sequence

<400> SEQUENCE: 242
ttgagccagc agaaatgtt                                        19

<210> SEQ ID NO 243
<211> LENGTH: 22
<212> TYPE: DNA
<213> ORGANISM: Artificial Sequence
<220> FEATURE:
<223> OTHER INFORMATION: Probe sequence

<400> SEQUENCE: 243
cagatcagtg cagtgtttct ca                                    22

<210> SEQ ID NO 244
<211> LENGTH: 22
<212> TYPE: DNA
<213> ORGANISM: Artificial Sequence
<220> FEATURE:
<223> OTHER INFORMATION: Probe sequence

<400> SEQUENCE: 244
ttgctccatt ccagaagata gc                                    22

<210> SEQ ID NO 245
<211> LENGTH: 22
<212> TYPE: DNA
<213> ORGANISM: Artificial Sequence
<220> FEATURE:
<223> OTHER INFORMATION: Probe sequence

<400> SEQUENCE: 245
ctgagaagat gcaaccaatc ct                                    22

<210> SEQ ID NO 246
<211> LENGTH: 24
<212> TYPE: DNA
<213> ORGANISM: Artificial Sequence
<220> FEATURE:
<223> OTHER INFORMATION: Probe sequence

<400> SEQUENCE: 246
aagcgatgat caattacgaa aact                                  24

<210> SEQ ID NO 247
<211> LENGTH: 23
<212> TYPE: DNA
<213> ORGANISM: Artificial Sequence
<220> FEATURE:
<223> OTHER INFORMATION: Probe sequence

<400> SEQUENCE: 247
ccgccatata cttccctaaa gct                                   23

<210> SEQ ID NO 248
<211> LENGTH: 20
<212> TYPE: DNA
<213> ORGANISM: Artificial Sequence
<220> FEATURE:
<223> OTHER INFORMATION: Probe sequence

<400> SEQUENCE: 248
tctcctccct ttgttttccc                                       20

<210> SEQ ID NO 249
<211> LENGTH: 21
<212> TYPE: DNA
<213> ORGANISM: Artificial Sequence
<220> FEATURE:
<223> OTHER INFORMATION: Probe sequence

<400> SEQUENCE: 249
acgtggctca gcactgtata c                                        21

<210> SEQ ID NO 250
<211> LENGTH: 20
<212> TYPE: DNA
<213> ORGANISM: Artificial Sequence
<220> FEATURE:
<223> OTHER INFORMATION: Probe sequence

<400> SEQUENCE: 250
acgtcacctc tctgaattat                                          20

<210> SEQ ID NO 251
<211> LENGTH: 18
<212> TYPE: DNA
<213> ORGANISM: Artificial Sequence
<220> FEATURE:
<223> OTHER INFORMATION: Probe sequence

<400> SEQUENCE: 251
ctgggccttg gttttcca                                            18

<210> SEQ ID NO 252
<211> LENGTH: 21
<212> TYPE: DNA
<213> ORGANISM: Artificial Sequence
<220> FEATURE:
<223> OTHER INFORMATION: Probe sequence

<400> SEQUENCE: 252
ctgtgggctt tacaaatttt a                                        21

<210> SEQ ID NO 253
<211> LENGTH: 21
<212> TYPE: DNA
<213> ORGANISM: Artificial Sequence
<220> FEATURE:
<223> OTHER INFORMATION: Probe sequence

<400> SEQUENCE: 253
actgagagtc aaggcaatca t                                        21

<210> SEQ ID NO 254
<211> LENGTH: 22
<212> TYPE: DNA
<213> ORGANISM: Artificial Sequence
<220> FEATURE:
<223> OTHER INFORMATION: Probe sequence

<400> SEQUENCE: 254
accatgtcct cctgtgtccg tc                                       22

<210> SEQ ID NO 255
<211> LENGTH: 22
<212> TYPE: DNA
<213> ORGANISM: Artificial Sequence
<220> FEATURE:
<223> OTHER INFORMATION: Probe sequence

<400> SEQUENCE: 255
caactgctca ttggttattt tc                                           22

<210> SEQ ID NO 256
<211> LENGTH: 19
<212> TYPE: DNA
<213> ORGANISM: Artificial Sequence
<220> FEATURE:
<223> OTHER INFORMATION: Probe sequence

<400> SEQUENCE: 256
aagcccttga gccatctttt                                              19

<210> SEQ ID NO 257
<211> LENGTH: 21
<212> TYPE: DNA
<213> ORGANISM: Artificial Sequence
<220> FEATURE:
<223> OTHER INFORMATION: Probe sequence

<400> SEQUENCE: 257
ttcggcaatg accatccttt g                                            21

<210> SEQ ID NO 258
<211> LENGTH: 21
<212> TYPE: DNA
<213> ORGANISM: Artificial Sequence
<220> FEATURE:
<223> OTHER INFORMATION: Probe sequence

<400> SEQUENCE: 258
cctcttgggc atgtctttcc t                                            21

<210> SEQ ID NO 259
<211> LENGTH: 23
<212> TYPE: DNA
<213> ORGANISM: Artificial Sequence
<220> FEATURE:
<223> OTHER INFORMATION: Probe sequence

<400> SEQUENCE: 259
cagataggag ccttgaagaa aca                                          23

<210> SEQ ID NO 260
<211> LENGTH: 20
<212> TYPE: DNA
<213> ORGANISM: Artificial Sequence
<220> FEATURE:
<223> OTHER INFORMATION: Probe sequence

<400> SEQUENCE: 260
ttgcgaaacg cgattgccca                                              20

<210> SEQ ID NO 261
<211> LENGTH: 23
<212> TYPE: DNA
<213> ORGANISM: Artificial Sequence
<220> FEATURE:
<223> OTHER INFORMATION: Probe sequence

<400> SEQUENCE: 261
atgacagaca aactgacaac tgc                                          23

<210> SEQ ID NO 262

```
<211> LENGTH: 23
<212> TYPE: DNA
<213> ORGANISM: Artificial Sequence
<220> FEATURE:
<223> OTHER INFORMATION: Probe sequence

<400> SEQUENCE: 262
caaatgaggt gaaacataaa ccc                                              23

<210> SEQ ID NO 263
<211> LENGTH: 22
<212> TYPE: DNA
<213> ORGANISM: Artificial Sequence
<220> FEATURE:
<223> OTHER INFORMATION: Probe sequence

<400> SEQUENCE: 263
aagattgctc gaccacccct cc                                               22

<210> SEQ ID NO 264
<211> LENGTH: 23
<212> TYPE: DNA
<213> ORGANISM: Artificial Sequence
<220> FEATURE:
<223> OTHER INFORMATION: Probe sequence

<400> SEQUENCE: 264
tagtggtgag aacacccatc ttc                                              23

<210> SEQ ID NO 265
<211> LENGTH: 16
<212> TYPE: DNA
<213> ORGANISM: Artificial Sequence
<220> FEATURE:
<223> OTHER INFORMATION: Probe sequence

<400> SEQUENCE: 265
ccaacccgga tgcccc                                                      16

<210> SEQ ID NO 266
<211> LENGTH: 21
<212> TYPE: DNA
<213> ORGANISM: Artificial Sequence
<220> FEATURE:
<223> OTHER INFORMATION: Probe sequence

<400> SEQUENCE: 266
caggacagaa gggactccac c                                                21

<210> SEQ ID NO 267
<211> LENGTH: 17
<212> TYPE: DNA
<213> ORGANISM: Artificial Sequence
<220> FEATURE:
<223> OTHER INFORMATION: Probe sequence

<400> SEQUENCE: 267
cactgccgca tggctct                                                     17

<210> SEQ ID NO 268
<211> LENGTH: 22
<212> TYPE: DNA
<213> ORGANISM: Artificial Sequence
<220> FEATURE:
<223> OTHER INFORMATION: Probe sequence

<400> SEQUENCE: 268
```

```
caagtcctac agtgcattca tg                                              22

<210> SEQ ID NO 269
<211> LENGTH: 22
<212> TYPE: DNA
<213> ORGANISM: Artificial Sequence
<220> FEATURE:
<223> OTHER INFORMATION: Probe sequence

<400> SEQUENCE: 269
cagtgaagcc acctttaaat ca                                              22

<210> SEQ ID NO 270
<211> LENGTH: 22
<212> TYPE: DNA
<213> ORGANISM: Artificial Sequence
<220> FEATURE:
<223> OTHER INFORMATION: Probe sequence

<400> SEQUENCE: 270
aatgggcatc atcatcaact tt                                              22

<210> SEQ ID NO 271
<211> LENGTH: 21
<212> TYPE: DNA
<213> ORGANISM: Artificial Sequence
<220> FEATURE:
<223> OTHER INFORMATION: Probe sequence

<400> SEQUENCE: 271
cccaccacca gaatagtctt t                                               21

<210> SEQ ID NO 272
<211> LENGTH: 21
<212> TYPE: DNA
<213> ORGANISM: Artificial Sequence
<220> FEATURE:
<223> OTHER INFORMATION: Probe sequence

<400> SEQUENCE: 272
ctgtgtgcag atgtcgaaaa t                                               21

<210> SEQ ID NO 273
<211> LENGTH: 20
<212> TYPE: DNA
<213> ORGANISM: Artificial Sequence
<220> FEATURE:
<223> OTHER INFORMATION: Probe sequence

<400> SEQUENCE: 273
catctggccc tggcgtacca                                                 20

<210> SEQ ID NO 274
<211> LENGTH: 20
<212> TYPE: DNA
<213> ORGANISM: Artificial Sequence
<220> FEATURE:
<223> OTHER INFORMATION: Probe sequence

<400> SEQUENCE: 274
ccaggtgttg ctgagtttat                                                 20

<210> SEQ ID NO 275
<211> LENGTH: 19
<212> TYPE: DNA
```

```
<213> ORGANISM: Artificial Sequence
<220> FEATURE:
<223> OTHER INFORMATION: Probe sequence

<400> SEQUENCE: 275
cactatggcg tgaattgtg                                                  19

<210> SEQ ID NO 276
<211> LENGTH: 19
<212> TYPE: DNA
<213> ORGANISM: Artificial Sequence
<220> FEATURE:
<223> OTHER INFORMATION: Probe sequence

<400> SEQUENCE: 276
ccattcacca gccaaagtt                                                  19

<210> SEQ ID NO 277
<211> LENGTH: 21
<212> TYPE: DNA
<213> ORGANISM: Artificial Sequence
<220> FEATURE:
<223> OTHER INFORMATION: Probe sequence

<400> SEQUENCE: 277
cccagaccag aagagttcca c                                               21

<210> SEQ ID NO 278
<211> LENGTH: 19
<212> TYPE: DNA
<213> ORGANISM: Artificial Sequence
<220> FEATURE:
<223> OTHER INFORMATION: Probe sequence

<400> SEQUENCE: 278
ctgtgcatcg gcctcctgc                                                  19

<210> SEQ ID NO 279
<211> LENGTH: 21
<212> TYPE: DNA
<213> ORGANISM: Artificial Sequence
<220> FEATURE:
<223> OTHER INFORMATION: Probe sequence

<400> SEQUENCE: 279
ccagcagcct cgatttcaga c                                               21

<210> SEQ ID NO 280
<211> LENGTH: 21
<212> TYPE: DNA
<213> ORGANISM: Artificial Sequence
<220> FEATURE:
<223> OTHER INFORMATION: Probe sequence

<400> SEQUENCE: 280
ctgcttgcag cgttccacgt c                                               21

<210> SEQ ID NO 281
<211> LENGTH: 20
<212> TYPE: DNA
<213> ORGANISM: Artificial Sequence
<220> FEATURE:
<223> OTHER INFORMATION: Probe sequence

<400> SEQUENCE: 281
acaggcccca ttaatttatg                                                 20
```

<210> SEQ ID NO 282
<211> LENGTH: 20
<212> TYPE: DNA
<213> ORGANISM: Artificial Sequence
<220> FEATURE:
<223> OTHER INFORMATION: Probe sequence

<400> SEQUENCE: 282
ccaaatgcca gtcaaagtca                                               20

<210> SEQ ID NO 283
<211> LENGTH: 22
<212> TYPE: DNA
<213> ORGANISM: Artificial Sequence
<220> FEATURE:
<223> OTHER INFORMATION: Probe sequence

<400> SEQUENCE: 283
cactggcgga ttagacatca tt                                            22

<210> SEQ ID NO 284
<211> LENGTH: 20
<212> TYPE: DNA
<213> ORGANISM: Artificial Sequence
<220> FEATURE:
<223> OTHER INFORMATION: Probe sequence

<400> SEQUENCE: 284
accttcctca cccagaataa                                               20

<210> SEQ ID NO 285
<211> LENGTH: 21
<212> TYPE: DNA
<213> ORGANISM: Artificial Sequence
<220> FEATURE:
<223> OTHER INFORMATION: Probe sequence

<400> SEQUENCE: 285
actctcctcc ctttgcttct c                                             21

<210> SEQ ID NO 286
<211> LENGTH: 22
<212> TYPE: DNA
<213> ORGANISM: Artificial Sequence
<220> FEATURE:
<223> OTHER INFORMATION: Probe sequence

<400> SEQUENCE: 286
cagggccaag tagtaaagac ct                                            22

<210> SEQ ID NO 287
<211> LENGTH: 25
<212> TYPE: DNA
<213> ORGANISM: Artificial Sequence
<220> FEATURE:
<223> OTHER INFORMATION: Probe sequence

<400> SEQUENCE: 287
aactatacga tttgaaacaa aattc                                         25

<210> SEQ ID NO 288
<211> LENGTH: 22
<212> TYPE: DNA
<213> ORGANISM: Artificial Sequence
<220> FEATURE:

```
<223> OTHER INFORMATION: Probe sequence

<400> SEQUENCE: 288
ccgatattgc tggaccacct ct                                              22

<210> SEQ ID NO 289
<211> LENGTH: 71
<212> TYPE: DNA
<213> ORGANISM: Artificial Sequence
<220> FEATURE:
<223> OTHER INFORMATION: Amplicon

<400> SEQUENCE: 289
ccagggctgc ctattgactt actcggatgt gcaggtcttg gaagaagatg aggagtgtct     60
gccggatcag c                                                          71

<210> SEQ ID NO 290
<211> LENGTH: 101
<212> TYPE: DNA
<213> ORGANISM: Artificial Sequence
<220> FEATURE:
<223> OTHER INFORMATION: Amplicon

<400> SEQUENCE: 290
cccacggcct tcaggatggc atccatctgc ttggcatagt ccaggtggcc gctgacctgc     60
aggagacagt gagtgagcac caccgtgggt gtgcagagcc c                        101

<210> SEQ ID NO 291
<211> LENGTH: 87
<212> TYPE: DNA
<213> ORGANISM: Artificial Sequence
<220> FEATURE:
<223> OTHER INFORMATION: Amplicon

<400> SEQUENCE: 291
aacccaccag cctgaactgg actccaagct gctgaagctg ggggatcatc ccgctccggg     60
gcatctctga tgtactgact gagctca                                         87

<210> SEQ ID NO 292
<211> LENGTH: 92
<212> TYPE: DNA
<213> ORGANISM: Artificial Sequence
<220> FEATURE:
<223> OTHER INFORMATION: Amplicon

<400> SEQUENCE: 292
cacaatgctg cctgacatca tggcctctgg cttgcagaat cctaagtcag tgatcttggc     60
acggttctgc ttatccagct gccaacaaag ca                                   92

<210> SEQ ID NO 293
<211> LENGTH: 92
<212> TYPE: DNA
<213> ORGANISM: Artificial Sequence
<220> FEATURE:
<223> OTHER INFORMATION: Amplicon

<400> SEQUENCE: 293
tgacagcttt tggctcagaa attagaaaat gaaatgataa ccaccaacaa agggattctg     60
cagctgagta tggatttcct cccagtgaca gg                                   92

<210> SEQ ID NO 294
<211> LENGTH: 92
```

```
<212> TYPE: DNA
<213> ORGANISM: Artificial Sequence
<220> FEATURE:
<223> OTHER INFORMATION: Amplicon

<400> SEQUENCE: 294
cacgatgagg gttgagggaa aaacagttgg taggaacaag tgcttatcaa actgggaagg     60
tgctcttatt tacagctgct ggctcaagaa tc                                   92

<210> SEQ ID NO 295
<211> LENGTH: 89
<212> TYPE: DNA
<213> ORGANISM: Artificial Sequence
<220> FEATURE:
<223> OTHER INFORMATION: Amplicon

<400> SEQUENCE: 295
gccaggatgc tccatgtagt attgcattat aacatggtct cagctggcct gtgtgtactt     60
ctacaacatg aaccgtcaga ataatcctt                                       89

<210> SEQ ID NO 296
<211> LENGTH: 110
<212> TYPE: DNA
<213> ORGANISM: Artificial Sequence
<220> FEATURE:
<223> OTHER INFORMATION: Amplicon

<400> SEQUENCE: 296
aggtgaaaaa agtacttatg aggatgatga atagttggaa aaactagtaa aatagggttg     60
gttattagaa agaggcatgg gtagttgata gagccataag ctttgatcaa                110

<210> SEQ ID NO 297
<211> LENGTH: 94
<212> TYPE: DNA
<213> ORGANISM: Artificial Sequence
<220> FEATURE:
<223> OTHER INFORMATION: Amplicon

<400> SEQUENCE: 297
aaacaggaga atgaatgaat gaatatgcta atacaaccac ctctgtatcc tctttggtag     60
gcaggaggca agaagcaggc taatctgtct atgg                                 94

<210> SEQ ID NO 298
<211> LENGTH: 91
<212> TYPE: DNA
<213> ORGANISM: Artificial Sequence
<220> FEATURE:
<223> OTHER INFORMATION: Amplicon

<400> SEQUENCE: 298
gccatcctcc tttttctcat cctgtgggc tacttatgat gtgatgccat ttacagtggg      60
ctgggattac aggtgtgagg caccaaaccc a                                    91

<210> SEQ ID NO 299
<211> LENGTH: 94
<212> TYPE: DNA
<213> ORGANISM: Artificial Sequence
<220> FEATURE:
<223> OTHER INFORMATION: Amplicon

<400> SEQUENCE: 299
tggcatgtga gatgtgttca agaaaactcaa gactaaggga atgaatgaat gaatgccacc    60
```

```
<210> SEQ ID NO 300
<211> LENGTH: 101
<212> TYPE: DNA
<213> ORGANISM: Artificial Sequence
<220> FEATURE:
<223> OTHER INFORMATION: Amplicon

<400> SEQUENCE: 300
tccctcaagt ttattcagtc tccttatgta atcagtaatt ctatcaaatc ctcttctttg        60
ctcctgagac ctcacctact tcaatttgga cgtcttgctc t                           101

<210> SEQ ID NO 301
<211> LENGTH: 110
<212> TYPE: DNA
<213> ORGANISM: Artificial Sequence
<220> FEATURE:
<223> OTHER INFORMATION: Amplicon

<400> SEQUENCE: 301
catttccaag tacagtaact ccacagtact atcctgttgc tttacaggga cacctatgcc        60
ttttttcttc agaataaaga acattgcaaa ctgttttgc accactgagg                   110

<210> SEQ ID NO 302
<211> LENGTH: 82
<212> TYPE: DNA
<213> ORGANISM: Artificial Sequence
<220> FEATURE:
<223> OTHER INFORMATION: Amplicon

<400> SEQUENCE: 302
cccaagcacc tgtagcatca tcgtccacgt cctgctgccc actgacctgt ccggctccac        60
acatgaaggc agatgtttga gg                                                 82

<210> SEQ ID NO 303
<211> LENGTH: 102
<212> TYPE: DNA
<213> ORGANISM: Artificial Sequence
<220> FEATURE:
<223> OTHER INFORMATION: Amplicon

<400> SEQUENCE: 303
ggaatgttac cacgttgcta agctatgtaa catatcttaa caaccaggga gccacacagg        60
ctccttggag taagagtgtg agaaactgga tgaagacagc tg                          102

<210> SEQ ID NO 304
<211> LENGTH: 88
<212> TYPE: DNA
<213> ORGANISM: Artificial Sequence
<220> FEATURE:
<223> OTHER INFORMATION: Amplicon

<400> SEQUENCE: 304
tttctgggag ccatctgaat catctttgct gttggctgaa tcactcagag ctgagaggga        60
ggatgaagag gggctatttg attcgctg                                          88

<210> SEQ ID NO 305
<211> LENGTH: 92
<212> TYPE: DNA
<213> ORGANISM: Artificial Sequence
<220> FEATURE:
<223> OTHER INFORMATION: Amplicon
```

(agtgaccttc agtgcctctc tagtggtacc cttt — 94, preceding continuation)

<400> SEQUENCE: 305
ggtatgacct ggacacatta agcattcgta attttccctt ctccattact agatacagtg    60
cttacatttc tcattatttt tatctccctc ct                                  92

<210> SEQ ID NO 306
<211> LENGTH: 78
<212> TYPE: DNA
<213> ORGANISM: Artificial Sequence
<220> FEATURE:
<223> OTHER INFORMATION: Amplicon

<400> SEQUENCE: 306
gcaagccaca ggaagaggaa gcccaaaggc agggagacaa aacagaaata tgcttctggc    60
accaagtcaa attgtaca                                                  78

<210> SEQ ID NO 307
<211> LENGTH: 86
<212> TYPE: DNA
<213> ORGANISM: Artificial Sequence
<220> FEATURE:
<223> OTHER INFORMATION: Amplicon

<400> SEQUENCE: 307
gcggaacaag ccagactgaa aaaaaaaaaa aaaaccctc accgaaatgt gcagcggctc     60
cggagcgaga acagcgctcg aacctc                                         86

<210> SEQ ID NO 308
<211> LENGTH: 101
<212> TYPE: DNA
<213> ORGANISM: Artificial Sequence
<220> FEATURE:
<223> OTHER INFORMATION: Amplicon

<400> SEQUENCE: 308
gttttagaag gaagagggct aggaagaaaa gtggcgcagt acctagtagg taagtataat    60
ctggatgctc ccagtaattc tgagtgttga ctgcacattc t                       101

<210> SEQ ID NO 309
<211> LENGTH: 77
<212> TYPE: DNA
<213> ORGANISM: Artificial Sequence
<220> FEATURE:
<223> OTHER INFORMATION: Amplicon

<400> SEQUENCE: 309
gtataggcag cgacagcact tgtaaattca gcatgagttg catggttggc caatgttggt    60
gagtcctgtg gagatct                                                   77

<210> SEQ ID NO 310
<211> LENGTH: 80
<212> TYPE: DNA
<213> ORGANISM: Artificial Sequence
<220> FEATURE:
<223> OTHER INFORMATION: Amplicon

<400> SEQUENCE: 310
gaaaaccaaa gcaacaaggt gagtcctcag gaggggtcgg agcttgaggt tttggagttt    60
ggaacttact cccatctccc                                                80

<210> SEQ ID NO 311

```
<211> LENGTH: 92
<212> TYPE: DNA
<213> ORGANISM: Artificial Sequence
<220> FEATURE:
<223> OTHER INFORMATION: Amplicon

<400> SEQUENCE: 311
gggttgcagg gatggtgtac aacaggtcct agcatgtata gctgcataga tttcttcacc    60
tgatctttgt gtggaagatc agaatgaatg ca                                  92

<210> SEQ ID NO 312
<211> LENGTH: 95
<212> TYPE: DNA
<213> ORGANISM: Artificial Sequence
<220> FEATURE:
<223> OTHER INFORMATION: Amplicon

<400> SEQUENCE: 312
gggatctgta acttgaccaa ggtcaaagag cttgaaattt caacttggga ccatcagact    60
gaaaacctgc aatctgaaac actttgctgt gctgc                               95

<210> SEQ ID NO 313
<211> LENGTH: 109
<212> TYPE: DNA
<213> ORGANISM: Artificial Sequence
<220> FEATURE:
<223> OTHER INFORMATION: Amplicon

<400> SEQUENCE: 313
gatggtatct cccacaagtc actacttcct gtgttttgc gaaaagctcc ccgtgagggt     60
gggtgccacc ctttctacat ttctccctag ctccttgtgc tgcaaattg               109

<210> SEQ ID NO 314
<211> LENGTH: 87
<212> TYPE: DNA
<213> ORGANISM: Artificial Sequence
<220> FEATURE:
<223> OTHER INFORMATION: Amplicon

<400> SEQUENCE: 314
ctgtctgatt gttaagaggg cttgtattct cttgaaaatc atagtttcta gttggcaagg    60
agcaaactcc caagaacaag ttgtgac                                        87

<210> SEQ ID NO 315
<211> LENGTH: 89
<212> TYPE: DNA
<213> ORGANISM: Artificial Sequence
<220> FEATURE:
<223> OTHER INFORMATION: Amplicon

<400> SEQUENCE: 315
gatagatggc ctggcagtaa gaacaagaca cggaaagctt tacctgcctg attctttcct    60
tccttctttg aagtcagtcc ctagaaggc                                      89

<210> SEQ ID NO 316
<211> LENGTH: 83
<212> TYPE: DNA
<213> ORGANISM: Artificial Sequence
<220> FEATURE:
<223> OTHER INFORMATION: Amplicon

<400> SEQUENCE: 316
tgaacctttg acaccttccc aaaacgctgg gctatttcat catcttctac agtcttcatc    60
```

```
accttcggta atatttgctg tca                                            83
```

<210> SEQ ID NO 317
<211> LENGTH: 90
<212> TYPE: DNA
<213> ORGANISM: Artificial Sequence
<220> FEATURE:
<223> OTHER INFORMATION: Amplicon

<400> SEQUENCE: 317

```
gatctcctct tctgtgccta catcaacttc ccccagcaaa gttagttgta tctttgtcta    60
ctcagtctca tttatgtttt tgtcatcaca                                     90
```

<210> SEQ ID NO 318
<211> LENGTH: 99
<212> TYPE: DNA
<213> ORGANISM: Artificial Sequence
<220> FEATURE:
<223> OTHER INFORMATION: Amplicon

<400> SEQUENCE: 318

```
gttctctctg gccgtcaata tcttaatgaa agtgacattc cgttggccac ggtccactct    60
gtccacgtgg agggccgggt tccagcctct gcagaagtg                           99
```

<210> SEQ ID NO 319
<211> LENGTH: 106
<212> TYPE: DNA
<213> ORGANISM: Artificial Sequence
<220> FEATURE:
<223> OTHER INFORMATION: Amplicon

<400> SEQUENCE: 319

```
gggacctggg tttcctgata cttcctatgt gtcacagttt tcccttaaat gataaccgta    60
catctctgtc ttgccttgtc cttgaattgt ccactcgact ctgggt                  106
```

<210> SEQ ID NO 320
<211> LENGTH: 82
<212> TYPE: DNA
<213> ORGANISM: Artificial Sequence
<220> FEATURE:
<223> OTHER INFORMATION: Amplicon

<400> SEQUENCE: 320

```
tggagagaac cccaggcttt atatgtatac tttgacctca gtgttaattt taaatgctta    60
tgaatcacac acattgcttt ag                                             82
```

<210> SEQ ID NO 321
<211> LENGTH: 103
<212> TYPE: DNA
<213> ORGANISM: Artificial Sequence
<220> FEATURE:
<223> OTHER INFORMATION: Amplicon

<400> SEQUENCE: 321

```
agatgggatc aagggtaaat cagagtaaga ttgatcttga atgagagaag gaatggctgt    60
tgagactgga gggcaggatg gatgtagaga agtttatgtg ccc                     103
```

<210> SEQ ID NO 322
<211> LENGTH: 84
<212> TYPE: DNA
<213> ORGANISM: Artificial Sequence
<220> FEATURE:

```
<223> OTHER INFORMATION: Amplicon
<220> FEATURE:
<221> NAME/KEY: misc_feature
<222> LOCATION: (62)..(62)
<223> OTHER INFORMATION: n is a, c, g, or t

<400> SEQUENCE: 322
tggccatagc agggaataat ttcaatttga aaacaagtgg aatagtgctg tcttccttgg    60
tntgttggtg cacatgtgtc tggt                                          84

<210> SEQ ID NO 323
<211> LENGTH: 99
<212> TYPE: DNA
<213> ORGANISM: Artificial Sequence
<220> FEATURE:
<223> OTHER INFORMATION: Amplicon

<400> SEQUENCE: 323
ggatgggcaa ttttaggtaa tctccaattg acctaactct aatggaatgg gaaagtgaat    60
tactcagcag atgaccacca gggtaggtgc ttaagagat                           99

<210> SEQ ID NO 324
<211> LENGTH: 71
<212> TYPE: DNA
<213> ORGANISM: Artificial Sequence
<220> FEATURE:
<223> OTHER INFORMATION: Amplicon

<400> SEQUENCE: 324
ccagtgcctt gtgcaggatc ttcactagct cctgggcagg gagagggaag aatcttgtga    60
gctcagggag g                                                        71

<210> SEQ ID NO 325
<211> LENGTH: 82
<212> TYPE: DNA
<213> ORGANISM: Artificial Sequence
<220> FEATURE:
<223> OTHER INFORMATION: Amplicon

<400> SEQUENCE: 325
aaatagaata tgagacatga gtaaatatgc cctttttatac aaccagccac atggattctt   60
tgtggcactg actacaactt ga                                            82

<210> SEQ ID NO 326
<211> LENGTH: 95
<212> TYPE: DNA
<213> ORGANISM: Artificial Sequence
<220> FEATURE:
<223> OTHER INFORMATION: Amplicon

<400> SEQUENCE: 326
caaaagctac aagccagaga tacgatacaa caaggacatt gctctgcagg atcaaatgct    60
tgctcagatt tcctggtctc tctgtacata tgtgt                              95

<210> SEQ ID NO 327
<211> LENGTH: 101
<212> TYPE: DNA
<213> ORGANISM: Artificial Sequence
<220> FEATURE:
<223> OTHER INFORMATION: Amplicon

<400> SEQUENCE: 327
aagacaatgt gcagcaaaag atagctccat cataaccacg ttttttatga ttgtcttcac    60
```
agaccgagat aaacgaaaaa ctgcaaatac aggaagaggc c    101

<210> SEQ ID NO 328
<211> LENGTH: 104
<212> TYPE: DNA
<213> ORGANISM: Artificial Sequence
<220> FEATURE:
<223> OTHER INFORMATION: Amplicon

<400> SEQUENCE: 328
caaattttac ccacacagcc tgaaaaatac cttgaaagca aacctcggtc ttctgcatct    60
tccaattgat tcctttacaa actctgcaca catacaactt aagc    104

<210> SEQ ID NO 329
<211> LENGTH: 90
<212> TYPE: DNA
<213> ORGANISM: Artificial Sequence
<220> FEATURE:
<223> OTHER INFORMATION: Amplicon

<400> SEQUENCE: 329
aaaacaagta gggcactgga agaaaaaccc aacacaacag cattaagttt caaacctgca    60
ttccaattag aatcagcagt tgaaagggca    90

<210> SEQ ID NO 330
<211> LENGTH: 74
<212> TYPE: DNA
<213> ORGANISM: Artificial Sequence
<220> FEATURE:
<223> OTHER INFORMATION: Amplicon

<400> SEQUENCE: 330
cattgcagaa ctccagggaa ctcatgaaga gtgcaagggc tggcactccc agccagtctt    60
cccgtcgcag acag    74

<210> SEQ ID NO 331
<211> LENGTH: 100
<212> TYPE: DNA
<213> ORGANISM: Artificial Sequence
<220> FEATURE:
<223> OTHER INFORMATION: Amplicon

<400> SEQUENCE: 331
ccccggcttc ggttctgccg gttacgcttg tttcggttgt ttcggcgatt tgtccgcttc    60
tcggaggggg gcagaagctt ccttgcctcc tccttgtact    100

<210> SEQ ID NO 332
<211> LENGTH: 72
<212> TYPE: DNA
<213> ORGANISM: Artificial Sequence
<220> FEATURE:
<223> OTHER INFORMATION: Amplicon

<400> SEQUENCE: 332
ggaatccagg aggtggtgat gatcaggcag ccaggatttc tgtctccaca gagcatacag    60
tttagttggc tg    72

<210> SEQ ID NO 333
<211> LENGTH: 86
<212> TYPE: DNA
<213> ORGANISM: Artificial Sequence
<220> FEATURE:

<223> OTHER INFORMATION: Amplicon

<400> SEQUENCE: 333

```
aagaaattag aagtggccat ggaagaagaa ggattagcag atgaagaggt aatgtaatta      60
cctataatta ctgtacaaaa gcaccc                                           86
```

<210> SEQ ID NO 334
<211> LENGTH: 96
<212> TYPE: DNA
<213> ORGANISM: Artificial Sequence
<220> FEATURE:
<223> OTHER INFORMATION: Amplicon

<400> SEQUENCE: 334

```
caggtcaatc tactgctaag ggatttcagc ccagcaaatg cacacattaa gaataatgcc      60
agaatgtaga aaagtggctt tatctttcag tagcgg                                96
```

<210> SEQ ID NO 335
<211> LENGTH: 94
<212> TYPE: DNA
<213> ORGANISM: Artificial Sequence
<220> FEATURE:
<223> OTHER INFORMATION: Amplicon

<400> SEQUENCE: 335

```
aggctggtgg aggctagtgc tccgccacag ctgcgggctt taggactcca cctcgtcagt      60
catccatgcc aatggtatgg tttcccaggg tttc                                  94
```

<210> SEQ ID NO 336
<211> LENGTH: 78
<212> TYPE: DNA
<213> ORGANISM: Artificial Sequence
<220> FEATURE:
<223> OTHER INFORMATION: Amplicon

<400> SEQUENCE: 336

```
cttgggatgt tttataagtg tctgtctgta cttcctatga cagccaatca catccaacct      60
atcctcaggt cccttccc                                                    78
```

<210> SEQ ID NO 337
<211> LENGTH: 87
<212> TYPE: DNA
<213> ORGANISM: Artificial Sequence
<220> FEATURE:
<223> OTHER INFORMATION: Amplicon

<400> SEQUENCE: 337

```
ttgacatgag gccatttgct atcataagcc atcactagga acttctagtc tgtctcactc      60
gattgaggct acaatgttgt taggtgc                                          87
```

<210> SEQ ID NO 338
<211> LENGTH: 91
<212> TYPE: DNA
<213> ORGANISM: Artificial Sequence
<220> FEATURE:
<223> OTHER INFORMATION: Amplicon

<400> SEQUENCE: 338

```
agatctggga caaggtctgt gtccctaaga catttctcag agtggtttga gccagcagaa      60
atgttgcttg atggacatcg ttgacattag c                                     91
```

-continued

```
<210> SEQ ID NO 339
<211> LENGTH: 81
<212> TYPE: DNA
<213> ORGANISM: Artificial Sequence
<220> FEATURE:
<223> OTHER INFORMATION: Amplicon'

<400> SEQUENCE: 339
acttctccag ttgaaagggt atccatttga gaaacactgc actgatctgg aatatagtgt      60
cattcatgag tctccattac c                                                81

<210> SEQ ID NO 340
<211> LENGTH: 90
<212> TYPE: DNA
<213> ORGANISM: Artificial Sequence
<220> FEATURE:
<223> OTHER INFORMATION: Amplicon

<400> SEQUENCE: 340
gcctagaata tcctgcagtg gtagagtttg ctccattcca gaagatagcc aaaaagaagc      60
tgagaaaaaa agatgccaag actggaagca                                       90

<210> SEQ ID NO 341
<211> LENGTH: 72
<212> TYPE: DNA
<213> ORGANISM: Artificial Sequence
<220> FEATURE:
<223> OTHER INFORMATION: Amplicon

<400> SEQUENCE: 341
ggaggaaggc cagcagaagc aggattggtt gcatcttctc aggaaggctg ccctggttgg      60
agctgctgtt gt                                                          72

<210> SEQ ID NO 342
<211> LENGTH: 75
<212> TYPE: DNA
<213> ORGANISM: Artificial Sequence
<220> FEATURE:
<223> OTHER INFORMATION: Amplicon

<400> SEQUENCE: 342
cagccttttc accaaccttc aaaaagtttt cgtaattgat catcgcttcc tctccaatca      60
taggtggtgt ctggt                                                       75

<210> SEQ ID NO 343
<211> LENGTH: 98
<212> TYPE: DNA
<213> ORGANISM: Artificial Sequence
<220> FEATURE:
<223> OTHER INFORMATION: Amplicon

<400> SEQUENCE: 343
gataggcgca ccaggaatga ccgccatata cttccctaaa gctcaaccca cccaccagtt      60
cagttaagaa ttatacttta attcgtgttt ggccactg                              98

<210> SEQ ID NO 344
<211> LENGTH: 110
<212> TYPE: DNA
<213> ORGANISM: Artificial Sequence
<220> FEATURE:
<223> OTHER INFORMATION: Amplicon

<400> SEQUENCE: 344
```

```
catccactca ccactgtatc catccacctc tcctcccttt gttttccccta caagccccac    60 gtcctggggg gctgactcca actggggtg ctgcttccaa gcctcatgcc                110
```

<210> SEQ ID NO 345
<211> LENGTH: 84
<212> TYPE: DNA
<213> ORGANISM: Artificial Sequence
<220> FEATURE:
<223> OTHER INFORMATION: Amplicon

<400> SEQUENCE: 345

```
gagcacccac tgtgtacgag tacacaaagt gaccacgtgg ctcagcactg tatacaaata    60
agtatggcat aattctgctg gtgt                                            84
```

<210> SEQ ID NO 346
<211> LENGTH: 91
<212> TYPE: DNA
<213> ORGANISM: Artificial Sequence
<220> FEATURE:
<223> OTHER INFORMATION: Amplicon

<400> SEQUENCE: 346

```
gggatggatt taccagaaag atgatcagct tataattcag agaggtgacg tatcctataa    60
tattgaccac tcatgaaatg cttggtcagc t                                    91
```

<210> SEQ ID NO 347
<211> LENGTH: 106
<212> TYPE: DNA
<213> ORGANISM: Artificial Sequence
<220> FEATURE:
<223> OTHER INFORMATION: Amplicon

<400> SEQUENCE: 347

```
actcaggctt accatatttg tttgtacttc ttttattcac ttcaggagac actgggcctt    60
ggttttccaa atagggtttt tgacctggga tttcctttgc catgca                   106
```

<210> SEQ ID NO 348
<211> LENGTH: 104
<212> TYPE: DNA
<213> ORGANISM: Artificial Sequence
<220> FEATURE:
<223> OTHER INFORMATION: Amplicon

<400> SEQUENCE: 348

```
aggtgataaa tagcttacat tttagagttt gctttctgtt ataaaagttg tacgcattga    60
tataaaattt gtaaagccca cagtggcatc acgttcaggt atgg                    104
```

<210> SEQ ID NO 349
<211> LENGTH: 81
<212> TYPE: DNA
<213> ORGANISM: Artificial Sequence
<220> FEATURE:
<223> OTHER INFORMATION: Amplicon

<400> SEQUENCE: 349

```
tgatggtttt ctggtgtccc tttaggtccc agccagtact gagagtcaag gcaatcatgg    60
agttcaatcc cagggaagtg g                                               81
```

<210> SEQ ID NO 350
<211> LENGTH: 79
<212> TYPE: DNA
<213> ORGANISM: Artificial Sequence
<220> FEATURE:
<223> OTHER INFORMATION: Amplicon

<400> SEQUENCE: 350
gcccaagagc ctgagttctc ctgagacgga cacaggagga catggtgaga tgagaagctc    60
ctcttcatcg atggcccgg                                                 79

<210> SEQ ID NO 351
<211> LENGTH: 75
<212> TYPE: DNA
<213> ORGANISM: Artificial Sequence
<220> FEATURE:
<223> OTHER INFORMATION: Amplicon

<400> SEQUENCE: 351
ccatcgtaag gcttggaatc gaatgaaaat aaccaatgag cagttgcagg cagattacct    60
tgctgggaag tagcc                                                     75

<210> SEQ ID NO 352
<211> LENGTH: 109
<212> TYPE: DNA
<213> ORGANISM: Artificial Sequence
<220> FEATURE:
<223> OTHER INFORMATION: Amplicon
<220> FEATURE:
<221> NAME/KEY: misc_feature
<222> LOCATION: (21)..(21)
<223> OTHER INFORMATION: n is a, c, g, or t

<400> SEQUENCE: 352
ggtccagccc ttctcaacac nggaaagccc ttgagccatc tttgatttgt gtgttttgat    60
ctaattgcac tactgcttgc aatgcttgtt tttagcggtg agtgctggt               109

<210> SEQ ID NO 353
<211> LENGTH: 80
<212> TYPE: DNA
<213> ORGANISM: Artificial Sequence
<220> FEATURE:
<223> OTHER INFORMATION: Amplicon

<400> SEQUENCE: 353
tcctggtagg gatacagctc attcgtcaag ttctgttcgg caatgaccat cctttggtac    60
agtgtccctg caaaccagac                                                80

<210> SEQ ID NO 354
<211> LENGTH: 81
<212> TYPE: DNA
<213> ORGANISM: Artificial Sequence
<220> FEATURE:
<223> OTHER INFORMATION: Amplicon

<400> SEQUENCE: 354
ggcagccgat ggtcagtact tccttcctct tgggcatgtc tttcctccgt gcacagagta    60
tttactgttc tgcccaaggc c                                              81

<210> SEQ ID NO 355
<211> LENGTH: 77
<212> TYPE: DNA
<213> ORGANISM: Artificial Sequence
<220> FEATURE:
<223> OTHER INFORMATION: Amplicon

<400> SEQUENCE: 355

```
ccctctgctg gcacctttaa ggtgggctg tgctttgttt cttcaaggct cctatctggt    60
ctcagtccca cctgggc                                                  77

<210> SEQ ID NO 356
<211> LENGTH: 97
<212> TYPE: DNA
<213> ORGANISM: Artificial Sequence
<220> FEATURE:
<223> OTHER INFORMATION: Amplicon

<400> SEQUENCE: 356
gcttagagcc tccatttctt tcctcatctg ggcaatcgcg tttcgcaagc tcgtgttctg    60
ctctcggagc cgctggatct cactggatgg aaagtct                            97

<210> SEQ ID NO 357
<211> LENGTH: 93
<212> TYPE: DNA
<213> ORGANISM: Artificial Sequence
<220> FEATURE:
<223> OTHER INFORMATION: Amplicon

<400> SEQUENCE: 357
gattgacaaa tttcgtgacc cacaaatgtg ttttgacatc tgcagttgtc agtttgtctg    60
tcattactca tttgagtctt atgagcaggc tga                                93

<210> SEQ ID NO 358
<211> LENGTH: 93
<212> TYPE: DNA
<213> ORGANISM: Artificial Sequence
<220> FEATURE:
<223> OTHER INFORMATION: Amplicon

<400> SEQUENCE: 358
gattgacaaa tttcgtgacc cacaaatgtg ttttgacatc tgcagttgtc agtttgtctg    60
tcattactca tttgagtctt atgagcaggc tga                                93

<210> SEQ ID NO 359
<211> LENGTH: 99
<212> TYPE: DNA
<213> ORGANISM: Artificial Sequence
<220> FEATURE:
<223> OTHER INFORMATION: Amplicon

<400> SEQUENCE: 359
tgctgtcctt actcattcca catccttact agaggtgagg ggttggggga ggggtggtcg    60
agcaatcttt tgtactttg agggtctgca aacttaggc                           99

<210> SEQ ID NO 360
<211> LENGTH: 78
<212> TYPE: DNA
<213> ORGANISM: Artificial Sequence
<220> FEATURE:
<223> OTHER INFORMATION: Amplicon

<400> SEQUENCE: 360
gtggtccata tggtcccttc ttaaagaaga tgggtgttct caccactatt tacagccaag    60
aaccggaaga gtcccttt                                                 78

<210> SEQ ID NO 361
<211> LENGTH: 74
<212> TYPE: DNA
<213> ORGANISM: Artificial Sequence
```

```
<220> FEATURE:
<223> OTHER INFORMATION: Amplicon

<400> SEQUENCE: 361
ccgttcgacc cttgatgctg gggcatccgg gttgggatgg agataggagg atctcagtat     60
atttgtttcg tagt                                                      74

<210> SEQ ID NO 362
<211> LENGTH: 89
<212> TYPE: DNA
<213> ORGANISM: Artificial Sequence
<220> FEATURE:
<223> OTHER INFORMATION: Amplicon

<400> SEQUENCE: 362
ggtgactcac tgggcagatt ctcctggtgg agtcccttct gtcctggctg tagctttgta     60
cttaggccat ttctttgctg taggcactc                                      89

<210> SEQ ID NO 363
<211> LENGTH: 80
<212> TYPE: DNA
<213> ORGANISM: Artificial Sequence
<220> FEATURE:
<223> OTHER INFORMATION: Amplicon

<400> SEQUENCE: 363
gctctgccga tgtcctcagg gctgggctgg cccacactgc cgcatggctc tgtgtcctga     60
gaactgcaat gcccacactg                                                80

<210> SEQ ID NO 364
<211> LENGTH: 100
<212> TYPE: DNA
<213> ORGANISM: Artificial Sequence
<220> FEATURE:
<223> OTHER INFORMATION: Amplicon

<400> SEQUENCE: 364
cagtactggt gagggaaatc tgttctcaag tcctacagtg cattcatgtg tcctgaagtc     60
cagaattctg taggatagtg tcctacgtta taagcctgga                         100

<210> SEQ ID NO 365
<211> LENGTH: 97
<212> TYPE: DNA
<213> ORGANISM: Artificial Sequence
<220> FEATURE:
<223> OTHER INFORMATION: Amplicon

<400> SEQUENCE: 365
ccacttccct caatcatgtg acaccacttc agtgaagcca cctttaaatc atctgttttt     60
gaatttgtct ggaatccaga aaagttggc aaaaccc                              97

<210> SEQ ID NO 366
<211> LENGTH: 85
<212> TYPE: DNA
<213> ORGANISM: Artificial Sequence
<220> FEATURE:
<223> OTHER INFORMATION: Amplicon

<400> SEQUENCE: 366
gtgcgaaggt tagtttctga ggaaggaaaa aagttgatga tgatgcccat tgtcaggtct     60
gtaactaact tgctgggttc ctctc                                          85
```

-continued

<210> SEQ ID NO 367
<211> LENGTH: 83
<212> TYPE: DNA
<213> ORGANISM: Artificial Sequence
<220> FEATURE:
<223> OTHER INFORMATION: Amplicon

<400> SEQUENCE: 367
cccatgggag atgctcttga gaaagactat tctggtggtg ggtgcgggat cctgtcaggg    60
ggaagagatg gaaccaggag acc    83

<210> SEQ ID NO 368
<211> LENGTH: 94
<212> TYPE: DNA
<213> ORGANISM: Artificial Sequence
<220> FEATURE:
<223> OTHER INFORMATION: Amplicon

<400> SEQUENCE: 368
gccctgtccc tgcttctgga aaagaatttt cgacatctg cacacagaca gttgtgaaaa    60
aggaggagaa gcagctactg gctaaggggc acct    94

<210> SEQ ID NO 369
<211> LENGTH: 86
<212> TYPE: DNA
<213> ORGANISM: Artificial Sequence
<220> FEATURE:
<223> OTHER INFORMATION: Amplicon

<400> SEQUENCE: 369
caggcagctt cttggtcaga cagaccatct ggccctggcg taccacagca caccacaggc    60
gagcacagac atccatgccg ggacac    86

<210> SEQ ID NO 370
<211> LENGTH: 103
<212> TYPE: DNA
<213> ORGANISM: Artificial Sequence
<220> FEATURE:
<223> OTHER INFORMATION: Amplicon

<400> SEQUENCE: 370
agcatcctat gcctttgaca aagattgcag tggcccctcg agtgcagagg tcatcccagg    60
tgttgctgag tttattgagc acacctagcc tgcttgctta ctg    103

<210> SEQ ID NO 371
<211> LENGTH: 94
<212> TYPE: DNA
<213> ORGANISM: Artificial Sequence
<220> FEATURE:
<223> OTHER INFORMATION: Amplicon

<400> SEQUENCE: 371
gttctgattt ctactcctcc acacataaga cgtaataacc agtcatcaca attcacgcca    60
tagtgtttga gatgcaaatg caaagactga ttcc    94

<210> SEQ ID NO 372
<211> LENGTH: 88
<212> TYPE: DNA
<213> ORGANISM: Artificial Sequence
<220> FEATURE:
<223> OTHER INFORMATION: Amplicon

<400> SEQUENCE: 372

```
ctgatgtgtc ttggcaggtc atccctggcc tgcttaggca actttggctg gtgaatggcc    60
actgggcttt cgacgtcctg atccatgg                                       88

<210> SEQ ID NO 373
<211> LENGTH: 96
<212> TYPE: DNA
<213> ORGANISM: Artificial Sequence
<220> FEATURE:
<223> OTHER INFORMATION: Amplicon

<400> SEQUENCE: 373
ccttacccat cccaactagc cttacccatc ctcgcctctc tcctcagccc agaccagaag    60
agttccacca gcgatccaac gtcacactca ctctac                              96

<210> SEQ ID NO 374
<211> LENGTH: 81
<212> TYPE: DNA
<213> ORGANISM: Artificial Sequence
<220> FEATURE:
<223> OTHER INFORMATION: Amplicon

<400> SEQUENCE: 374
cctcctgatc atactctggt acctggcctg tgcatcggcc tcctgcttca tgtcaacctc    60
ctactcctgc cagggaatgt g                                              81

<210> SEQ ID NO 375
<211> LENGTH: 93
<212> TYPE: DNA
<213> ORGANISM: Artificial Sequence
<220> FEATURE:
<223> OTHER INFORMATION: Amplicon
<220> FEATURE:
<221> NAME/KEY: misc_feature
<222> LOCATION: (65)..(65)
<223> OTHER INFORMATION: n is a, c, g, or t

<400> SEQUENCE: 375
cacatgaggc tttcggagga ataaattggt ctgaaatcga ggctgctggc ttttgtgtta    60
ataantgtgt aaaagctatc cagggcatca agg                                 93

<210> SEQ ID NO 376
<211> LENGTH: 95
<212> TYPE: DNA
<213> ORGANISM: Artificial Sequence
<220> FEATURE:
<223> OTHER INFORMATION: Amplicon

<400> SEQUENCE: 376
ccatccctct ccacagcaag gatgacgtgg aacgctgcaa gcagaaggac ctactggagc    60
agatgatggc cgagatgatt ggcgagttcc cagac                               95

<210> SEQ ID NO 377
<211> LENGTH: 77
<212> TYPE: DNA
<213> ORGANISM: Artificial Sequence
<220> FEATURE:
<223> OTHER INFORMATION: Amplicon

<400> SEQUENCE: 377
ggaaattgtc aggtcagctc agtgcctaca ggcccattaa atttatgtct ccttcttctg    60
agaggacatg aaatggg                                                   77
```

```
<210> SEQ ID NO 378
<211> LENGTH: 100
<212> TYPE: DNA
<213> ORGANISM: Artificial Sequence
<220> FEATURE:
<223> OTHER INFORMATION: Amplicon
<220> FEATURE:
<221> NAME/KEY: misc_feature
<222> LOCATION: (74)..(74)
<223> OTHER INFORMATION: n is a, c, g, or t

<400> SEQUENCE: 378
tgctttaggc aggtgtgaac tccagcccaa atgccagtca aagtcaaggc atgggttttc    60
ctagcctatc ttanaggaaa ttcctgtacc ttcttggccc                          100

<210> SEQ ID NO 379
<211> LENGTH: 77
<212> TYPE: DNA
<213> ORGANISM: Artificial Sequence
<220> FEATURE:
<223> OTHER INFORMATION: Amplicon

<400> SEQUENCE: 379
ccccatggtc aacacaaaat gtagactctg aaatgatgtc taatccgcca gtgagagcaa    60
cagcctctgg ggtgatg                                                   77

<210> SEQ ID NO 380
<211> LENGTH: 80
<212> TYPE: DNA
<213> ORGANISM: Artificial Sequence
<220> FEATURE:
<223> OTHER INFORMATION: Amplicon

<400> SEQUENCE: 380
ggtcagaaag ttaccaggac ttgtcttgat accttattct gggtgaggaa ggtcttattt    60
ttgtccactg cagacactgg                                                80

<210> SEQ ID NO 381
<211> LENGTH: 110
<212> TYPE: DNA
<213> ORGANISM: Artificial Sequence
<220> FEATURE:
<223> OTHER INFORMATION: Amplicon

<400> SEQUENCE: 381
gtgatctgaa tgatgttgaa caagcattat caaagaattc cacgatgaga agcaaaggga    60
ggagagtgga acttttgaaa acctgtattt cattgtctgg ctatccgtgt              110

<210> SEQ ID NO 382
<211> LENGTH: 102
<212> TYPE: DNA
<213> ORGANISM: Artificial Sequence
<220> FEATURE:
<223> OTHER INFORMATION: Amplicon

<400> SEQUENCE: 382
tcctgcaaaa tgacttgagt tggtaaagta gaaagtttta tgactacaaa tttcagggcc    60
aagtagtaaa gacctgctac aaaataaaaa ggcctgacat gt                      102

<210> SEQ ID NO 383
<211> LENGTH: 106
<212> TYPE: DNA
<213> ORGANISM: Artificial Sequence
```

```
<220> FEATURE:
<223> OTHER INFORMATION: Amplicon

<400> SEQUENCE: 383
cttccaggga aattcacctc ttctatagaa gagtttgttt tgaactatac gatttgaaac       60
aaaattcttt ttttggagac tatggaaaca ttctcaacag ggaaac                    106

<210> SEQ ID NO 384
<211> LENGTH: 76
<212> TYPE: DNA
<213> ORGANISM: Artificial Sequence
<220> FEATURE:
<223> OTHER INFORMATION: Amplicon

<400> SEQUENCE: 384
gaaagggaag agcacacagt ctgtgttaag aggtggtcca gcaatatcgg cagggcttgt       60
gtgggacttt gaggcc                                                      76
```

KARYOTYPING ASSAY

CROSS-REFERENCE TO RELATED APPLICATIONS

This application claims the benefit of priority under 35 U.S.C. §119(e) to U.S. Provisional Patent Application No. 61/334,658, filed May 14, 2010, which is herein incorporated by reference in its entirety.

FIELD

This disclosure relates to methods and kits for karyotyping in which at least one chromosome is interrogated by amplifying one or more loci that are not within copy number variable regions (CNVR) thereof.

BACKGROUND INFORMATION

The human haploid genome is a deoxyribonucleic acid (DNA) sequence and consists of approximately three billion base pairs grouped into 23 chromosomes. However, the human genome is diploid and consists of approximately six billion base pairs grouped into 46 chromosomes. Hence, two copies of each genomic segment and two copies of each chromosome are represented in most of the human genome. The exception is the male human, which has only one copy each of chromosome X and chromosome Y. Nevertheless, variable copy numbers (i.e. not two copies) of genomic segments and chromosomes are observed in individual genomic DNA (gDNA) samples. Such copy number variable regions (CNVR) that are typically greater than one kilobase in length and generally occur at a minor frequency of equal to or greater than 1% in the population are termed "copy number variants" (CNVs; see, e.g., Feuk, et al. Nat. Rev. Genet. 7:85-97 (2006)). Copy number variation (CNV) and its mechanisms of formation, associations with phenotype, and methods of analysis have been extensively reviewed (Feuk, supra; Freeman, et al. Genome Res. 16:949-961 (2006); Sharp, et al. Annu. Rev. Genomics Hum. Genet. 7:407-442 (2006); Nature Genetics 39:S1-S54 (2007), entire issue). Currently, approximately 8600 CNVs have been identified and cover about 5-10% of the human genome (Redon, et al. Nature 444:444-454 (2006); Conrad, et al. Nature 464:704-712 (2010)). Continuing studies toward finer mapping of the CNV map and interrogating more diverse gDNA samples are tracked at the Database of Genomic Variants (http://projects.tcag.ca/variation/). Aberrations in the normal complement of 46 human chromosomes have been identified by cytogenetic analysis. Cytogenetics and its history, linking of chromosomal defects and disease, and methods of analysis have been extensively reviewed (Speicher, et al. Nat. Rev. Genet. 6:782-792 (2005); Trask, Nat. Rev. Genet. 3:769-778 (2002)). More recently, polymerase chain reaction (PCR)-based assays have been used to identify such aberrations.

There is a need in the art for methods that provide fast, accurate, easy-to-use and reliable karyotype information. Karyotype includes an analysis of chromosome number, type, shape, and banding. Currently available methods for determining karyotype and chromosome number lack accuracy due to the presence of CNVRs, are labor-intensive and do not provide for simultaneous interrogation of multiple chromosomes without requiring multiple reporting labels. Unless chromosomes are interrogated outside of CNVRs, an inaccurate karyotype or chromosome number determination may result. Accordingly, this disclosure provides such methods by using as target sequences only those targets known to be outside of CNVRs. In addition, the methods described herein provide for simultaneous interrogation of multiple chromosomes using a single, or multiple reporting labels. Using these methods, karyotypes may be rapidly and accurately determined. These and other advantages may be drawn from the description provided below.

Figure 1:
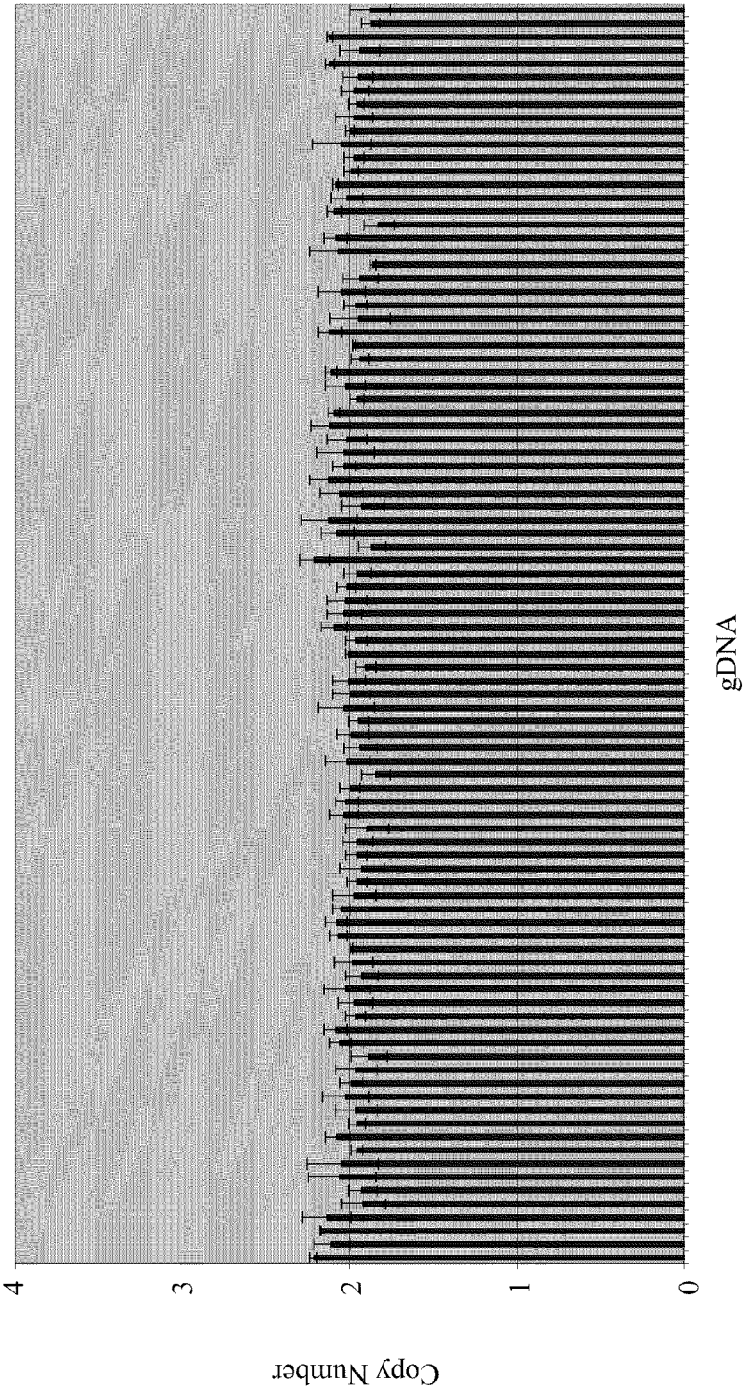
FIG. 1. Results of exemplary assay of chromosome 2.

For FIGS. 1-8, the genomic DNA (gDNA) samples on the x-axis from left-to-right are as follows:
NA 10859_1, NA10859_2, NA 10859_3, NA 10859_4, NA 14474, NA 14476, NA 17102, NA 17103, NA 17104, NA 17105, NA 17106, NA 17107, NA 17108, NA 17109, NA 17110, NA 17111, NA 17112, NA 17113, NA 17114, NA 17115, NA 17116, NA 17117, NA 17118, NA 17119, NA 17120, NA 17121, NA 17122M NA 17123, NA 17124, NA 17125, NA 17126, NA 17127, NA 17128, NA 17129, NA 17130, NA 17131, NA 17132, NA 17134, NA 17136, NA 17137, NA 17139, NA 17140, NA 17144, NA 17147, NA 17148, NA 17149, NA 17155, NA 17188, NA 17194, NA 17201, NA 17202, NA 17203, NA 17204, NA 17205, NA 17206, NA 17207, NA 17208, NA 17209, NA 17210, NA 17211, NA 17212, NA 17213, NA 17214, NA 17215, NA 17216, NA 17217, NA 17220, NA 17221, NA 17223, NA 17225, NA 17226, NA 17227, NA 17228, NA 17230, NA 17231, NA 17232, NA 17235, NA 17237, NA 17239, NA 17240, NA 17241, NA 17242, NA 17245, NA 17247, NA 17251, NA 17253, NA 17254, NA 17255, NA 17258, NA 17259, NA 17260, NA 17261, NA 17262, NA 17263.

SUMMARY

Disclosed herein are methods for karyotype analysis and for determining the copy number of a test locus on a chromosome in a test biological sample, the test locus being located outside of a copy number variable region (CNVR) of the chromosome, by amplifying a nucleic acid sequence corresponding to the test locus to produce an amplification product, or amplicon, and quantifying the relative copy number of the chromosome in the test biological sample relative to a control biological sample. Karyotyping methods are also provided here that do not require comparison to a reference assay or reference sample. Such methods include those using virtual reference assays or virtual calibrator samples.

Embodiments of the methods disclosed herein can be performed on one or multiple samples with or without a calibrator sample or reference assay. In other embodiments, the target copy number assays can serve as the copy number reference assay herein denoted as a "virtual copy number reference assay".

Variations of these methods, as well as reagents, kits, arrays and devices for carrying out the same are also provided.

DETAILED DESCRIPTION

This disclosure relates to methods for measuring the copy number of one, more than one, or all chromosomes of a genome using real-time amplification methods (i.e., "karyotyping"). The term "karyotype" refers to the interrogation of one, more than one, or all chromosomes of a particular biological sample, such as a nucleic acid preparation including, but not limited to, deoxyribonucleic acid (DNA, including but not limited to, genomic (gDNA) and mitochondrial DNA (mtDNA)), ribonucleic acid (RNA), proteins, cells, tissues, and organisms.

To "interrogate" one or more chromosomes means to perform an assay, including the methods described herein, to obtain information about the one or more chromosomes contained in the sample. Typically, information relating to "copy number" (CN) is desired. The term copy number generally refers to the number of amplicons resulting from polymerase chain reaction (PCR) amplification, the number of genes or regions on a chromosome, the number of chromosomes in a genome, and the like. The term "amplicon" refers to a piece of DNA formed as the product of an amplification reaction, such as PCR, ligase chain reaction (LCR) or natural gene duplication. The skilled artisan will understand that, within this disclosure, any such molecules can be referred to as target or reference loci depending on the particular assay system. For example, a genome can be queried using as the biological sample a gDNA that preferably, but not necessarily, contains at least one of each chromosome that the user desires to interrogate. In some embodiments, the gDNA sample can contain a pair of each of chromosomes 1-22 and either two X chromosomes, or an X and a Y chromosome. However, it is understood that variations and abnormalities occur such that the number or composition of chromosomes among gDNA samples can vary. In fact, the methods described herein are directed to detecting such variations and abnormalities. In addition, the user may desire to interrogate only a subset of chromosomes (i.e., one or more) present in a genome and it is therefore necessary that only those chromosomes of interest be present. Furthermore, the interrogation typically includes a reference locus (i.e., a "reference locus" or "endogenous control") which is a locus different from the test locus and is not found within a CNVR. The copy number of the reference locus is typically, but not necessarily, known. A reference locus can reside on a chromosome of interest or on another chromosome and can be interrogated to normalize sample input or to determine relative copy number (i.e., an "endogenous control").

The methods and assays described herein, which include the determination of the copy number of target loci, are referred to herein as "copy number assays". The methods and assays described herein for interrogating reference loci are referred to herein as "copy number reference assays". Typically, the reference locus is present in all samples and is used to normalize for sample input variation and determine relative copy number. However, the test locus can be present or absent. For example, a Y chromosome test assay may interrogate as "present" in a normal male sample, but "absent" in a normal female sample. Existing assay systems, such as the TaqMan® Copy Number Assays (Applied Biosystems), have been used in some instances to interrogate target and reference loci. However, interrogation of test loci within copy number variable regions (CNVRs) has been found to lead to inaccurate karyotype determinations.

An important feature of the methods described herein is that the test loci are outside of (i.e., not within) CNVRs. As described herein, a CNVR includes, but is not limited to, any type of structural variation of a target locus that can affect copy number determination including, but not limited to, duplications, deletions, insertions, repeats, substitutions, and the like. Certain variations can imitate or mimic changes in chromosomal copy number or detrimentally affect the assay by making it less reliable or accurate. Typically, a "universal" set of karyotyping assays (i.e., applicable to all samples or persons) will not target CNVRs. However, it is important to note that CNVRs may vary between individuals or populations of individuals. For instance, a duplication observed in an individual or population of individuals may not be observed in another individual or population of individuals. As such, the methods described herein may target loci that are within a CNVR in one individual or population of individuals but not within a CNVR or another individual or population of individuals.

The difference in copy number between samples is typically determined by "relative quantitation". Relative quantitation is used to report the copy number of a target locus or chromosome on which the target locus is found in a test sample (i.e., "test locus" or "unknown locus") relative to one or more reference loci or "calibrator samples". With reference to the use of a calibrator sample, the term "relative to" means compared to the copy number of a target locus or chromosome on which the target locus is found in a calibrator sample. A "calibrator sample" is a biological sample, often of known karyotype (i.e., a "control gDNA"), that is interrogated before, after or simultaneously with the test sample. The number of copies in the test sample can then be determined relative to the calibrator sample. One or more reference loci or calibrator samples can be used as desired by the user. The one or more reference loci can be the same or different and can be present in the test sample(s) or calibrator sample(s). Typically, the measure of relative quantitation is reported using the term "fold change", which refers to the amount of amplified product (which relates to the copy number) in a test sample relative to a reference or calibrator sample. Fold change can be quantified using any of several available methods, including but not limited to those described by Livak, et al. (Methods, 25:402-408 (2001)) or commercially available products such as CopyCaller™ (Applied Biosystems, see below). The methods described herein can be performed on one or more than one sample with or without a calibrator sample or reference assay. Various embodiments of such methods are described herein.

The real-time polymerase chain reaction (RT-PCR) is a conventional tool which can be used to amplify and quantify a target nucleic acid molecule, including but not limited to, DNA and RNA, in a sample. The amount of target nucleic acid can be determined as an absolute copy number or as a relative amount. Specifically, the use of RT-PCR to quantify gene expression using the comparative $C_T$-method is known to one of skill in the art (Livak, et al. (supra)). In general, the threshold cycle ($C_T$) for a given genetic locus can be determined by arbitrarily setting a signal intensity threshold that falls within the linear range of amplification of real-time PCR data. Previous application of this calculation has been used, for example, to normalize the amplification product of a target gene to the amplification product of an endogenous control gene and then to normalize the data to a calibrator sample, such as an untreated reference sample, to determine the expression of the target gene.

Certain currently available assay systems, such as PCR-based TaqMan® systems, can be useful for relative quantification of nucleic acids amplified from a biological sample to determine gene or chromosome copy number (see, e.g., the TaqMan® assays described in the following Applied Biosystems publications: "Product Bulletin: TaqMan® Copy Number Assays and Custom TaqMan® Copy Number Assays", "Protocol: TaqMan® Copy Number Assays" (PN 4397425 Rev. C), "Quick Reference Card: TaqMan® Copy Number Assays" (PN 4397424 Rev. B)). The TaqMan® Copy Number Assay and the TaqMan® Copy Number Reference Assay have been used in tandem to interrogate chromosomes to amplify target and control loci, respectively. Usually, the assays are carried out as a single step, "two-plex" real-time PCR assay (i.e., two separate assays within the same reaction well or container). In this type of assay, target and control loci are detected using differently labeled probes. Often, the sample interrogated by such PCR-based assays is human genomic DNA (gDNA) and, typically a minimum of two human gDNA samples are interrogated, including a test and a calibrator sample. Currently, the TaqMan® Copy Number Assay interrogates test loci, which are located throughout the genome and may reside within a copy number variable region (CNVR) and provides copy number variation (CNV) information. The TaqMan® Copy Number Reference Assay interrogates one or more reference loci which, as defined above, are found outside of CNVRs (e.g., Ribonuclease P RNA component H1 (H1RNA) gene (RPPH1) on chromosome 14, cytoband 14q11.2, also known as "RNase P", and the telomerase reverse transcriptase (TERT) gene located on chromosome 5, cytoband 5p15.33). The TaqMan® Copy Number Reference Assay thereby serves as the endogenous control by interrogating a non-CNVR sequence of interest to normalize for sample input variation by relative quantification (RQ). For example, the TaqMan® Copy Number Assay can utilize an FAM™ dye-labeled minor groove binder (MGB) probe and unlabeled PCR primers directed at the one or more test loci in the test sample or calibrator sample, which are typically assayed separately. The TaqMan® Copy Number Reference Assay can use VIC dye-labeled TAMRA™ probes directed at the one or more reference loci. By comparing the products of these reactions, the user normalizes for sample amount and determines the relative number of copies of the target loci in the sample. However, as described above, interrogation of test loci within copy number variable regions (CNVRs) has been found to lead to inaccurate karyotype determinations. Thus, it is important that the target loci are found outside of (e.g., not within) CNVRs.

The methods described herein can utilize a copy number reference assay. In certain embodiments, the target loci in the test and calibrator sample(s) of, for example, gDNA, can be the same or different. In certain embodimetns, the reference assay is used to normalize for sample input variation between samples (i.e., between multiple test samples or between the test and calibrator samples). Thus, in such assays, one or more reference loci can be amplified from the test or control samples and the copy number (i.e., fold change) is calculated as described herein as a copy number reference assay. Variations of such embodiments are also contemplated as would be understood by one of skill in the art.

The methods described herein can also be conducted using a calibrator sample that, as described above, is typically a biological sample of known karyotype, while the karyotype of the test sample is unknown. The relative difference in copy number between the calibrator sample and the test sample can be calculated as is known in the art or described herein. Typically, the "test assay" and "calibrator assay" (i.e., reference or endogenous control assay) are both used for relative quantification of all samples in order to normalize for sample input variation between samples prior to comparing the different samples themselves. The copy number of the target loci of the test samples is calculated by dividing the fold change of the target copy number in the test sample by that of the calibrator sample and then multiplying by the target copy number of the calibrator sample. This calculation is used in the analysis of the currently and commercially available TaqMan® assay systems and similar systems. The test and calibrator assays are, at least in part, directed to the same target loci, but the target loci can also be different. In some embodiments, the methods can include amplifying a target locus from outside (i.e., not within) a CNVR from a test biological sample (such as a gDNA sample in which the number of copies of a particular chromosome is not known), amplifying the same target loci from a calibrator biological sample, and calculating the copy number of the target loci in the test sample relative to the control sample. Variations of such embodiments, including those that do not use a reference assay or calibrator sample, are also contemplated as would be understood by one of skill in the art.

As discussed above, many embodiments of the methods described herein are contemplated as would be understood by one of skill in the art. Exemplary assay formats using reference or calibrator samples are illustrated in Table 1 and described below.

TABLE 1

Exemplary Karyotyping Assay Design Formats when an Unknown Sample is Tested Relative to a Calibrator Sample

| | | | | | Reaction #1 | | Reaction #2 | |
| --- | --- | --- | --- | --- | --- | --- | --- | --- |
| Format No. | No. CN Assays | No. CN Reference Assays | No. Reactions (per sample) | Plexy Per Reaction | Detectable Label (CN Assay) | Detectable Label (CN Ref. Assay) | Detectable Label (CN Assay) | Detectable Label (CN Ref. Assay) |
| 1 | 1 | 1 | 1 | 2 | Dye #1* | Dye #2 | | |
| 2 | 1 | 1 | 2 | 1 | Dye #1 | | | Dye #1 |
| 3 | 1 | 1 | 2 | 1 | Dye #1 | | | Dye #2 |
| 4 | 1 | 1 | 2 | 1 | DNA Binding Dye** | | | DNA Binding Dye |
| 5 | ≥2 | 1 | ≥3 | 1 | Dye #1 | | | Dye #1 |
| 6 | ≥2 | 1 | ≥3 | 1 | Dye #1 | | | Dye #2 |
| 7 | ≥2 | 1 | ≥3 | 1 | DNA Binding Dye | | | DNA Binding Dye |
| 8 | 1 | ≥2 | ≥3 | 1 | Dye #1 | | | Dye #1 |
| 9 | 1 | ≥2 | ≥3 | 1 | Dye #1 | | | Dye #2 |
| 10 | 1 | ≥2 | ≥3 | 1 | DNA Binding Dye | | | DNA Binding Dye |

TABLE 1-continued

Exemplary Karyotyping Assay Design Formats when an Unknown Sample is Tested Relative to a Calibrator Sample

| Format No. | No. CN Assays | No. CN Reference Assays | No. Reactions (per sample) | Plexy Per Reaction | Reaction #1 Detectable Label (CN Assay) | Reaction #1 Detectable Label (CN Ref. Assay) | Reaction #2 Detectable Label (CN Assay) | Reaction #2 Detectable Label (CN Ref. Assay) |
|---|---|---|---|---|---|---|---|---|
| 11 | ≥2 | ≥2 | ≥4 | 1 | Dye #1 | | | Dye #1 |
| 12 | ≥2 | ≥2 | ≥4 | 1 | Dye #1 | | | Dye #2 |
| 13 | ≥2 | ≥2 | ≥4 | 1 | DNA Binding Dye | | | DNA Binding Dye |
| 14 | ≥2 | 0 | ≥2 | 1 | Dye #1 | | Dye #1 | |
| 15 | ≥2 | 0 | ≥2 | 1 | Dye #1 | | Dye #2 | |
| 16 | ≥2 | 0 | ≥2 | 1 | DNA Binding Dye | | DNA Binding Dye | |

*Dyes are typically conjugated to primers or probes.
**DNA binding dyes are typically not conjugated to primers or probes.

NOTES

The number of reactions is per replicate per sample. Dye #1 and Dye #2 represent different fluorophores conjugated to probes or primers of the Copy Number Assay and Copy Number Reference Assay and provide differential fluorescence as the reaction generates amplification products.

DNA Binding Dye represents a fluorophore that binds to amplification products and provides fluorescence as the reaction generates amplification products.

Format 1 is one 2-plex reaction (i.e. a multiplex reaction).

Formats 2, 3, and 4 are variations of two 1-plex reactions (i.e., a single-plex reaction).

Formats 5, 6, and 7 are variations of 1-plex reactions that combine (via average, median, etc.) $C_T$ values from multiple Copy Number Assays.

Formats 8, 9, and 10 are variations of 1-plex reactions that combine (via average, median, etc.) $C_T$ values from multiple Copy Number Reference Assays.

Formats 11, 12, and 13 are variations of 1-plex reactions that combine (via average, median, etc.) $C_T$ values from multiple Copy Number Assays and combine (via average, median, etc.) $C_T$ values from multiple Copy Number Reference Assays.

Formats 14, 15, and 16 are variations of 1-plex reactions that provide multiple analyses via each Copy Number Assay, in turn, being compared to one or more of the remaining virtual Copy Number Reference Assays.

Copy Number Assays of format 5, 6, or 7 target the same chromosome.

Copy Number Reference Assays of format 8, 9, or 10 target the same chromosome.

Copy Number Assays of format 11, 12, or 13 target the same chromosome.

Copy Number Reference Assays of format 11, 12, or 13 target the same chromosome.

Copy Number Assays of format 14, 15, or 16 target different chromosomes.

Formats 5, 6, 7, 8, 9, 10, 11, 12, 13, 14, 15, and 16 may also permute and combine (via average, median, etc.) $\Delta C_T$ values.

Formats 2, 3, 4, 5, 6, 7, 8, 9, 10, 11, 12, 13, 14, 15, and 16 may also be multiplexed (even though the multiplexed assays may not provide $\Delta C_T$ value).

(Modified) permutations of different formats are also possible (e.g. format 14 with multiple Copy Number Assays per chromosome via incorporating aspects of format 5).

Detectable entities other than fluorophores may also be employed.

In certain formats outlined in Table 1, the detectable label can be the same (e.g., formats 2, 4, 5, 7, 8, 10, 11, 13, 14, and 16). In other formats, the detectable labels can be different (e.g., Dye #1, Dye #2, and DNA binding dye as in formats 1, 3, 6, 9, 12, or 15) and are conjugated to probes or primers to provide a differential value as the reaction generates amplification products. One or more DNA binding dyes can be used to detect amplification products generated during a reaction (such as real-time PCR) in a multiplex reaction or in separate 1-plex reactions. Typically, the DNA binding dyes are not conjugated to a probe or primer. The skilled artisan will also note the following from Table 1:

1) format 1 is a 2-plex reaction (i.e., multiplex reaction) and uses different detectable labels for each reaction;
2) formats 2, 3, and 4 are variations of two 1-plex reactions (i.e., single-plex reaction) and use the same or different detectable labels in each reaction;
3) formats 5, 6, and 7 are variations of 1-plex reactions that combine $C_T$ values from multiple copy number assays (via average, median, etc.), typically target the same chromosome, and can use the same or different detectable labels in each reaction;
4) formats 8, 9, and 10 are variations of 1-plex reactions that combine $C_T$ values from multiple copy number reference assays (via average, median, etc.), target the same chromosome, and use the same or different detectable labels in each reaction;
5) formats 11, 12, and 13 are variations of 1-plex reactions that combine $C_T$ values from multiple copy number assays (via average, median, etc.) and combine $C_T$ values from multiple copy number reference assays (via average, median, etc.), target the same chromosome, and use the same or different detectable labels in each reaction;
6) formats 14, 15, and 16 are variations of 1-plex reactions that provide multiple analyses in which each copy number assay is compared to one or more of the remaining virtual copy number reference assays, target different chromosomes, and use the same or different detectable labels in each reaction.

Formats 5, 6, 7, 8, 9, 10, 11, 12, 13, 14, 15, and 16 can also permute and combine (e.g., via average, median, etc.) $\Delta C_T$ values.

The $\Delta C_T$ value is defined herein as the $C_T$ of the test copy number assay minus the $C_T$ of the copy number reference assay. The $\Delta\Delta C_T$ value is defined herein as: [the $C_T$ of the test assay minus the $C_T$ of the reference assay of each test sample] minus [the $C_T$ of the test assay minus the $C_T$ of the reference assay of the calibrator sample]. In some embodiments, the $\Delta\Delta C_T$ values can also be permuted and combined. However, because the $\Delta C_T$ of the calibrator sample is subtracted from each $\Delta C_T$ of the test sample, the values being permuted and combined now ($\Delta\Delta C_T$ vs. $\Delta C_T$) are of a different scale, and track in a "parallel" manner (e.g., $\Delta C_T$s of 2, 4, 5 vs. $\Delta\Delta C_T$s of 1, 3, 4 where a value of 1 is subtracted from each). Formats 2, 3, 4, 5, 6, 7, 8, 9, 10, 11, 12, 13, 14, 15, and 16 can also be multiplexed even though the multiplexed assays may not provide a $\Delta C_T$ value. Modified permutations of different formats are also possible (for example, formats 5 and 14 can be combined for analysis of multiple copy number assays per chromosome).

In one embodiment, karyotyping assay format 1 of Table 1 uses a 2-plex real-time PCR reaction comprised of a copy number assay (or test assay) and a copy number reference assay wherein target loci outside of CNVRs are interrogated. Generally, the detectable labels used by each component of this karyotyping assay are different because the amplified products are contained within the same reaction. Subsequent copy number analysis by the $2^{-\Delta\Delta C_T}$ method is the same as that used in the TaqMan® Copy Number Assay. In this calculation, $\Delta\Delta C_T$ determined for each test copy number assay serves as the negative exponent of 2 in order to calculate the fold change for each test copy number assay relative to its corresponding copy number reference assay. This assay format provides for multiplexing of the copy number assay and the copy number reference assay, which minimizes the error of the $\Delta C_T$ calculation and minimizes the use of reagents and consumables. This karyotyping assay format can be used to interrogate a single chromosome or multiple chromosomes. In certain embodiments, the test copy number assay provides the copy number of the target locus of the test sample, as well as the copy number of the chromosome containing the target locus. Different samples having a particular target locus known to be outside of a CNVR can be used for the reference assay. To properly normalize for sample input variation, the target locus or chromosomal copy number for the reference assay should be the same for all samples. In such embodiments, the copy number assay and copy number reference assay can target different chromosomes. Alternatively, or in addition, each chromosome can be interrogated with both a copy number assay and a copy number reference assay. Typically, but not necessarily, each chromosome is assayed separately from one another.

Karyotyping assay formats 2, 3, and 4 of Table 1 each use two single-plex real-time PCR reactions and the same, two or three different, detectable label(s). One real-time PCR reaction is the copy number assay and the other real-time PCR reaction is the copy number reference assay. The detectable label used in each assay can be the same or different. Subsequent copy number analysis by the $2^{-\Delta\Delta C_T}$ method is performed as previously described hereinabove, with the exception that the replicate $C_T$ values of the copy number assay and copy number reference assay are typically, but not necessarily, averaged separately prior to calculating the average $\Delta C_T$ value. These karyotyping assay designs provide the following advantages: 1) the use of copy number assay and copy number reference assay utilizing the same detectable label conjugated to the probe or primer; 2) the use of previously incompatible assays that cannot be multiplexed due to assay interaction issues or PCR bias of one assay over another; and 3) the use of a DNA binding dye in order to minimize reagent costs. It is possible to use this assay format, or modified versions thereof, to interrogate a single chromosome or multiple chromosomes. Each chromosome is interrogated with both a copy number assay and a copy number reference assay and typically, but not necessarily, each chromosome is assayed separately from one another.

In some embodiments, the karyotyping assay uses one or more copy number assays specific for the chromosome of interest, and one or more copy number reference assays. In some embodiments, the average or median $C_T$ values can be used. An average average (or "double average") $C_T$ value is calculated by averaging the multiple average $C_T$ values derived from the replicates of each copy number assay when more than one copy number assay is used. One or more copy number assays against a chromosome or chromosomes different from the test sample can be used as controls. These control copy number assays fill the role served by copy number reference assay in karyotyping assay formats 1-4 described above. A "double" average $C_T$ value is calculated by averaging the multiple average $C_T$ values derived from the replicates of each copy number assay. The "double" average $\Delta C_T$ value can then be calculated from the two "double" average $C_T$ values. Subsequent copy number analysis by the $2^{-\Delta\Delta C_T}$ method is carried out as previously described herein. Karyotyping assay formats 5, 6, 7, 8, 9, 10, 11, 12, and 13 provide the following advantages: 1) allow one to use previously incompatible assays that cannot be multiplexed due to assay interaction issues or PCR bias of one assay over another; 2) allow one to use a DNA binding dye (e.g., SYBR Green I) in order to minimize reagent costs; 3) allow one to eliminate the use of a defined copy number reference assay; and 4) allow one to minimize aberrant copy number observed from a minority of copy number assays by diluting the aberrant average $C_T$ values in a "double" average $C_T$ value. Karyotyping assay formats 5, 6, 7, 8, 9, 10, 11, 12, or 13, or modified versions thereof, can be used to interrogate a single chromosome or multiple chromosomes.

In other embodiments, the copy number assays can serve as a copy number reference assay herein denoted as a "virtual copy number reference assay". In these embodiments, a multiplicity of copy number assays are performed and each individual copy number assay is compared to one or more of the remaining copy number assays, which then serve as the copy number reference assays. For example, if ten copy number assays are performed, copy number assay no. 1 is compared to each of copy number assays nos. 2-9, copy number assay no. 2 is compared to each of copy number assays nos. 1 and 3-10, and so forth, for a possible total number of 90 different copy number calculations. For each copy number determination, any two or more of the other nine virtual copy number reference assays can be combined (e.g., via average, median, etc.) toward a total number of ten different analyses. This combining takes place at the virtual copy number reference assay $C_T$ level or $\Delta C_T$ level with one copy number assay and up to nine virtual copy number reference assays. These karyotyping assay formats provide the following advantages: 1) the use of incompatible assays that cannot be multiplexed due to assay interaction issues or PCR bias of one assay over another; 2) the use of a DNA binding dye in order to minimize reagent costs; 3) elimination of a properly defined copy number reference assay; 4) confirmation of copy number using each copy number assay as a virtual copy number reference assay;

and 5) for troubleshooting of a copy number assay by the use of each copy number assay as a virtual copy number reference assay.

It is also possible to further modify these karyotyping assay formats. For example, in some embodiments, at least ten different copy number analyses can be used in karyotyping assay formats 14, 15, or 16, and the ten different average $\Delta C_T$ values derived from the ten different copy number analyses are then averaged toward a "double" average $\Delta C_T$ value. Subsequent copy number analysis by the $2^{-\Delta\Delta C_T}$ method is performed as previously described herein. This copy number analysis mirrors that of the other assays with the exception that average $\Delta C_T$ values, not average $C_T$ values, are being averaged. In other embodiments, assay formats 14, 15 or 16 can be combined with assay formats 5, 6, 7, 11, 12 or 13 by averaging the average $C_T$ values from multiple copy number assays prior to calculating $\Delta C_T$ values. For example, a karyotyping assay with 10 copy number assays in which five target chromosome 1 and five target chromosome 2, the replicate $C_T$ values are averaged prior to averaging the five assays targeting each chromosome. Accordingly, only two "double" average $C_T$ values exist, one for each chromosome. A variety of subsequent calculations of $\Delta C_T$ are possible. These karyotyping assay formats with modified copy number analyses provide the following advantages: 1) the use of previously incompatible assays that can not be multiplexed due to assay interaction issues or PCR bias of one assay over another; 2) the use of a DNA binding dye in order to minimize reagent costs; 3) do not rely on the use of a properly defined copy number reference assay; and 4) minimize aberrant copy number results observed in some copy number assays by diluting the aberrant average $\Delta C_T$ values in a "double" average $\Delta C_T$ value. Such assay formats can be used to interrogate a single chromosome or multiple chromosomes. It should also be noted that the real-time PCR reactions can utilize increased multiplexing.

Karyotyping methods that use a virtual copy number reference assay (i.e., those that do not utilize either a reference assay or calibrator sample) are also provided. Situations in which a reference assay is not used include the lack of a suitable reference genomic sequence, non-identification of a control assay locus from a reference genomic sequence, assay unavailability, cost reduction, or to facilitate ease of use. Situations in which a calibrator sample is not used include unavailability of such a sample or a reference sequence, to reduce costs, or facilitate ease of use. Such assays are described below.

In the following two embodiments, the copy number assay $C_T$ values and copy number reference assay $C_T$ values for the virtual calibrator sample are calculated. The copy number assay $C_T$ values can be calculated by averaging the replicate $C_T$ for each copy number assay and then averaging these values across the multiple test samples. Alternatively, the copy number assay $C_T$ values can be calculated by averaging replicate $C_T$ values of each copy number assay, averaging these values across multiple copy number assays (those targeting the same chromosome), and averaging these values across the multiple test samples. These methods can also be applied to the copy number reference assay $C_T$ values. Depending upon the number of copy number assays and copy number reference assays used, up to four formats can be used to perform this calculation. Furthermore, the copy number assays and the copy number reference assays for the test samples can be treated separately or in combination as outlined in Table 1.

In the first of these embodiments, a "virtual calibrator sample" can be used in lieu of an actual calibrator sample (i.e., virtual calibrator assay no. 1). Typically, in these karyotyping assays, one or more copy number assays targeting one or more test chromosomes, one or more copy number reference assays targeting one or more reference chromosomes, and two or more test samples (e.g., gDNA) are utilized. In these assays, the copy number of the reference chromosome may or may not be previously known. An average $C_T$ value is calculated from the replicate $C_T$ values of copy number assay. If more than one copy number assay is used, the average $C_T$ values of each copy number assay are averaged. This calculation is performed for each of the two or more test samples, and for the one or more reference assay(s). The average $C_T$ values or "double" average $C_T$ values can then be further averaged across the two or more test samples. This "double" or "triple" average $C_T$ value is representative of a "virtual" calibrator sample. If appropriate, other calculations, such as the median, can be used in lieu of the average. The calculated $C_T$ values from the copy number assay(s) and copy number reference assay(s) can then be used to calculate the $\Delta C_T$ value for each of the test samples. Subsequent copy number analysis by the $2^{-\Delta\Delta C_T}$ method (see below) is similar to that as previously described herein. More accurate results will typically result when the test samples are normalized to the same concentration prior to chromosomal copy number analysis and when additional reference assays are utilized. Even in the presence of equal numbers of target loci, different reference assays may provide different $C_T$ values due to differences in assay performance. Therefore, the use of additional reference assays can provide a more accurate $C_T$ representation of each test gDNA sample. Likewise, the use of additional test samples can provide a more accurate $C_T$ representation of the "virtual" calibrator sample.

In another of these embodiments, a modified "virtual calibrator sample" (i.e., virtual calibrator assay no. 2) can be used in lieu of an actual calibrator sample as described in the immediately preceding paragraph. However, after averaging replicate $C_T$ values, the average $C_T$ values from one copy number reference assay can be averaged across the multiple test samples. This "double" average $C_T$ value represents the $C_T$ value from the virtual calibrator sample. If multiple copy number reference assays are used, average $C_T$ values from replicates can be averaged across multiple copy number reference assays and then averaged across multiple test samples toward a "triple" average $C_T$ value representing the virtual calibrator sample. Multiple copy number assays can be treated separately or combined.

In yet other embodiments, multiple copy number assays with virtual calibrator assays are used, for example, multiple copy number assays targeting one or more test loci on a chromosome (virtual calibrator assay no. 1 targeting the test sample); multiple copy number assays targeting one or more test locus on a reference chromosome (virtual calibrator assay no. 2 targeting the virtual calibrator sample); multiple copy number reference assays targeting a reference chromosome (virtual calibrator assay no. 3, copy number reference assay targeting the test sample and the virtual calibrator sample). In these embodiments, the copy number of the reference chromosome may or may not be previously known. The copy number of the targeted chromosome(s) in virtual calibrator assays no. 2 and no. 3 need not be the same. In these embodiments, a calibrator sample is not required. "Double" average $C_T$ values are calculated from each of the three assay groups. The "double" average $C_T$ values from virtual calibrator assays no. 1 and no. 3 are then used to calculate the $\Delta C_T$ value for the test sample. If appropriate, other calculations, such as the median, can be used in lieu of the average. The "double" average $C_T$ values from virtual calibrator assays no. 2 and no.

3 are used to calculate the $\Delta C_T$ value for the "virtual" calibrator sample. Subsequent copy number analysis by the $2^{-\Delta\Delta C_T}$ method is similar to that previously described herein. It is noted that the use of additional test and reference assays can provide a more accurate $C_T$ representation of the test gDNA sample and "virtual" calibrator gDNA sample.

Yet another embodiment is similar to that described in the immediately preceding paragraph except that virtual calibrator assay #3 is omitted. Because the test sample and "virtual" calibrator sample are derived from the same biological sample, there is no need to normalize for input variation by using one or more reference assays. Therefore, the reference assays can be removed from the workflow. Upon calculating the "double" average $C_T$ values from virtual calibrator assays no. 1 and no. 2, the "double" average $C_T$ value from virtual calibrator assay no. 2, representing the "virtual" calibrator sample, is subtracted from the "double" average $C_T$ value from assay group no. 1, representing the test sample, to calculate a $\Delta C_T$ value. If appropriate, other calculations, such as the median, can be used in lieu of the average. Because the reference assays are not used, calculation of relative quantity via the equation of $2^{-\Delta\Delta C_T}$ is replaced with calculation of relative quantity via the equation of the $2^{-\Delta C_T}$. Subsequent copy number analysis is similar to that previously described herein.

As described above, data generated using the karyotyping methods described herein (with or without reference or calibrator samples) can be analyzed using any of several well-known methods or algorithms. As an example, relative copy number can be calculated using assay format 1 (of Table 1) as shown in Table 2:

TABLE 2

Karyotyping Assay Format 1 Performed Without Replicates

| Step | Description | Test or Unknown Sample | Calibrator Sample |
|---|---|---|---|
| 1 | Determine copy number of calibrator sample | TBD | 2 |
| 2 | Collect $C_T$ value from copy number assay | 23 | 20 |
| 3 | Collect $C_T$ value from copy number reference assay | 23 | 21 |
| 4 | Calculate $\Delta C_T$ value ($C_T$ from CN Assay – $C_T$ from CN Ref Assay) | 0 | –1 |
| 5 | Calculate $\Delta\Delta C_T$ value ($\Delta C_T$ from each sample – $\Delta C_T$ from calibrator sample) | 1 | 0 |
| 6 | Calculate relative quantity (RQ = $2^{-\Delta\Delta C_T}$) | 0.5 | 1 |
| 7 | Calculate copy number (CN = RQ × CN of calibrator sample) | 1 | 2 |

As understood by those of skill in the art, a one cycle difference is theoretically a two-fold difference in quantity of the target sample. The skilled artisan can derive from step 2 that the Test or Unknown Sample ($C_T$ value=23) can have eight-fold fewer copies than the Calibrator Sample ($C_T$ value=20). However, because the copy number reference assay targets the same number of copies in all samples, the test sample ($C_T$ value=23) actually contains four-fold less sample input the calibrator sample ($C_T$ value=21). Because of the normalization of sample input variation via the copy number reference assay, it can be determined that the test sample has two-fold fewer copies than the calibrator sample (i.e., 4-fold variation is accounted for as sample input variation from the initial 8-fold variation) indicating that the actual copy number variation between the test and calibrator samples is two-fold.

The data generated using the methods described herein can also be analyzed using CopyCaller™ software available from Applied Biosystems. CopyCaller™ software is based on the $2^{-\Delta\Delta C_T}$ method described by Livak, et al. (supra). In one method, the user is required to select one sample as the calibrator sample and to identify the copy number thereof. For example, if the target loci in the test sample (such as gDNA) is detected using VIC™ dye and the target loci in the calibrator sample is detected using FAM™ dye, the $\Delta C_T$ value is calculated for each reaction well by subtracting the VIC™ $C_T$ value from the FAM™ $C_T$ value. The calculation of the $\Delta C_T$ value normalizes for sample input variation between wells. Because multiple replicates are typically assayed, the $\Delta C_T$ values from each replicate for each sample are averaged toward an average $\Delta C_T$ value for each sample. The $\Delta\Delta C_T$ value is calculated for each sample by subtracting the average $\Delta C_T$ value of the calibrator sample from the average $\Delta C_T$ value of each test sample. The calculation of the $\Delta\Delta C_T$ value provides for determining the copy number of a test sample relative to the calibrator sample of known copy number. The $\Delta\Delta C_T$ values are converted to a relative quantity (RQ) by the equation of RQ=$2^{-\Delta\Delta C_T}$. The RQ value of each sample is then multiplied by the copy number of the calibrator sample to obtain the copy number determination of each sample.

Another method of copy number analysis by CopyCaller™ utilizes proprietary algorithms for determining copy number without selection of a calibrator sample. The user is only required to identify the most common copy number to be provided by the samples. Both methods of copy number analysis by CopyCaller™ employ outlier removal strategies for all $C_T$ and $\Delta C_T$ values. CopyCaller™ can also provide confidence and absolute Z-score values for the predicted copy number values. It is also noted that copy number analysis methods other than the $2^{-\Delta\Delta C_T}$ method can be utilized (e.g., Cikos, et al. Anal Biochem. 384:1-10 (2009)). Other methods of analysis can also be used, as would be understood by one of skill in the art.

While many of the embodiments described herein relate to PCR, other amplification or product detection methods or reagents can also be utilized. For example, such methods or reagents may include any of several methods that can be used to amplify the target nucleic acid from the sample. The term "amplifying" which typically refers to an "exponential" increase in target nucleic acid is used herein to describe both linear and exponential increases in the numbers of a select target sequence of nucleic acid. The term "amplification reaction mixture" refers to an aqueous solution comprising the various reagents used to amplify a target nucleic acid. These include enzymes, including, but not limited to, polymerases (such as DNA polymerase, RNA polymerase and reverse transcriptase), aqueous buffers, salts, amplification primers, target nucleic acid, and nucleoside triphosphates. Depending upon the context, the mixture can be either a complete or incomplete amplification reaction mixture. The method used to amplify the target nucleic acid can be any method available to one of skill in the art. Any in vitro means for multiplying or amplifying the copies of a target sequence of nucleic acid can be utilized. These include linear, logarithmic, or any other amplification method. Exemplary methods include polymerase chain reaction (PCR; see, e.g., U.S. Pat. Nos. 4,683, 202; 4,683,195; 4,965,188; and 5,035,996), isothermal procedures (using one or more RNA polymerases (see, e.g., WO 2006/081222), strand displacement (see, e.g., U.S. Pat. No. RE39,007), partial destruction of primer molecules (see, e.g., WO 2006/087574), ligase chain reaction (LCR) (see, e.g., Wu, et al. Genomics 4:560-569 (1989) and Barany, Proc. Natl. Acad. Sci. USA 88:189-193 (1991)), Qβ RNA replicase systems, RNA transcription-based systems (e.g., TAS, 3SR), rolling circle amplification (RCA) (see, e.g., U.S. Pat. No. 5,854,033; U.S. Pub. No. 2004/0265897; Lizardi, et al. Nat. Genet. 19: 225-232 (1998); and Barter, et al. Nucleic Acid Res. 26:5073-5078 (1998)), and strand displacement amplification (SDA) (Little, et al. Clin. Chem. 45:777-784 (1999)), among others. Many systems are suitable for use in amplifying target nucleic acids and are contemplated herein as would be understood by one of skill in the art.

Any of several methods can be used to detect amplified target nucleic acids using primers or probes. Many different reagents, systems, or detectable labels can be used in the methods described herein. These include, for example, TaqMan® systems, detectable nucleic acid intercalating agents, such as ethidium bromide and SYBR dyes, detectable label-quencher systems (e.g., FRET, salicylate/DTPA ligand systems (see, e.g., Oser et al. Angew. Chem. Int. Ed. Engl. 29:1167-1169 (1990)), displacement hybridization, homologous probes, assays described in EP 070685), molecular beacons (e.g., NASBA), Scorpion, locked nucleic acid (LNA) bases (Singh, et al. Chem. Commun. 4:455-456 (1998)), peptide nucleic acid (PNA) probes (Pellestor, et al. Eur. J. Hum. Gen. 12:694-700 (2004)), Eclipse probes (Afonina, et al. Biotechniques 32:940-949 (2002)), light-up probes (Svanvik, et al. Anal. Biochem. 281:26-35 (2000)), molecular beacons (Tyagi, et al. Nat. Biotechnol. 14:303-308 (1996)), tripartite molecular beacons (Nutiu, Nucleic Acids Res. 30:E94 (2002)), QuantiProbes (www.qiagen.com), HyBeacons (French, et al. Mol. Cell. Probes 15:363-374 (2001)), displacement probes (Li, et al. Nucleic Acids Res. 30:E5 (2002)), HybProbes (Cardullo, et al. Proc. Natl. Acad. Sci. USA 85:8790-8794 (1988)), MGB Alert® probes (www.nanogen.com), Q-PNA (Fiandaca, et al. Genome Res. 11:609-613 (2001)), Plexor (www.Promega.com), LUX primers (Nazarenko, et al. Nucleic Acids Res. 30:E37 (2002)), Scorpion primers (Whitcombe, et al. Nat. Biotechnol. 17:804-807 (1999)), AmpliFluor® (Sunrise) primers (Nazarenko, et al. Nucleic Acids Res. 25:2516-2521 (1997)), DzyNA primers (Todd, et al. Clin. Chem. 46:625-630 (2000)), and the like. In each of these assays, the generation of amplification products can be monitored while the reaction is in progress. An apparatus for detecting the signal generated by the detectable label can be used to detect, measure, and quantify the signal before, during, or after amplification. The particular type of signal may dictate the choice of detection method. For example, in some embodiments, fluorescent dyes are used to label probes or amplified products. The probes bind to single-stranded or double-stranded amplified products, or the dyes intercalate into the double-stranded amplified products, and consequently, the resulting fluorescence increases as the amount of amplified product increases. In some embodiments, the $T_m$ is ascertained by observing a fluorescence decrease as the double-stranded amplified product dissociates and the intercalating dye is released therefrom. The amount of fluorescence can be quantitated using standard equipment such as a spectra-fluorometer, for example. The use of other methods or reagents is also contemplated herein as would be understood by one of skill in the art.

One exemplary method for amplifying and detecting target nucleic acids is the TaqMan® system described above (see, e.g., U.S. Pat. Nos. 4,889,818; 5,079,352; 5,210,015; 5,436,134; 5,487,972; 5,658,751; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and 7,445,900). As described herein and elsewhere, TaqMan® assays are typically carried out by performing nucleic acid amplification on a target polynucleotide using a nucleic acid polymerase having 5'-to-3' nuclease activity, a primer capable of hybridizing to said target polynucleotide, and an oligonucleotide probe capable of hybridizing to said target polynucleotide 3' relative to said primer. The oligonucleotide probe typically includes a detectable label (e.g., a fluorescent reporter molecule) and a quencher molecule capable of quenching the fluorescence of said reporter molecule. The oligonucleotide probe typically exists in at least one single-stranded conformation when unhybridized where said quencher molecule quenches the fluorescence of said reporter molecule. When hybridized to a target nucleic acid, the probe exhibits at least one other conformation in which the fluorescence of the reporter molecule is unquenched. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

Another exemplary system utilizes double-stranded probes in displacement hybridization methods (see, e.g., Morrison, et al. Anal. Biochem. 183:231-244 (1989); and Li, et al., (supra)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes can be used, each containing different detectable labels, such that multiple target nucleic acids may be queried in a single reaction.

Additional exemplary methods for amplifying and detecting target nucleic acids involve "molecular beacons", which are single-stranded hairpin shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher dye that prevents the detectable label from emitting a signal when the probe is in the closed loop shape (i.e., not bound to a target nucleic acid). Thus, in the presence of a complementary target, the "stem" portion of the beacon separates out resulting in the probe hybridizing to the target. Other types of molecular beacons are also known and may be suitable for use in the methods described herein. Molecular beacons can be used in a variety of assay systems. One such system is nucleic acid sequence-based amplification (NASBA®), a single step isothermal process for amplifying RNA to double stranded DNA without temperature cycling. A NASBA® reaction typically requires avian myeloblastosis virus (AMV), reverse transcriptase (RT), T7 RNA polymerase, RNase H, and two oligonucleotide primers. After amplification, the amplified target nucleic acid can be detected using a molecular beacon. Other uses for molecular beacons are known in the art and would be suitable for use in the methods described herein.

The Scorpion system is another exemplary assay format that can be used in the methods described herein. Scorpion primers are bi-functional molecules in which a primer is covalently linked to the probe, along with a detectable label (e.g., a fluorophore) and a quencher. In the presence of a target nucleic acid, the detectable label and the quencher separate which leads to an increase in signal emitted from the detectable label. Typically, a primer used in the amplification reaction includes a probe element at the 5' end along with a "PCR blocker" element (e.g., HEG monomer) at the start of the hairpin loop. The probe typically includes a self-complementary stem sequence with a detectable label at one end and a quencher at the other. In the initial amplification cycles (e.g., PCR), the primer hybridizes to the target and extension occurs due to the action of the polymerase. The Scorpion system can be used to examine and identify point mutations using multiple probes that have different tags to distinguish between the probes. Using PCR as an example, after one extension cycle is complete, the newly synthesized target region will be attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for molecular beacons are known in the art and would be suitable for use in the methods described herein.

One or more detectable labels or quenching agents are typically attached to a primer or probe. The detectable label can emit a signal when free or when bound to the target nucleic acid. The detectable label can also emit a signal when in proximity to another detectable label. Detectable labels can also be used with quencher molecules such that the signal is only detectable when not in sufficiently close proximity to the quencher molecule. For instance, in some embodiments, the assay system can cause the detectable label to be liberated from the quenching molecule. Any of several detectable labels can be used to label the primers and probes used in the methods described herein.

As mentioned above, in some embodiments the detectable label can be attached to a probe, which can be incorporated into a primer, or may otherwise bind to amplified target nucleic acid (e.g., a detectable nucleic acid binding agent such as an intercalating or non-intercalating dye). When using more than one detectable label, each should differ in their spectral properties such that the labels can be distinguished from each other, or such that together the detectable labels emit a signal that is not emitted by either detectable label alone. Exemplary detectable labels include, for instance, a fluorescent dye or fluorphore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluoresceins (e.g., 5-carboxy-2,7-dichlorofluorescein; 5-Carboxyfluorescein (5-FAM); 5-HAT (Hydroxy Tryptamine); 6-HAT; 6-JOE; 6-carboxyfluorescein (6-FAM); FITC); Alexa fluors (e.g., 350, 405, 430, 488, 500, 514, 532, 546, 555, 568, 594, 610, 633, 635, 647, 660, 680, 700, 750); BODIPY fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP, EGFP), blue fluorescent protein (e.g., BFP, EBFP, EBFP2, Azurite, mKalama1), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY FL/BODIPY FL, Fluorescein/QSY7 and QSY9), LysoTracker and LysoSensor (e.g., LysoTracker Blue DND-22, LysoTracker Blue-White DPX, LysoTracker Yellow HCK-123, LysoTracker Green DND-26, LysoTracker Red DND-99, LysoSensor Blue DND-167, LysoSensor Green DND-189, LysoSensor Green DND-153, LysoSensor Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2,5-ROX (carboxy-X-rhodamine), Sulphorhodamine B can C, Sulphorhodamine G Extra, Tetramethylrhodamine (TRITC), WT), Texas Red, Texas Red-X, VIC and other labels described in, e.g., US Pub. No. 2009/0197254), among others as would be known to those of skill in the art.

The amplified target nucleic acid can also be detected using a detectable nucleic acid binding agent (see, e.g., Table 1) which can be, for example, an intercalating agent or a non-intercalating agent. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent can produce a detectable signal directly or indirectly. The signal can be detectable directly using, for example, fluorescence or absorbance, or indirectly using, for example, any moiety or ligand that is detectably affected by its proximity to double-stranded nucleic acid is suitable, for example a substituted label moiety or binding ligand attached to the nucleic acid binding agent. It is typically necessary for the nucleic acid binding agent to produce a detectable signal when bound to a double-stranded nucleic acid that is distinguishable from the signal produced when that same agent is in solution or bound to a single-stranded nucleic acid. For example, intercalating agents, such as ethidium bromide and SYBR dyes, fluoresce more intensely when intercalated into double-stranded DNA than when bound to single-stranded DNA, RNA, or in solution (see, e.g., U.S. Pat. Nos. 5,994,056; 6,171,785; and 6,814,934). Similarly, actinomycin D fluoresces red when bound to single-stranded nucleic acids, and green when bound to double-stranded nucleic acids. And in another example, the photoreactive psoralen 4-aminomethyle-4-5',8-trimethylpsoralen (AMT) has been reported to exhibit decreased absorption at long wavelengths and fluorescence upon intercalation into double-stranded DNA (Johnston et al. Photochem. Photobiol. 33:785-791 (1981). For example, U.S. Pat. No. 4,257,774 describes the direct binding of fluorescent intercalators to DNA (e.g., ethidium salts, daunomycin, mepacrine and acridine orange, 4',6-diamidino-α-phenylindole). Non-intercalating agents (e.g., minor groove binders such as Hoechst 33258, distamycin, netropsin) may also be suitable for use. For example, Hoechst 33258 (Searle, et al. Nucleic Acids Res. 18:3753-3762 (1990)) exhibits altered fluorescence with an increasing amount of target. Exemplary detectable DNA binding agents may include, for example, acridine derivatives (e.g., acridine homodimer, acridine orange, acridine yellow, 9-amino-6-chloro-2-methoxyacridine (ACMA), proflavin), actinomycins (e.g., actinomycin D (Jain, et al. J. Mol. Biol. 68:1-10

(1972), 7-amino-actinomycin D (7-AAD)), anthramycin, auramine, azure B, BOBO™-1, BOBO™-3, BO-PRO™-1, BO-PRO™-3, chromomycin (e.g., A3), crystal violet, cyanine dyes, DAPI (Kapuściński, et al. Nucleic Acids Res. 6:3519-3534 (1979)), 4',6-diamidino-2-phenylindole (DAPI), daunomycin, distamycin (e.g., distamycin D), dyes described in U.S. Pat. No. 7,387,887, ellipticine, ethidium salts (e.g., ethidium bromide, ethidium homdimer-1, ethidium homdimer-2, dihydroethidium (also known as hydroethidine), ethidium monoazide), fluorcoumanin, fluorescent intercalators as described in U.S. Pat. No. 4,257,774, GelStar®(Cambrex Bio Science Rockland Inc., Rockland, Me.), hexidium iodide, Hoechst 33258 (Searle, et al., (supra)), Hoechst 33342, Hoechst 34580, homidium, hydroxystilbamidine, JO-JO-1, JO-PRO™-1, LDS 751, LOLO-1, LO-PRO™-1, malachite green, mepacrine (e.g., orange), mithramycin, netropsin, the Nissl substance, 4',6-diamidino-α-phenylindole, proflavine, POPO™-1, POPO™-3, PO-PRO™-1, propidium iodide, ruthenium polypyridyls, Sevron dyes (e.g., Brilliant Red 2B, Brilliant Red 4G, Brilliant Red B, Orange, Yellow L), SYBR 101, SYBR 102, SYBER 103, SYBR® Gold, SYBR® Green I (U.S. Pat. Nos. 5,436,134 and 5,658,751), SYBR® Green II, SYTOX® Blue, SYTOX® Green, SYTOX® Orange, SYTO® 1, SYTO® 11, SYTO® 13, SYTO® 14, SYTO® 15, SYTO® 16, SYTO® 17, SYTO® 18, SYTO® 20, SYTO® 21, SYTO® 22, SYTO® 23, SYTO® 24, SYTO® 25, SYTO® 40, SYTO® 43, SYTO® 44, SYTO® 45, SYTO® 59, SYTO® 60, SYTO® 61, SYTO® 62, SYTO® 63, SYTO® 64, SYTO® 80, SYTO® 81, SYTO® 82, SYTO® 83, SYTO® 84, SYTO® 85, thiazole orange (Aldrich Chemical Co., Milwaukee, Wis.), TO-PRO-1, TO-PRO-3, TO-PRO-5, TOTO-1, TOTO-2, TOTO™-3, YO-PRO®-1, YO-PRO®-3, YOYO-1, and YOYO®-3 (Molecular Probes, Inc., Eugene, Oreg.), among others. SYBR® Green I (see, e.g., U.S. Pat. Nos. 5,436,134; 5,658,751; and/or 6,569,927), for example, has been used to monitor a PCR reaction by amplifying the target sequence in the presence of the dye, exciting the biological sample with light at a wavelength absorbed by the dye and detecting the emission therefrom; and, determining a melting profile of the amplified target sequence. The presence of amplified products and, therefore, the target sequence in the sample, can thereafter be determined by, for example, performing a melting curve analysis (i.e., non-linear least squares regression of the sum of multiple gaussians). It is to be understood that the use of the SYBR® Green dye is presented as an example and that many such dyes may be used in the methods described herein. Other nucleic acid binding agents can also be suitable as would be understood by one of skill in the art.

The nature of the test and control amplified products can vary depending on the type of assay system that is utilized. For example, the product of PCR amplification of DNA is typically referred to as an "amplicon". In contrast, the Ligation Chain Reaction product is instead referred to as "LCR product" or "ligation product". In PCR, primers are utilized but in other methods, such as LCR ligation probes, can be utilized. It is known that both PCR and LCR functions through exponential amplification or linear amplification. It is important to note, however, that regardless of the kind of method used to perform amplification or detection of target loci, any target loci should exhibit similar "amplification efficiency" to one another (e.g., within about 10 percent). This means that within a particular reaction, the target loci being compared should amplify to approximately the same extent (e.g., within about 10 percent) under similar reaction conditions. It is understood in the art that amplification efficiency may be affected by, for example, sample quality (e.g., purity, presence of reaction inhibitors, and the like) or sequence (e.g., G/C content, mismatches, and the like). As used herein, amplification efficiency refers to any product that may be quantified to determine copy number (e.g., a PCR amplicon, an LCR ligation product, or similar product). Variations in amplification due to factors other than copy number may thereby be limited.

For example, when using PCR, it may be optimal to amplify amplicons of a similar size (e.g., within about ten percent of the length of any other amplicon) and amplify with similar amplification efficiency (e.g., within about ten percent of one another). PCR-related amplification efficiencies can be tested as described by Livak, et al. (supra), or as is otherwise known in the art. Briefly, Livak, et al. teach that, as the $\Delta C_T$ varies with template dilution, amplifications can be performed over a particular range (e.g., a 100-fold range) and the $\Delta C_T$ calculated at each point. A log of dilution versus $\Delta C_T$ is made and if the absolute value of the slope is close to zero, the efficiencies are similar. For PCR-based assays, the resultant amplicons are typically about 70 to 125 nucleotides in length, and can be less than or equal to about 110 nucleotides in length. The amplification efficiency is typically controlled by amplifying amplicons of similar G/C content, length, or melting temperature. The primers used in the test and control assays are also typically of similar character (e.g., G/C content, length, melting temperature). Variations of these parameters can also be used, as would be understood by the skilled artisan.

The methods described herein typically require a target locus to be present on the one or more chromosomes being studied (exceptions include, for example, the absence of a target locus such as when the Y chromosome is assayed in a normal (i.e., XX) female sample). Pre-existing bioinformatics algorithms can be used to generate "qualified" pre-characterized genome targets and to design assays against those targets. Qualified genome targets may include, for example, genes, exons, introns, intergenic regions, junctions thereof, evolutionarily conserved regions ("cold" spots not prone to change), or other regions within the genome. In certain embodiments, multiple target loci can be interrogated on a chromosome. This can be used to control for unanticipated abnormalities in regions containing target loci. It is possible that such regions can include a duplication, deletion, or other abnormality that may result in an inaccurate karyotype determination. By targeting multiple target loci of a chromosome, the user can control for such unanticipated abnormalities. Thus, in certain embodiments, one, more than one, at least two, or two or more loci are targeted from at least one chromosome or arm thereof, but optionally include more than one arm, to be interrogated. In certain embodiments, three, four, five, six, seven, eight, nine, 10 or more loci may be interrogated. In one embodiment, four loci are interrogated on each chromosome. In some embodiments, it may also be important to separate the target loci by a particular approximate number of nucleotides which can, in some embodiments, be calculated as is known in the art to further insure against interrogating a CNVR. It may also be beneficial to separate each target loci from any other target loci by approximately the same number of nucleotides (e.g., along the arm of a chromosome). Many suitable targets exist on each chromosome.

Exemplary targets (which can serve as qualified targets) and their corresponding PCR primers that can be used to interrogate human chromosomes are shown in Table 3. The probes that can be used in combination with particular primers or primer pairs, and the sequences amplified using particular primer pairs are shown in Table 4. One or more of such target loci can be amplified from a biological sample (e.g., gDNA). It should be understood that non-CNVR targets and corresponding probes or primers other than those listed in Tables 3 and 4 can be used in the methods disclosed herein. It is noted that chromosomes of other organisms may be similarly interrogated but that different target loci are used.

TABLE 3

Exemplary Targets and PCR Primers

| Chromosome location | Cytoband | Gene Symbol | Forward Primer | SEQ ID NO | Reverse Primer | SEQ ID NO |
|---|---|---|---|---|---|---|
| 1: 36669968-36670038 | 1p34.3 | C1orf102 | CCAGGGCTGCCTATTGACTT | 1 | GCTGATCCGGCAGACACT | 2 |
| 1: 19882469-19882569 | 1p36.13 | TMCO4 | CCCACGGCCTTCAGGAT | 3 | GGGCTCTGCACACCCA | 4 |
| 1: 176197341-176197427 | 1q25.2 | SEC16B | AACCCACCAGCCTGAACTG | 5 | TGAGCTCAGTCAGTACATCAGAGAT | 6 |
| 1: 203386468-203386559 | 1q32.1 | DSTYK | CACAATGCTGCCTGACATCAT | 7 | TGCTTTGTTGGCAGCTGGATA | 8 |
| 2: 51062327-51062418 | 2p16.3 | NRXN1 | TGACAGCTTTTGGCTCAGAAATTAGA | 9 | CCTGTCACTGGGAGGAAATCCATA | 10 |
| 2: 27426789-27426880 | 2p23.3 | GTF3C2 | CACGATGAGGGTTGAGGGAAAA | 11 | GATTCTTGAGCCAGCAGCTGTA | 12 |
| 2: 141646278-141646366 | 2q22.1 | LRP1B | GCCAGGATGCTCCATGTAGTA | 13 | AAGGATTATTCTGACGGTTCATGTTGT | 14 |
| 2: 166773406-166773515 | 2q24.3 | SCN9A | AGGTGAAAAAGTACTTATGAGGATGATGAAT | 15 | TTGATCAAAGCTTATGGCTCTATCAACT | 16 |
| 3: 71541265-71541358 | 3p14.1 | FOXP1 | AAACAGGAGAATGAATGAATATGCT | 17 | CCATAGACAGATTAGCCTGCTTCTT | 18 |
| 3: 51489723-51489813 | 3p21.2 | VPRBP | GCCATCCTCCTTTTTCTCATCCT | 19 | TGGGTTTGGTGCCTCACA | 20 |
| 3: 98908486-98908579 | 3q11.2 | EPHA6 | TGGCATGTGAGATGTGTTCAAGAAA | 21 | AAAGGGTACCACTAGAGAGGCA | 22 |
| 3: 142551967-142552067 | 3q23 | ZBTB38 | TCCCTCAAGTTTATTCAGTCTCCTTATGT | 23 | AGAGCAAGACGTCCAAATTGAAGTA | 24 |
| 4: 46733909-46734018 | 4p12 | GABRB1 | CATTTCCAAGTACAGTAACTCCACAGTA | 25 | CCTCAGTGGTGCAAAAACAGTT | 26 |
| 4: 6931464-6931545 | 4p16.1 | KIAA0232 | CCCAAGCACCTGTAGCATCATC | 27 | CCTCAAACATCTGCCTTCATGTGT | 28 |
| 4: 100651173-100651274 | 4q23 | C4orf17 | GGAATGTTACCACGTTGCTAAGC | 29 | CAGCTGTCTTCATCCAGTTTCTCA | 30 |
| 4: 146906234-146906321 | 4q31.22 | ZNF827 | TTTCTGGGAGCCATCTGAATCATC | 31 | CAGCGAATCAAATAGCCCCTCTT | 32 |
| 5: 26772993-26773084 | 5p14.1 | LOC100131678 | GGTATGACCTGGACACATTAAGCA | 33 | AGGAGGGAGATAAAAATAATGAGAAATGTAAGC | 34 |
| 5: 13791807-13791884 | 5p15.2 | DNAH5 | GCAAGCCACAGGAAGAGGAA | 35 | TGTACAATTTGACTTGGTGCCAGAA | 36 |
| 5: 108773400-108773485 | 5q21.3 | PJA2 | GCGGAACAAGCCAGACTGAA | 37 | GAGGTTCGAGCGCTGTTCT | 38 |
| 5: 122258322-122258422 | 5q23.2 | SNX24 | GTTTTAGAAGGAAGAGGGCTAGGAA | 39 | AGAATGTGCAGTCAACACTCAGAA | 40 |
| 6: 12970453-12970529 | 6p24.1 | PHACTR1 | GTATAGGCAGCGACAGCACTT | 41 | AGATCTCCACAGGACTCACCAA | 42 |
| 6: 3672898-3672977 | 6p25.2 | C6orf145 | GAAAACCAAAGCAACAAGGTGAGT | 43 | GGGAGATGGGAGTAAGTTCCAAAC | 44 |

TABLE 3-continued

Exemplary Targets and PCR Primers

| Chromosome location | Cytoband | Gene Symbol | Forward Primer | SEQ ID NO | Reverse Primer | SEQ ID NO |
|---|---|---|---|---|---|---|
| 6: 74590195-74590286 | 6q13 | CD109 | GGGTTGCAGGGATGGTGTA | 45 | TGCATTCATTCTGATCTTCCACACA | 46 |
| 6: 112680120-112680214 | 6q21 | LAMA4 | GGGATCTGTAACTTGACCAAGGT | 47 | GCAGCACAGCAAAGTGTTTCAG | 48 |
| 7: 47936016-47936124 | 7p12.3 | PKD1L1 | GATGGTATCTCCCACAAGTCACTAC | 49 | CAATTTGCAGCACAAGGAGCTA | 50 |
| 7: 40801751-40801837 | 7p14.1 | C7orf10 | CTGTCTGATTGTTAAGAGGGCTTGT | 51 | GTCACAACTTGTTCTTGGGAGTTTG | 52 |
| 7: 99515052-99515140 | 7q22.1 | ZNF3 | GATAGATGGCCTGGCAGTAAGAAC | 53 | GCCTTCTAGGGACTGACTTCAA | 54 |
| 7: 134591172-134591254 | 7q33 | STRA8 | TGAACCTTTGACACCTTCCCAAA | 55 | TGACAGCAAATATTACCGAAGGTGAT | 56 |
| 8: 12902405-12902494 | 8p22 | C8orf79 | GATCTCCTCTTCTGTGCCTACATC | 57 | TGTGATGACAAAACATAAATGAGACTGAGT | 58 |
| 8: 10106677-10106775 | 8p23.1 | MSRA | GTTCTCTCTGGCCGTCAATATCTT | 59 | CACTTCTGCAGAGGCTGGAA | 60 |
| 8: 61648551-61648656 | 8q12.1 | RAB2A | GGGACCTGGGTTTCCTGATACT | 61 | ACCCAGAGTCGAGTGGACAAT | 62 |
| 8: 75439579-75439660 | 8q21.11 | GDAP1 | TGGAGAGAACCCCAGGCTTTAT | 63 | CTAAAGCAATGTGTGTGATTCATAAGCA | 64 |
| 9: 26949592-26949694 | 9p21.2 | IFT74 | AGATGGGATCAAGGGTAAATCAGAGT | 65 | GGGCACATAAACTTCTCTACATCCA | 66 |
| 9: 408149-408232 | 9p24.3 | DOCK8 | TGGCCATAGCAGGGAATAATTTCA | 67 | ACCAGACACATGTGCACCAA | 68 |
| 9: 78498063-78498161 | 9q21.13 | PRUNE2 | GGATGGGCAATTTTAGGTAATCTCCAA | 69 | ATCTCTTAAGCACCTACCCTGGT | 70 |
| 9: 100023301-100023371 | 9q22.33 | TBC1D2 | CCAGTGCCTTGTGCAGGAT | 71 | CCTCCCTGAGCTCACAAGATT | 72 |
| 10: 17011452-17011533 | 10p13 | CUBN | AAATAGAATATGAGACATGAGTAAATATGCCCTTTT | 73 | TCAAGTTGTAGTCAGTGCCACAAA | 74 |
| 10: 5401127-5401221 | 10p15.1 | UCN3 | CAAAAGCTACAAGCCAGAGATACGA | 75 | ACACATATGTACAGAGAGACCAGGAA | 76 |
| 10: 63195641-63195741 | 10q21.2 | C10orf107 | AAGACAATGTGCAGCAAAAGATAGC | 77 | GGCCTCTTCCTGTATTTGCAGTTT | 78 |
| 10: 121323685-121323788 | 10826.11 | LOC100133264 TIAL1 | CAAATTTTACCCACACAGCCTGAAA | 79 | GCTTAAGTTGTATGTGTGCAGAGTT | 80 |
| 11: 46730822-46730911 | 11p11.2 | CKAP5 | AAAACAAGTAGGGCACTGGAAGAA | 81 | TGCCCTTTCAACTGCTGATTCTAAT | 82 |
| 11: 6200897-6200970 | 11p15.4 | FAM160A2 | CATTGCAGAACTCCAGGGAACT | 83 | CTGTCTGCGACGGGAAGA | 84 |
| 11: 62241048-62241147 | 11q12.3 | HNRNPUL2 | CCCCGGCTTCGGTTCT | 85 | AGTACAAGGAGGAGGCAAGGAA | 86 |
| 11: 130999952-131000023 | 11q25 | NTM | GGAATCCAGGAGGTGGTGATG | 87 | CAGCCAACTAAACTGTATGCTCTGT | 88 |
| 12: 27346341-27346426 | 12p11.23 | STK38L | AAGAAATTAGAAGTGGCCATGGAAGA | 89 | GGGTGCTTTTGTACAGTAATTATAGGT | 90 |
| 12: 16036914-16037009 | 12p12.3 | DERA | CAGGTCAATCTACTGCTAAGGGATT | 91 | CCGCTACTGAAAGATAAAGCCACTT | 92 |

TABLE 3-continued

Exemplary Targets and PCR Primers

| Chromosome location | Cytoband | Gene Symbol | Forward Primer | SEQ ID NO | Reverse Primer | SEQ ID NO |
|---|---|---|---|---|---|---|
| 12: 42605583-42605676 | 12q12 | TMEM117 | AGGCTGGTGGAGGCTAGT | 93 | GAAACCCTGGGAACCATACCAT | 94 |
| 12: 92044805-92044882 | 12q22 | LOC643339 | CTTGGGATGTTTTATAAGTGTCTGTCTGT | 95 | GGGAAGGGACCTGAGGATAGG | 96 |
| 13: 19660225-19660311 | 13q12.11 | GJB2 | TTGACATGAGGCCATTTTGCTATCA | 97 | GCACCTAACAACATTGTAGCCTCAA | 98 |
| 13: 38442357-38442447 | 13q13.3 | STOML3 | AGATCTGGGACAAGGTCTGTGT | 99 | GCTAATGTCAACGATGTCCATCAAG | 100 |
| 13: 95040142-95040222 | 13q32.1 | DZIP1 | ACTTCTCCAGTTGAAAGGGTATCCA | 101 | GGTAATGGAGACTCATGAATGACACT | 102 |
| 13: 114069879-114069968 | 13q34 | UPF3A | GCCTAGAATATCCTGCAGTGGTAGA | 103 | TGCTTCCAGTCTTGGCATCTTTT | 104 |
| 14: 24173173-24173244 | 14q12 | GZMB | GGAGGAAGGCCAGCAGAAG | 105 | ACAACAGCAGCTCCAACCA | 106 |
| 14: 34648789-34648863 | 14q13.2 | PPP2R3C | CAGCCTTTTCACCAACCTTCAAA | 107 | ACCAGACACCACCTATGATTGGA | 108 |
| 14: 72506044-72506141 | 14q24.2 | ZFYVE1 | GATAGGCGCACCAGGAATGA | 109 | CAGTGGCCAAACACGAATTAAAGT | 110 |
| 14: 104621601-104621710 | 14q32.33 |  | CATCCACTCACCACTGTATCCA | 111 | GGCATGAGGCTTGGAAGCA | 112 |
| 15: 33605950-33606033 | 15q14 | ATPBD4 | GAGCACCCACTGTGTACGA | 113 | ACACCAGCAGAATTATGCCATACTT | 114 |
| 15: 43667323-43667413 | 15q21.1 | PLDN | GGGATGGATTTACCAGAAAGATGATCAG | 115 | AGCTGACCAAGCATTTCATGAGT | 116 |
| 15: 77533137-77533242 | 15q25.1 | KIAA1024 | ACTCAGGCTTACCATATTTGTTTGTACTT | 117 | TGCATGGCAAAGGAAATCCCA | 118 |
| 15: 86971227-86971330 | 15q26.1 | AEN | AGGTGATAAATAGCTTACATTTTAGAGTTTGCT | 119 | CCATACCTGAACGTGATGCCA | 120 |
| 16: 31240261-31240341 | 16p11.2 | ITGAM | TGATGGTTTTCTGGTGTCCCTTTAG | 121 | CCACTTCCCTGGGATTGAACT | 122 |
| 16: 4814659-4814737 | 16p13.3 | N-PAC | GCCCAAGAGCCTGAGTTCT | 123 | CCGGGCCATCGATGAAGAG | 124 |
| 16: 56871110-56871184 | 16q21 | CCDC113 | CCATCGTAAGGCTTGGAATCGAA | 125 | GGCTACTTCCCAGCAAGGTAAT | 126 |
| 16: 85328817-85328925 | 16q24.1 | LOC729979 | GGTCCAGCCCTTCTCAACAC | 127 | ACCAGCACTCACCGCTAAA | 128 |
| 17: 8680592-8680671 | 17p13.1 | PIK3R6 | TCCTGGTAGGGATACAGCTCATT | 129 | GTCTGGTTTGCAGGGACACT | 130 |
| 17: 854262-854342 | 17p13.3 | ABR | GGCAGCCGATGGTCAGTA | 131 | GGCCTTGGGCAGAACAGTAAATA | 132 |
| 17: 45884445-45884521 | 17q21.33 | ACSF2 | CCCTCTGCTGGCACCTTTAAG | 133 | GCCCAGGTGGGACTGAGA | 134 |
| 17: 77723894-77723990 | 17q25.3 | CCDC57 | GCTTAGAGCCTCCATTTCTTTCCT | 135 | AGACTTTCCATCCAGTGAGATCCA | 136 |
| 18: 13731517-13731609 | 18p11.21 | RNMT | GATTGACAAATTTCGTGACCCACAA | 137 | TCAGCCTGCTCATAAGACTCAAATG | 138 |

TABLE 3-continued

Exemplary Targets and PCR Primers

| Chromosome location | Cytoband | Gene Symbol | Forward Primer | SEQ ID NO | Reverse Primer | SEQ ID NO |
|---|---|---|---|---|---|---|
| 18: 201348-201426 | 18p11.32 | USP14 | TCCAGAGCTTTAGAGGAAGACACAT | 139 | GTGGTCTGCTTCTGTCCTCTTTT | 140 |
| 18: 57674840-57674938 | 18q21.33 | RNF152 | TGCTGTCCTTACTCATTCCACATC | 141 | GCCTAAGTTTGCAGACCCTCAA | 142 |
| 18: 74964920-74964997 | 18q23 | ATP9B | GTGGTCCATATGGTCCCTTCTTAAA | 143 | AAAGGGACTCTTCCGGTTCTTG | 144 |
| 19: 17313717-17313790 | 19p13.11 | GTPBP3 | CCGTTCGACCCTTGATGCT | 145 | ACTACGAAACAAATATACTGAGATCCTCCT | 146 |
| 19: 14507730-14507818 | 19p13.12 | GPSN2 | GGTGACTCACTGGGCAGATTC | 147 | GAGTGCCTACAGCAAAGAAATGG | 148 |
| 19: 47551898-47551977 | 19q13.2 | MEGF8 | GCTCTGCCGATGTCCTCA | 149 | CAGTGTGGGCATTGCAGTTC | 150 |
| 19: 62959915-62960014 | 19q13.43 | ZNF776 | CAGTACTGGTGAGGGAAATCTGTT | 151 | TCCAGGCTTATAACGTAGGACACTA | 152 |
| 20: 13418983-13419079 | 20p12.1 | TASP1 | CCACTTCCCTCAATCATGTGACA | 153 | GGGTTTTGCCAACTTTTTCTGGATT | 154 |
| 20: 2311101-2311185 | 20p13 | TGM6 | GTGCGAAGGTTAGTTTCTGAGGAA | 155 | GAGAGGAACCCAGCAAGTTAGTT | 156 |
| 20: 34441093-34441175 | 20q11.23 | DLGAP4 | CCCATGGGAGATGCTCTTGA | 157 | GGTCTCCTGGTTCCATCTCTTC | 158 |
| 20: 42805126-42805219 | 20q13.12 | LOC100128040 | GCCCTGTCCCTGCTTCTG | 159 | AGGTGCCCCTTAGCCAGTA | 160 |
| 21: 27228739-27228824 | 21q21.3 | ADAMTS5 | CAGGCAGCTTCTTGGTCAGA | 161 | GTGTCCCGGCATGGATGT | 162 |
| 21: 32606313-32606415 | 21q22.11 | MRAP | AGCATCCTATGCCTTTGACAAAGA | 163 | CAGTAAGCAAGCAGGCTAGGT | 164 |
| 21: 32989371-32989464 | 21q22.11 | SYNJ1 | GTTCTGATTTCTACTCCTCCACACA | 165 | GGAATCAGTCTTTGCATTTGCATCT | 166 |
| 21: 38009196-38009283 | 21q22.13 | KCNJ6 | CTGATGTGTCTTGGCAGGTCAT | 167 | CCATGGATCAGGACGTCGAAAG | 168 |
| 22: 15964337-15964432 | 22q11.1 | IL17RA | CCTTACCCATCCCAACTAGCCTTA | 169 | GTAGAGTGAGTGTGACGTTGGAT | 170 |
| 22: 29154514-29154594 | 22q12.2 | MTP18 | CCTCCTGATCATACTCTGGTACCT | 171 | CACATTCCCTGGCAGGAGTAG | 172 |
| 22: 34452693-34452785 | 22q12.3 | APOL5 | CACATGAGGCTTTCGGAGGAATAA | 173 | CCTTGATGCCCTGGATAGCTTTTAC | 174 |
| 22: 48978363-48978457 | 22q13.33 | TRABD | CCATCCCTCTCCACAGCAA | 175 | GTCTGGGAACTCGCCAATCAT | 176 |
| X: 50512491-50512567 | Xp11.22 | SHROOM4 | GGAAATTGTCAGGTCAGCTCAGT | 177 | CCCATTTCATGTCCTCTCAGAAGAA | 178 |
| X: 24141606-24141705 | Xp22.11 | ZFX | TGCTTTAGGCAGGTGTGAACT | 179 | GGGCCAAGAAGGTACAGGAATTT | 180 |
| X: 109581619-109581695 | Xq22.3 | RGAG1 | CCCCATGGTCAACACAAAATGTAG | 181 | CATCACCCCAGAGGCTGTT | 182 |
| X: 123351536-123351615 | Xq25 | ODZ1 | GGTCAGAAAGTTACCAGGACTTGT | 183 | CCAGTGTCTGCAGTGGACAAAA | 184 |
| Y: 7271634-7271743 | Yp11.2 | PRKY | GTGATCTGAATGATGTTGAACAAGCA | 185 | ACACGGATAGCCAGACAATGAAATAC | 186 |
| Y: 5423177-5423278 | Yp11.2 | PCDH11Y | TCCTGCAAAATGACTTGAGTTGGTA | 187 | ACATGTCAGGCCTTTTTATTTTGTAGC | 188 |

TABLE 3-continued

Exemplary Targets and PCR Primers

| Chromosome location | Cytoband | Gene Symbol | Forward Primer | SEQ ID NO | Reverse Primer | SEQ ID NO |
|---|---|---|---|---|---|---|
| Y: 20211350-20211455 | Yq11.222 | CYorf15A | CTTCCAGGGAAATTCACCTCTTCT | 189 | GTTTCCCTGTTGAGAATGTTTCCAT | 190 |
| Y: 21330672-21330747 | Yq11.223 | RPS4Y2 | GAAAGGGAAGAGCACACAGTCT | 191 | GGCCTCAAAGTCCCACACAA | 192 |

TABLE 4

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| 1: 36669968-36670038 | 1p34.3 | C1orf102 | 1/2 | TCTTCCAAGACCTGCACATCCG | 193 | CCAGGGCTGCCTATTGACTTACTCGGATGTGCAGGTCTTGGAAGAAGATGAGGAGTGTCTGCCGGATCAGC | 289 |
| 1: 19882469-19882569 | 1p36.13 | TMCO4 | 3/4 | CAGGAGACAGTGAGTGAGCACC | 194 | CCCACGGCCTTCAGGATGGCATCCATCTGCTTGGCATAGTCCAGGTGGCCGCTGACCTGCAGGAGACAGTGAGTGAGCACCACCGTGGGTGTGCAGAGCC | 290 |
| 1: 176197341-176197427 | 1q25.2 | SEC16B | 5/6 | CCCCAGCTTCAGCAGCTTG | 195 | AACCCACCAGCCTGAACTGGACTCCAAGCTGCTGAAGCTGGGGATCATCCCGCTCCGGGCATCTCTGATGTACTGACTGAGCTCA | 291 |
| 1: 203386468-203386559 | 1q32.1 | DSTYK | 7/8 | CCGTGCCAAGATCACTGACTTA | 196 | CACAATGCTGCCTGACATCATGGCCTCTGGCTTGCAGAATCCTAAGTCAGTGATCTTGGCACGGTTCTGCTTATCCAGCTGCCAACAAGCA | 292 |
| 2: 51062327-51062418 | 2p16.3 | NRXN1 | 9/10 | AACCACCAACAAAGGGATTCT | 197 | TGACAGCTTTTGGCTCAGAAATTAGAAAATGAAATGATAACCACCAACAAAGGGATTCTGCAGCTGAGTATGGATTTCCTCCCAGTGACAGG | 293 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| 2: 27426789-27426880 | 2p23.3 | GTF3C2 | 11/12 | ACCTTCCC AGTTTGAT AAGCAC | 198 | CACGATGAG GGTTGAGGG AAAAACAGT TGGTAGGAA CAAGTGCTT ATCAAACTG GGAAGGTGC TCTTATTTA CAGCTGCTG GCTCAAGAA TC | 294 |
| 2: 141646278-141646366 | 2q22.1 | LRP1B | 13/14 | CTGGCCTG TGTGTACT TCT | 199 | GCCAGGATG CTCCATGTA GTATTGCAT TATAACATG GTCTCAGCT GGCCTGTGT GTACTTCTA CAACATGAA CCGTCAGAA TAATCCTT | 295 |
| 2: 166773406-166773515 | 2q24.3 | SCN9A | 15/16 | ACCCATGC CTCTTTCT AATAAC | 200 | AGGTGAAAA AAGTACTTA TGAGGATGA TGAATAGTT GGAAAAACT AGTAAAATA GGGTTGGTT ATTAGAAAG AGGCATGGG TAGTTGATA GAGCCATAA GCTTTGATC AA | 296 |
| 3: 71541265-71541358 | 3p14.1 | FOXP1 | 17/18 | CCTGCCTA CCAAAGAG GATACA | 201 | AAACAGGAG AATGAATGA ATGAATATG CTAATACAA CCACCTCTG TATCCTCTT TGGTAGGCA GGAGGCAAG AAGCAGGCT AATCTGTCT ATGG | 297 |
| 3: 51489723-51489813 | 3p21.2 | VPRBP | 19/20 | TCCCAGCC CACTGTAA ATG | 202 | GCCATCCTC CTTTTTCTC ATCCTGTGG GGCTACTTA TGATGTGAT GCCATTTAC AGTGGGCTG GGATTACAG GTGTGAGGC ACCAAACCC A | 298 |
| 3: 98908486-98908579 | 3q11.2 | EPHA6 | 21/22 | AATGCCAC CAGTGACC TTCAG | 203 | TGGCATGTG AGATGTGTT CAAGAAACT CAAGACTAA GGGAATGAA TGAATGAAT GCCACCAGT GACCTTCAG TGCCTCTCT AGTGGTACC CTTT | 299 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| 3: 142551967-142552067 | 3q23 | ZBTB38 | 23/24 | TCTTCTTTGCTCCTGAGACCTC | 204 | TCCCTCAAGTTTATTCAGTCTCCTTATGTAATCAGTAATTCTATCAAATCCTCTTCTTTGCTCCTGAGACCTCACCTACTTCAATTTGGACGTCTTGCTCT | 300 |
| 4: 46733909-46734018 | 4p12 | GABRB1 | 25/26 | ATAGGTGTCACTGTAAAGCAAC | 205 | CATTTCCAAGTACAGTAACTCCACAGTACTATCCTGTTGCTTTACAGGGACACCTATGCCTTTTTTATTCAGAATAAAGAACATTGCAAACTGTTTTTGCACCACTGAGG | 301 |
| 4: 6931464-6931545 | 4p16.1 | KIAA0232 | 27/28 | TCCTGCTGCCCACTGACCTG | 206 | CCCAAGCACCTGTAGCATCATCGTCCACGTCCTGCTGCCCACTGACCTGTCCGGCTCCACACATGAAGGCAGATGTTTGAGG | 302 |
| 4: 100651173-100651274 | 4q23 | C4orf17 | 29/30 | CCACACAGGCTCCTTGGAGTAA | 207 | GGAATGTTACCACGTTGCTAAGCTATGTAACATATCTTAACAACCAGGGAGCCACACAGGCTCCTTGGAGTAAGAGTGTGAGAAACTGGATGAAGACAGCTG | 303 |
| 4: 146906234-146906321 | 4q31.22 | ZNF827 | 31/32 | TTGCTGTTGGCTGAATCACT | 208 | TTTCTGGGAGCCATCTGAATCATCTTTGCTGTTGGCTGAATCACTCAGAGCTGAGAGGGAGGATGAAGAGGGGCTATTTGATTCGCTG | 304 |
| 5: 26772993-26773084 | 5p14.1 | LOC100131678 | 33/34 | AATGGAGAAGGGAAAATTAC | 209 | GGTATGACCTGGACACATTAAGCATTCGTAATTTTCCCTTCTCCATTACTAGATACAGTGCTTACATTTCTATTATTTTTATCTCCCTCT | 305 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| 5: 13791807-13791884 | 5p15.2 | DNAH5 | 35/36 | CAGGGAGACAAAACAGAAATAT | 210 | GCAAGCCACAGGAAGAGGAAGCCCAAAGGCAGGGAGACAAAACAGAAATATGCTTCTGGCACCAAGTCAAATTGTACA | 306 |
| 5: 108773400-108773485 | 5q21.3 | PJA2 | 37/38 | CCGGAGCCGCTGCACAT | 211 | GCGGAACAAGCCAGACTGAAAAAAAAAAAAAAAACCCTCACCGAAATGTGCAGCGGCTCCGGAGCGAGAACAGCGCTCGAACCTC | 307 |
| 5: 122258322-122258422 | 5q23.2 | SNX24 | 39/40 | CTAGGTACTGCGCCACTTTT | 212 | GTTTTAGAAGGAAGAGGGCTAGGAAGAAAAGTGGCGCAGTACCTAGTAGGTAAGTATAATCTGGATGCTCCCAGTAATTCTGAGTGTTGACTGCACATTCT | 308 |
| 6: 12970453-12970529 | 6p24.1 | PHACTR1 | 41/42 | ATGCAACTCATGCTGAATTTA | 213 | GTATAGGCAGCGACAGCACTTGTAAATTCAGCATGAGTTGCATGGTTGGCCAATGTTGGTGAGTCCTGTGGAGATCT | 309 |
| 6: 3672898-3672977 | 6p25.2 | C6orf145 | 43/44 | CCTCAAGCTCCGACCCCTCCT | 214 | GAAAACCAAAGCAACAAGGTGAGTCCTCAGGAGGGGTCGGAGCTTGAGGTTTTGGAGTTTGGAACTTACTCCCATCTCCC | 310 |
| 6: 74590195-74590286 | 6q13 | CD109 | 45/46 | CATGTATAGCTGCATAGATTTC | 215 | GGGTTGCAGGGATGGTGTACAACAGGTCCTAGCATGTATAGCTGCATAGATTTCTTCACCTGATCTTTGTGTGGAAGATCAGAATGAATGCA | 311 |
| 6: 112680120-112680214 | 6q21 | LAMA4 | 47/48 | CAGTCTGATGGTCCCAAGTTGA | 216 | GGGATCTGTAACTTGACCAAGGTCAAAGAGCTTGAAATTTCAACTTGGGACCATCAGACTGAA | 312 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| | | | | | | AACCTGCAATCTGAAACACTTTGCTGTGCTGC | |
| 7: 47936016-47936124 | 7p12.3 | PKD1L1 | 49/50 | CCACCCTTTCTACATTTCTCC | 217 | GATGGTATCTCCCACAAGTCACTACTTCCTGTGTTTTTGCGAAAAGCTCCCCGTGAGGGTGGGTGCCACCCTTTCTACATTTCTCCCTAGCTCCTTGTGCTGCAAATTG | 313 |
| 7: 40801751-40801837 | 7p14.1 | C7orf10 | 51/52 | TCCTTGCCAACTAGAAACTATG | 218 | CTGTCTGATTGTTAAGAGGGCTTGTATTCTCTTGAAAATCATAGTTTCTAGTTGGCAAGGAGCAAACTCCCAAGAACAAGTTGTGAC | 314 |
| 7: 99515052-99515140 | 7q22.1 | ZNF3 | 53/54 | AAAGAATCAGGCAGGTAAAGCT | 219 | GATAGATGGCCTGGCAGTAAGAACAAGACACGGAAAGCTTTACCTGCCTGATTCTTTCCTTCCTTCTTTGAAGTCAGTCCCTAGAAGGC | 315 |
| 7: 134591172-134591254 | 7q33 | STRA8 | 55/56 | ACGCTGGGCTATTTCATCATCT | 220 | TGAACCTTTGACACCTTCCCAAAACGCTGGGCTATTTCATCATCTTCTACAGTCTTCATCACCTTCGGTAATATTTGCTGTCA | 316 |
| 8: 12902405-12902494 | 8p22 | C8orf79 | 57/58 | CTTCCCCCAGCAAAGTTAGTTG | 221 | GATCTCCTCTTCTGTGCCTACATCAACTTCCCCCAGCAAAGTTAGTTGTATCTTTGTCTACTCAGTCTCATTTATGTTTTTGTCATCACA | 317 |
| 8: 10106677-10106775 | 8p23.1 | MSRA | 59/60 | CCACGGTCCACTCTGTCCACGT | 222 | GTTCTCTCTGGCCGTCAATATCTTAATGAAAGTGACATTCCGTTGGCCACGGTCCACTCTGTCCACGTGGAG | 318 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| | | | | | | GGCCGGGTT CCAGCCTCT GCAGAAGTG | |
| 8: 61648551-61648656 | 8q12.1 | RAB2A | 61/62 | ACAAGGCA AGACAGAG ATGTAC | 223 | GGGACCTGG GTTTCCTGA TACTTCCTA TGTGTCACA GTTTTCCCT TAAATGATA ACCGTACAT CTCTGTCTT GCCTTGTCC TTGAATTGT CCACTCGAC TCTGGGT | 319 |
| 8: 75439579-75439660 | 8q21.11 | GDAP1 | 63/64 | CTTTGACC TCAGTGTT AATTTT | 224 | TGGAGAGAA CCCCAGGCT TTATATGTA TACTTTGAC CTCAGTGTT AATTTTAAA TGCTTATGA ATCACACAC ATTGCTTTA G | 320 |
| 9: 26949592-26949694 | 9p21.2 | IFT74 | 65/66 | CTCCAGTC TCAACAGC CATTCC | 225 | AGATGGGAT CAAGGGTAA ATCAGAGTA AGATTGATC TTGAATGAG AGAAGGAAT GGCTGTTGA GACTGGAGG GCAGGATGG ATGTAGAGA AGTTTATGT GCCC | 321 |
| 9: 408149-408232 | 9p24.3 | DOCK8 | 67/68 | CCAAGGAA GACAGCAC TATTC | 226 | TGGCCATAG CAGGGAATA ATTTCAATT TGAAAACAA GTGGAATAG TGCTGTCTT CCTTGGTNT GTTGGTGCA CATGTGTCT GGT | 322 |
| 9: 78498063-78498161 | 9q21.13 | PRUNE2 | 69/70 | CTGCTGAG TAATTCAC TTTCCC | 227 | GGATGGGCA ATTTTAGGT AATCTCCAA TTGACCTAA CTCTAATGG AATGGGAAA GTGAATTAC TCAGCAGAT GACCACCAG GGTAGGTGC TTAAGAGAT | 323 |
| 9: 100023301-100023371 | 9q22.33 | TBC1D2 | 71/72 | CCTGCCCA GGAGCTAG TG | 228 | CCAGTGCCT TGTGCAGGA TCTTCACTA GCTCCTGGG CAGGGAGAG GGAAGAATC TTGTGAGCT CAGGGAGG | 324 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| 10: 17011452-17011533 | 10p13 | CUBN | 73/74 | ACAACCAGCCACATGGATTC | 229 | AAATAGAATATGAGACATGAGTAAATATGCCCTTTTATACAACCAGCCACATGGATTCTTTGTGGCACTGACTACAACTTGA | 325 |
| 10: 5401127-5401221 | 10p15.1 | UCN3 | 75/76 | CTGAGCAAGCATTTGATCCTGC | 230 | CAAAAGCTACAAGCCAGAGATACGATACAACAAGGACATTGCTCTGCAGGATCAAATGCTTGCTCAGATTTCCTGGTCTCTCTGTACATATGTGT | 326 |
| 10: 63195641-63195741 | 10q21.2 | C10orf107 | 77/78 | CTTCACAGACCGAGATAAACG | 231 | AAGACAATGTGCAGCAAAAGATAGCTCCATCATAACCACGTTTTTTATGATTGTCTTCACAGACCGAGATAAACGAAAAACTGCAAATACAGGAAGAGGCC | 327 |
| 10: 121323685-121323788 | 10q26.11 | LOC100133264 TIAL1 | 79/80 | TCGGTCTTCTGCATCTTCC | 232 | CAAATTTTACCCACACAGCCTGAAAAATACCTTGAAAGCAAACCTCGGTCTTCTGCATCTTCCAATTGATTCCTTTACAAACTCTGCACACATACAACTTAAGC | 328 |
| 11: 46730822-46730911 | 11p11.2 | CKAP5 | 81/82 | ACCCAACACAACAGCATTAAGT | 233 | AAAACAAGTAGGGCACTGGAAGAAAAACCCAACACAACAGCATTAAGTTTCAAACCTGCATTCCAATTAGAATCAGCAGTTGAAAGGGCA | 329 |
| 11: 6200897-6200970 | 11p15.4 | FAM160A2 | 83/84 | CAAGGGCTGGCACTCCCA | 234 | CATTGCAGAACTCCAGGGAACTCATGAAGAGTGCAAGGGCTGGCACTCCCAGCCAGTCTTCCCGTCGCAGACAG | 330 |
| 11: 62241048-62241147 | 11q12.3 | HNRNPUL2 | 85/86 | TTTCGGTTGTTTCGGCGATTTG | 235 | CCCCGGCTTCGGTTCTGCCGGTTACGC | 331 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| | | | | | | TTGTTTCGG TTGTTTCGG CGATTTGTC CGCTTCTCG GAGGGGGGC AGAAGCTTC CTTGCCTCC TCCTTGTAC T | |
| 11: 130999952-131000023 | 11q25 | NTM | 87/88 | ATCAGGCA GCCAGGAT TT | 236 | GGAATCCAG GAGGTGGTG ATGATCAGG CAGCCAGGA TTTCTGTCT CCACAGAGC ATACAGTTT AGTTGGCTG | 332 |
| 12: 27346341-27346426 | 12p11.23 | STK38L | 89/90 | ACCTCTTC ATCTGCTA ATCCTTC | 237 | AAGAAATTA GAAGTGGCC ATGGAAGAA GAAGGATTA GCAGATGAA GAGGTAATG TAATTACCT ATAATTACT GTACAAAAG CACCC | 333 |
| 12: 16036914-16037009 | 12p12.3 | DERA | 91/92 | CAGCCCAG CAAATGCA CACAT | 238 | CAGGTCAAT CTACTGCTA AGGGATTTC AGCCCAGCA AATGCACAC ATTAAGAAT AATGCCAGA ATGTAGAAA AGTGGCTTT ATCTTTCAG TAGCGG | 334 |
| 12: 42605583-42605676 | 12q12 | TMEM117 | 93/94 | CTGCGGGC TTTAGGAC TCCA | 239 | AGGCTGGTG GAGGCTAGT GCTCCGCCA CAGCTGCGG GCTTTAGGA CTCCACCTC GTCAGTCAT CCATGCCAA TGGTATGGT TTCCCAGGG TTTC | 335 |
| 12: 92044805-92044882 | 12q22 | LOC643339 | 95/96 | ACTTCCTA TGACAGCC AATCAC | 240 | CTTGGGATG TTTTATAAG TGTCTGTCT GTACTTCCT ATGACAGCC AATCACATC CAACCTATC CTCAGGTCC CTTCCC | 336 |
| 13: 19660225-19660311 | 13q12.11 | GJB2 | 97/98 | AAGCCATC ACTAGGAA CTTCT | 241 | TTGACATGA GGCCATTTG CTATCATAA GCCATCACT AGGAACTTC TAGTCTGTC TCACTCGAT | 337 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| | | | | | | TGAGGCTAC AATGTTGTT AGGTGC | |
| 13: 38442357-38442447 | 13q13.3 | STOML3 | 99/100 | TTGAGCCA GCAGAAAT GTT | 242 | AGATCTGGG ACAAGGTCT GTGTCCCTA AGACATTTC TCAGAGTGG TTTGAGCCA GCAGAAATG TTGCTTGAT GGACATCGT TGACATTAG C | 338 |
| 13: 95040142-95040222 | 13q32.1 | DZIP1 | 101/102 | CAGATCAG TGCAGTGT TTCTCA | 243 | ACTTCTCCA GTTGAAAGG GTATCCATT TGAGAAACA CTGCACTGA TCTGGAATA TAGTGTCAT TCATGAGTC TCCATTACC | 339 |
| 13: 114069879-114069968 | 13q34 | UPF3A | 103/104 | TTGCTCCA TTCCAGAA GATAGC | 244 | GCCTAGAAT ATCCTGCAG TGGTAGAGT TTGCTCCAT TCCAGAAGA TAGCCAAAA AGAAGCTGA GAAAAAAG ATGCCAAGA CTGGAAGCA | 340 |
| 14: 24173173-24173244 | 14q12 | GZMB | 105/106 | CTGAGAAG ATGCAACC AATCCT | 245 | GGAGGAAGG CCAGCAGAA GCAGGATTG GTTGCATCT TCTCAGGAA GGCTGCCCT GGTTGGAGC TGCTGTTGT | 341 |
| 14: 34648789-34648863 | 14q13.2 | PPP2R3C | 107/108 | AAGCGATG ATCAATTA CGAAAACT | 246 | CAGCCTTTT CACCAACCT TCAAAAAGT TTTCGTAAT TGATCATCG CTTCCTCTC CAATCATAG GTGGTGTCT GGT | 342 |
| 14: 72506044-72506141 | 14q24.2 | ZFYVE1 | 109/110 | CCGCCATA TACTTCCC TAAAGCT | 247 | GATAGGCGC ACCAGGAAT GACCGCCAT ATACTTCCC TAAAGCTCA ACCCACCCA CCAGTTCAG TTAAGAATT ATACTTTAA TTCGTGTTT GGCCACTG | 343 |
| 14: 104621601-104621710 | 14q32.33 | | 111/112 | TCTCCTCC CTTTGTTT TCCC | 248 | CATCCACTC ACCACTGTA TCCATCCAC CTCTCCTCC CTTTGTTTT | 344 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| | | | | | | CCCTACAAG CCCCACGTC CTGGGGGGC TGACTCCAA CTGGGGGTG CTGCTTCCA AGCCTCATG CC | |
| 15: 33605950-33606033 | 15q14 | ATPBD4 | 113/114 | ACGTGGCT CAGCACTG TATAC | 249 | GAGCACCCA CTGTGTACG AGTACACAA AGTGACCAC GTGGCTCAG CACTGTATA CAAATAAGT ATGGCATAA TTCTGCTGG TGT | 345 |
| 15: 43667323-43667413 | 15q21.1 | PLDN | 115/116 | ACGTCACC TCTCTGAA TTAT | 250 | GGGATGGAT TTACCAGAA AGATGATCA GCTTATAAT TCAGAGAGG TGACGTATC CTATAATAT TGACCACTC ATGAAATGC TTGGTCAGC T | 346 |
| 15: 77533137-77533242 | 15q25.1 | KIAA1024 | 117/118 | CTGGGCCT TGGTTTTC CA | 251 | ACTCAGGCT TACCATATT TGTTTGTAC TTCTTTTAT TCACTTCAG GAGACACTG GGCCTTGGT TTTCCAAAT AGGGTTTTT GACCTGGGA TTTCCTTTG CCATGCA | 347 |
| 15: 86971227-86971330 | 15q26.1 | AEN | 119/120 | CTGTGGGC TTTACAAA TTTTA | 252 | AGGTGATAA ATAGCTTAC ATTTTAGAG TTTGCTTTC TGTTATAAA AGTTGTACG CATTGATAT AAAATTGT AAAGCCCAC AGTGGCATC ACGTTCAGG TATGG | 348 |
| 16: 31240261-31240341 | 16p11.2 | ITGAM | 121/122 | ACTGAGAG TCAAGGCA ATCAT | 253 | TGATGGTTT TCTGGTGTC CCTTTAGGT CCCAGCCAG TACTGAGAG TCAAGGCAA TCATGGAGT TCAATCCCA GGGAAGTGG | 349 |
| 16: 4814659-4814737 | 16p13.3 | N-PAC | 123/124 | ACCATGTC CTCCTGTG TCCGTC | 254 | GCCCAAGAG CCTGAGTTC TCCTGAGAC GGACACAGG AGGACATGG | 350 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| | | | | | | TGAGATGAG AAGCTCCTC TTCATCGAT GGCCCGG | |
| 16: 56871110-56871184 | 16q21 | CCDC113 | 125/126 | CAACTGCT CATTGGTT ATTTTC | 255 | CCATCGTAA GGCTTGGAA TCGAATGAA AATAACCAA TGAGCAGTT GCAGGCAGA TTACCTTGC TGGGAAGTA GCC | 351 |
| 16: 85328817-85328925 | 16q24.1 | LOC729979 | 127/128 | AAGCCCTT GAGCCATC TTT | 256 | GGTCCAGCC CTTCTCAAC ACNGGAAAG CCCTTGAGC CATCTTTGA TTTGTGTGT TTTGATCTA ATTGCACTA CTGCTTGCA ATGCTTGTT TTTAGCGGT GAGTGCTGG T | 352 |
| 17: 8680592-8680671 | 17p13.1 | PIK3R6 | 129/130 | TTCGGCAA TGACCATC CTTTG | 257 | TCCTGGTAG GGATACAGC TCATTCGTC AAGTTCTGT TCGGCAATG ACCATCCTT TGGTACAGT GTCCCTGCA AACCAGAC | 353 |
| 17: 854262-854342 | 17p13.3 | ABR | 131/132 | CCTCTTGG GCATGTCT TTCCT | 258 | GGCAGCCGA TGGTCAGTA CTTCCTTCC TCTTGGGCA TGTCTTTCC TCCGTGCAC AGAGTATTT ACTGTTCTG CCCAAGGCC | 354 |
| 17: 45884445-45884521 | 17q21.33 | ACSF2 | 133/134 | CAGATAGG AGCCTTGA AGAAACA | 259 | CCCTCTGCT GGCACCTTT AAGGTGGGG CTGTGCTTT GTTTCTTCA AGGCTCCTA TCTGGTCTC AGTCCCACC TGGGC | 355 |
| 17: 77723894-77723990 | 17q25.3 | CCDC57 | 135/136 | TTGCGAAA CGCGATTG CCCA | 260 | GCTTAGAGC CTCCATTTC TTTCCTCAT CTGGGCAAT CGCGTTTCG CAAGCTCGT GTTCTGCTC TCGGAGCCG CTGGATCTC ACTGGATGG AAAGTCT | 356 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| 18: 13731517-13731609 | 18p11.21 | RNMT | 137/138 | ATGACAGACAAACTGACAACTGC | 261 | GATTGACAAATTTCGTGACCCACAAATGTGTTTTGACATCTGCAGTTGTCAGTTTGTCTGTCATTACTCATTTGAGTCTTATGAGCAGGCTGA | 357 |
| 18: 201348-201426 | 18p11.32 | USP14 | 139/140 | CAAATGAGGTGAAACATAAACCC | 262 | TCCAGAGCTTTAGAGGAAGACACATAGGTGGGTTTATGTTTCACCTCATTTGGAACAAAAGAGGACAGAAGCAGACCAC | 358 |
| 18: 57674840-57674938 | 18q21.33 | RNF152 | 141/142 | AAGATTGCTCGACCACCCCTCC | 263 | TGCTGTCCTTACTCATTCCACATCCTTACTAGAGGTGAGGGGTTGGGGGAGGGGTGGTCGAGCAATCTTTTGTACTTTTGAGGGTCTGCAAACTTAGGC | 359 |
| 18: 74964920-74964997 | 18q23 | ATP9B | 143/144 | TAGTGGTGAGAACACCCATCTTC | 264 | GTGGTCCATATGGTCCCTTCTTAAAGAAGATGGGTGTTCTCACCACTATTTACAGCCAAGAACCGGAAGAGTCCCTTT | 360 |
| 19: 17313717-17313790 | 19p13.11 | GTPBP3 | 145/146 | CCAACCCGGATGCCCC | 265 | CCGTTCGACCCTTGATGCTGGGGCATCCGGGTTGGGATGGAGATAGGAGGATCTCAGTATATTTGTTTCGTAGT | 361 |
| 19: 14507730-14507818 | 19p13.12 | GPSN2 | 147/148 | CAGGACAGAAGGGACTCCACC | 266 | GGTGACTCACTGGGCAGATTCTCCTGGTGGAGTCCCTTCTGTCCTGGCTGTAGCTTTGTACTTAGGCCATTTCTTTGCTGTAGGCACTC | 362 |
| 19: 47551898-47551977 | 19q13.2 | MEGF8 | 149/150 | CACTGCCGCATGGCTCT | 267 | GCTCTGCCGATGTCCTCAGGGCTGGGCTGGCCCACACTGCCGCATGGCTCTGTGTCCTGAGAA | 363 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| | | | | | | CTGCAATGC CCACACTG | |
| 19: 62959915-62960014 | 19q13.43 | ZNF776 | 151/152 | CAAGTCCT ACAGTGCA TTCATG | 268 | CAGTACTGG TGAGGGAAA TCTGTTCTC AAGTCCTAC AGTGCATTC ATGTGTCCT GAAGTCCAG AATTCTGTA GGATAGTGT CCTACGTTA TAAGCCTGG A | 364 |
| 20: 13418983-13419079 | 20p12.1 | TASP1 | 153/154 | CAGTGAAG CCACCTTT AAATCA | 269 | CCACTTCCC TCAATCATG TGACACCAC TTCAGTGAA GCCACCTTT AAATCATCT GTTTTTGAA TTTGTCTGG AATCCAGAA AAAGTTGGC AAAACCC | 365 |
| 20: 2311101-2311185 | 20p13 | TGM6 | 155/156 | AATGGGCA TCATCATC AACTTT | 270 | GTGCGAAGG TTAGTTTCT GAGGAAGGA AAAAGTTG ATGATGATG CCCATTGTC AGGTCTGTA ACTAACTTG CTGGGTTCC TCTC | 366 |
| 20: 34441093-34441175 | 20q11.23 | DLGAP4 | 157/158 | CCCACCAC CAGAATAG TCTTT | 271 | CCCATGGGA GATGCTCTT GAGAAAGAC TATTCTGGT GGTGGGTGC GGGATCCTG TCAGGGGA AGAGATGGA ACCAGGAGA CC | 367 |
| 20: 42805126-42805219 | 20q13.12 | LOC100128040 | 159/160 | CTGTGTGC AGATGTCG AAAAT | 272 | GCCCTGTCC CTGCTTCTG GAAAAAGAA TTTTCGACA TCTGCACAC AGACAGTTG TGAAAAAGG AGGAGAAGC AGCTACTGG CTAAGGGGC ACCT | 368 |
| 21: 27228739-27228824 | 21q21.3 | ADAMTS5 | 161/162 | CATCTGGC CCTGGCGT ACCA | 273 | CAGGCAGCT TCTTGGTCA GACAGACCA TCTGGCCCT GGCGTACCA CAGCACACC ACAGGCGAG CACAGACAT CCATGCCGG GACAC | 369 |

TABLE 4-continued

Exemplary Amplified Sequences

| Chromosome location | Gene Cytoband Symbol | Primer Pair SEQ ID NO) | Probe Sequence | Probe SEQ ID NO | Amplified Sequence (amplicon) | Amplicon SEQ ID NO |
|---|---|---|---|---|---|---|
| 21: 32606313-32606415 | 21q22.11 MRAP | 163/164 | CCAGGTGT TGCTGAGT TTAT | 274 | AGCATCCTA TGCCTTTGA CAAAGATTG CAGTGGCCC CTCGAGTGC AGAGGTCAT CCCAGGTGT TGCTGAGTT TATTGAGCA CACCTAGCC TGCTTGCTT ACTG | 370 |
| 21: 32989371-32989464 | 21q22.11 SYNJ1 | 165/166 | CACTATGG CGTGAATT GTG | 275 | GTTCTGATT TCTACTCCT CCACACATA AGACGTAAT AACCAGTCA TCACAATTC ACGCCATAG TGTTTGAGA TGCAAATGC AAAGACTGA TTCC | 371 |
| 21: 38009196-38009283 | 21q22.13 KCNJ6 | 167/168 | CCATTCAC CAGCCAAA GTT | 276 | CTGATGTGT CTTGGCAGG TCATCCCTG GCCTGCTTA GGCAACTTT GGCTGGTGA ATGGCCACT GGGCTTTCG ACGTCCTGA TCCATGG | 372 |
| 22: 15964337-15964432 | 22q11.1 IL17RA | 169/170 | CCCAGACC AGAAGAGT TCCAC | 277 | CCTTACCCA TCACACTCA GCCTTACCC ATCCTCGCC TCTCTCCTC AGCCCAGAC CAGAAGAGT TCCACCAGC GATCCAACG TCACACTCA CTCTAC | 373 |
| 22: 29154514-29154594 | 22q12.2 MTP18 | 171/172 | CTGTGCAT CGGCCTCC TGC | 278 | CCTCCTGAT CATACTCTG GTACCTGGC CTGTGCATC GGCCTCCTG CTTCATGTC AACCTCCTA CTCCTGCCA GGGAATGTG | 374 |
| 22: 34452693-34452785 | 22q12.3 APOL5 | 173/174 | CCAGCAGC CTCGATTT CAGAC | 279 | CACATGAGG CTTTCGGAG GAATAAATT GGTCTGAAA TCGAGGCTG CTGGCTTTT GTGTTAATA ANTGTGTAA AAGCTATCC AGGGCATCA AGG | 375 |
| 22: 48978363-48978457 | 22q13.33 TRABD | 175/176 | CTGCTTGC AGCGTTCC ACGTC | 280 | CCATCCCTC TCCACAGCA AGGATGACG | 376 |

TABLE 4-continued

Exemplary Amplified Sequences

| Chromosome location | Cytoband | Gene Symbol | Primer Pair SEQ ID NO) | Probe Sequence | Probe SEQ ID NO | Amplified Sequence (amplicon) | Amplicon SEQ ID NO |
|---|---|---|---|---|---|---|---|
| | | | | | | TGGAACGCT GCAAGCAGA AGGACCTAC TGGAGCAGA TGATGGCCG AGATGATTG GCGAGTTCC CAGAC | |
| X: 50512491-50512567 | Xp11.22 | SHROOM4 | 177/178 | ACAGGCCC CATTAATT TATG | 281 | GGAAATTGT CAGGTCAGC TCAGTGCCT ACAGGCCCC ATTAATTTA TGTCTCCTT CTTCTGAGA GGACATGAA ATGGG | 377 |
| X: 24141606-24141705 | Xp22.11 | ZFX | 179/180 | CCAAATGC CAGTCAAA GTCA | 282 | TGCTTTAGG CAGGTGTGA ACTCCAGCC CAAATGCCA GTCAAAGTC AAGGCATGG GTTTTCCTA GCCTATCTT ANAGGAAAT TCCTGTACC TTCTTGGCC C | 378 |
| X: 109581619-109581695 | Xq22.3 | RGAG1 | 181/182 | CACTGGCG GATTAGAC ATCATT | 283 | CCCCATGGT CAACACAAA ATGTAGACT CTGAAATGA TGTCTAATC CGCCAGTGA GAGCAACAG CCTCTGGGG TGATG | 379 |
| X: 123351536-123351615 | Xq25 | ODZ1 | 183/184 | ACCTTCCT CACCCAGA ATAA | 284 | GGTCAGAAA GTTACCAGG ACTTGTCTT GATACCTTA TTCTGGGTG AGGAAGGTC TTATTTTG TCCACTGCA GACACTGG | 380 |
| Y: 7271634-7271743 | Yp11.2 | PRKY | 185/186 | ACTCTCCT CCCTTTGC TTCTC | 285 | GTGATCTGA ATGATGTTG AACAAGCAT TATCAAAGA ATTCCACGA TGAGAAGCA AAGGGAGGA GAGTGGAAC TTTTGAAAA CCTGTATTT CATTGTCTG GCTATCCGT GT | 381 |
| Y: 5423177-5423278 | Yp11.2 | PCDH11Y | 187/188 | CAGGGCCA AGTAGTAA AGACCT | 286 | TCCTGCAAA ATGACTTGA GTTGGTAAA GTAGAAAGT TTTATGACT ACAAATTTC AGGGCCAAG | 382 |

TABLE 4-continued

Exemplary Amplified Sequences

| Chromosome location | Gene Cytoband Symbol | Primer Pair SEQ ID NO) | Probe Sequence | Probe SEQ ID NO | Amplified Sequence (amplicon) | Amplicon SEQ ID NO |
|---|---|---|---|---|---|---|
| | | | | | TAGTAAAGACCTGCTACAAAATAAAAAGGCCTGACATGT | |
| Y: 20211350-20211455 | Yq11.222 CYorf15A | 189/190 | AACTATACGATTTGAAACAAAATTC | 287 | CTTCCAGGGAAATTCACCTCTTCTATAGAAGAGTTTGTTTTGAACTATACGATTTGAAACAAAATTCTTTTTTTGGAGACTATGGAAACATTCTCAACAGGGAAAC | 383 |
| Y: 21330672-21330747 | Yq11.223 RPS4Y2 | 191/192 | CCGATATTGCTGGACCACCTCT | 288 | GAAAGGGAAGAGCACACAGTCTGTGTTAAGAGGTGGTCCAGCAATATCGGCAGGGCTTGTGTGGGACTTTGAGGCC | 384 |

Any of the exemplary loci shown in Table 3, or any other suitable target loci that are outside of a CNVR, can be used in the karyotyping methods described herein. Such target loci can also be combined with target loci that fall within a CNVR, if desired. Particular loci can be targeted on each chromosome and any such target loci can be combined with any other target loci to form a subset, or screening panel. For instance, any of SEQ ID NOS. 1-192 can be used to interrogate chromosomes 1-22, X or Y as shown below: SEQ ID NOS. 1, 2, 3, 4, 5, 6, 7, 8 (chromosome 1); SEQ ID NOS. 9, 10, 11, 12, 13, 14, 15, 16 (chromosome 2); SEQ ID NOS.: 17, 18, 19, 20, 21, 22, 23, 24 (chromosome 3); SEQ ID NOS. 25, 26, 27, 28, 29, 30, 31, 32 (chromosome 4), 33, 34, 35, 36, 37, 38, 39, 40 (chromosome 5); SEQ ID NOS. 41, 42, 43, 44, 45, 46, 47, 48 (chromosome 6); SEQ ID NOS. 49, 50, 51, 52, 53, 54, 55, 56 (chromosome 7); SEQ ID NOS. 57, 58, 59, 60, 61, 62, 63, 64 (chromosome 8); SEQ ID NOS. 65, 66, 67, 68, 69, 70, 71, 72 (chromosome 9); SEQ ID NOS. 73, 74, 75, 76, 77, 78, 79, 80 (chromosome 10); SEQ ID NOS. 81, 82, 83, 84, 85, 86, 87, 88 (chromosome 11); SEQ ID NOS. 89, 90, 91, 92, 93, 94, 95, 96 (chromosome 12); SEQ ID NOS. 97, 98, 99, 100, 101, 102, 103, 104 (chromosome 13); SEQ ID NOS. 105, 106, 107, 108, 109, 110, 111, 112 (chromosome 14); SEQ ID NOS. 113, 114, 115, 116, 117, 118, 119, 120 (chromosome 15); SEQ ID NOS. 121, 122, 123, 124, 125, 126, 127, 128 (chromosome 16); SEQ ID NOS. 129, 130, 131, 132, 133, 134, 135, 136 (chromosome 17); SEQ ID NOS. 137, 138, 139, 140, 141, 142, 143, 144 (chromosome 18); SEQ ID NOS. 145, 146, 147, 148, 149, 150, 151, 152 (chromosome 19); SEQ ID NOS. 153, 154, 155, 156, 157, 158, 159, 160 (chromosome 20); SEQ ID NOS. 161, 162, 163, 164, 165, 166, 167, 168 (chromosome 21); SEQ ID NOS. 169, 170, 171, 172, 173, 174, 175, 176 (chromosome 22); SEQ ID NOS. 177, 178, 179, 180, 181, 182, 183, 184 (X chromosome); or SEQ ID NOS. 185, 186, 187, 188, 189, 190, 191, 192 (Y chromosome). Typically, the primers are used in pairs as set forth in Tables 3 and 4. It is understood that other primers and primer pairs not listed in Tables 3 and 4 can be used to interrogate chromosomes or parts of chromosomes 1-22, X and Y. The probes (e.g., SEQ ID NOS. 193-288) are typically used to detect their corresponding amplified sequence (e.g., SEQ ID NOS. 289-384) (Table 4). When multiple chromosomes are interrogated, any of SEQ ID NOS. 1-192 can be used to interrogate their respective chromosomes. Any one or more of SEQ ID NOS. 1-192 can be used with any other one or more of SEQ ID NOS. 1-192 to perform such assays. For instance, any one or more of SEQ ID NOS. 1-8 can be used with any one or more of SEQ ID NOS. 9-16 to interrogate chromosomes 1 and 2, respectively. Other similar subsets of SEQ ID NOS. 1-192 can also be suitable for use, as would be contemplated by one of skill in the art. At least one additional locus can also be interrogated as a control (e.g., "control gene"). Such additional loci can be, for example, the aforementioned RNase P (chromosome 14, cytoband 14q11.2) or TERT (chromosome 5, cytoband 5p15.33).

In certain embodiments, the karyotyping methods described herein are used to simultaneously interrogate multiple chromosomes. For example, using a human gDNA sample, more than one chromosome (i.e., chromosomes 1-22, X and Y) can be simultaneously interrogated in the same or separate assays. Furthermore, a subset of the total complement of chromosomes can be interrogated in the same or separate assays. Individual chromosomes can be targeted by amplifying loci specific to such chromosomes that are outside of CNVRs. For example, chromosome 1 can be interrogated along with any one or more of chromosomes 2-22, X or Y; chromosome 2 can be interrogated along with any one or more of chromosomes 1 and 3-22, X or Y; chromosome 3 can be interrogated along with any one or more of chromosomes 1-2, 3-22, X or Y; chromosome 4 can be interrogated along with any one or more of chromosomes 1-3, 5-22, X or Y; chromosome 5 can be interrogated along with any one or more of chromosomes 1-4, 6-22, X or Y; chromosome 6 can be interrogated along with any one or more of chromosomes 1-5, 7-22, X or Y; chromosome 7 can be interrogated along with any one or more of chromosomes 1-6, 8-22, X or Y; chromosome 8 can be interrogated along with any one or more of chromosomes 1-7, 9-22, X or Y; chromosome 9 can be interrogated along with any one or more of chromosomes 1-8, 10-22, X or Y; chromosome 10 can be interrogated along with any one or more of chromosomes 1-9, 11-22, X or Y; chromosome 11 can be interrogated along with any one or more of chromosomes 1-10, 12-22, X or Y; chromosome 12 can be interrogated along with any one or more of chromosomes 1-11, 13-22, X or Y; chromosome 13 can be interrogated along with any one or more of chromosomes 1-12, 14-22, X or Y; chromosome 14 can be interrogated along with any one or more of chromosomes 1-13, 15-22, X or Y; chromosome 15 can be interrogated along with any one or more of chromosomes 1-14, 16-22, X or Y; chromosome 16 can be interrogated along with any one or more of chromosomes 1-15, 17-22, X or Y; chromosome 17 can be interrogated along with any one or more of chromosomes 1-16, 18-22, X or Y; chromosome 18 can be interrogated along with any one or more of chromosomes 1-17, 19-22, X or Y; chromosome 19 can be interrogated along with any one or more of chromosomes 1-18, 20-22, X or Y; chromosome 20 can be interrogated along with any one or more of chromosomes 1-19, 21, 22, X or Y; chromosome 21 can be interrogated along with any one or more of chromosomes 1-20, 22, X or Y; chromosome 22 can be interrogated along with any one or more of chromosomes 1-21, X or Y; X chromosome can be interrogated along with any one or more of chromosomes 1-22 or Y; Y chromosome can be interrogated along with any one or more of chromosomes 1-22 or X. Other subsets of chromosomes can also be interrogated as would be understood by one of skill in the art. For PCR-based assays, any of the primer sets shown in Tables 3 or 4 can be used as may any other suitable primer set.

Described herein are karyotyping methods for determining the copy number of one or more chromosomes in a test biological sample (such as a test gDNA). In certain embodiments, the methods can be used to determine the karyotype of a test genome. The karyotype information typically relates to one or more chromosomes of a genome.

Such methods described herein can be used in prenatal diagnostic assays to screen for and detect chromosomal abnormalities in a fetus or embryo, such as Down's Syndrome (Trisomy 21), Edward's Syndrome (Trisomy 18) and Patau Syndrome (Trisomy 13). These assays can be performed on biological samples such as fetal cells or cell-free fetal DNA in maternal blood, amniotic fluid, trophoblast cells, chorionic villus samples and percutaneous umbilical cord blood. Furthermore, the methods disclosed herein can also be performed on embryos used in in vitro fertilization (IVF) wherein blastocyst cells or cells biopsied from the trophectoderm are analyzed from embryos that are 3 to 6 days post-fertilization, in order to determine if they should be implanted in utero.

The methods described herein can be useful in, for example, stem cell analysis, quality control assays of cell cultures, analysis of samples of limited quantity (e.g. single cell, formalin-fixed paraffin-embedded (FFPE)), comparisons between cell or tissue types, comparisons between diseased or non-diseased tissues, detection of chromosomal polymorphisms, and the like. The methods disclosed herein can be used to compare chromosome copy number between, for example, cell types (e.g., lymphocyte, epithelial cell), tissue types (e.g., neural tissue, skeletal muscle tissue), disease states (e.g., cancerous, non-cancerous), or types of organisms (e.g. human, mouse, plant, fruit fly). Other uses for the methods described herein will be apparent to one of skill in the art.

The methods described herein can be used to detect chromosomal abnormalities. Exemplary abnormalities include, but are not limited to, deletion, duplication, translocation, mosaicism, aneuploidy (e.g., nullisomy, disomy, trisomy and tetrasomy), inversion, ring formation, isochromosome formation, or chromosomal instability syndromes. Pathologies have been associated with abnormalities in particular human chromosomes including, for example, chromosome 1 (e.g., acute lymphoblastic leukemia, acute megakaryoblastic leukemia, alveolar rhabdomyosarcoma), chromosome 2 (e.g., anaplastic large cell lymphoma, alveolar rhabdomyosarcoma), chromosome 3, chromosome 4 (e.g., Wolf-Hirschhorn syndrome, acute lymphoblastic leukemia), chromosome 5 (e.g., Cri du chat, also known as Chromosome 5q deletion syndrome, anaplastic large cell lymphoma), chromosome 6, chromosome 7 (e.g., Williams syndrome), chromosome 8 (e.g., Burkitt's lymphoma, acute lymphoblastic leukemia, acute myeloblastic leukemia with maturation), chromosome 9 (e.g., Trisomy 9, Warkany syndrome 2, acute lymphoblastic leukemia, Philadelphia chromosome), chromosome 10, chromosome 11 (e.g., Jacobsen syndrome, mantle cell lymphoma, multiple myeloma, acute lymphoblastic leukemia, Ewing's sarcoma, desmoplastic small round cell tumor), chromosome 12 (e.g., acute lymphoblastic leukemia, myxoid liposarcoma), chromosome 13 (e.g., Patau syndrome, alveolar rhabdomyosarcoma, breast and ovarian cancers, deafness, Wilson's disease), chromosome 14 (e.g., Burkitt's lymphoma, follicular lymphoma, acute lymphoblastic leukemia), chromosome 15 (e.g., Angelman syndrome, Prader-Willi syndrome, acute promyelocytic leukemia, Marfan syndrome, Tay-Sach's disease), chromosome 16 (e.g., Trisomy 16, myxoid liposarcoma, polycystic kidney disease, α-thalassemia), chromosome 17 (e.g., Miller-Dieker syndrome, Smith-Magenis syndrome, acute promyelocytic leukemia, dermatofibrosarcoma protuberans, Charcot-Marie-Tooth disease), chromosome 18 (e.g., Edwards syndrome, Burkitt's lymphoma, follicular lymphoma, mantle cell lymphoma, multiple myeloma, synovial sarcoma, Nieman-Pick disease, pancreatic cancer), chromosome 19 (e.g., acute lymphoblastic leukemia), chromosome 20, chromosome 21 (e.g., Down syndrome, acute lymphoblastic leukemia, acute myeloblastic leukemia with maturation), chromosome 22 (e.g., Di George's syndrome, Trisomy 22, acute lymphoblastic leukemia, Philadelphia chromosome, acute megakaryoblastic leukemia, Ewing's sarcoma, dermatofibrosarcoma protuberans, desmoplastic small round cell tumor), X chromosome (e.g., Fragile X syndrome, Turner syndrome, Triple X syndrome, Klinefelter's syndrome, synovial sarcoma, mixed gonadal dysgenesis, XX gonadal dysgenesis, uniparental disomy, Duchenne muscular dystrophy, X-linked diseases, hemophilia, adrenoleukodystrophy, Hunter's disease), or Y chromosome (e.g., Klinefelter's syndrome, uniparental disomy, acute myeloid leukemia). Any of these disorders, or any other disorders that may be detected by karyotyping as would be known by the skilled artisan, can be studied using the methods described herein.

Kits for determining the copy number of multiple chromosomes are also provided. For use with a PCR-based assay, the kit can include at least a set of primers for amplifying at least one test locus on a chromosome (e.g., any one or more of SEQ ID NOS. 1-192) or corresponding probes (e.g., any one or more of SEQ ID NOS. 193-288). The kit can also include samples of pre-determined amplified sequences such as those listed in Table 4 (e.g., any one or more of SEQ ID NOS. 289-384), which can optionally be affixed to a solid support (e.g. a membrane, glass slide, multi-well plate) for use as a control reaction. The kit can also optionally include stock solutions, buffers, enzymes, detectable labels or reagents required for detection, tubes, membranes, and the like that can be used to complete the amplification reaction. In some embodiments, multiple primer sets are included. The kits can also comprise the reagents required to use a reference (e.g., primers and probes for amplifying or detecting a reference sequence such as RNase P or TERT) or calibrator sample (i.e., a control genome of known karyotype, a chromosome sample, or the like). In some embodiments, the kits can contain multiple sets of primers for amplifying multiple target loci on a single chromosome or among two or more chromosomes (e.g., any combination of primers sets and probes shown in Tables 3 and 4, or any primer/probe sets that target loci outside of CNVRs). In one embodiment, a multi-well plate contains within its wells an array of replicate wells for use in carrying out assays. For example, a 384-well array containing four replicate wells for each of chromosomes 1-22, X and Y comprising primer/probe sets targeting loci outside of CNVRs for each of the chromosomes, is provided, optionally including reagents such as stock solutions, buffers, enzymes such as polymerases, and detectable labels. Other embodiments of particular systems and kits are also contemplated which would be understood by one of skill in the art. In addition, the arrays can be customized depending on the target samples being analyzed, for example, arrays comprising one, two, three or more chromosomes comprising one, two, or more than two loci to be analyzed per chromosome. Furthermore, the number of replicate wells or samples per chromosome per array can vary (e.g., one, two, three, four, or more than four).

All references cited within this disclosure are hereby incorporated by reference in their entirety. Certain embodiments are further described in the following examples. These embodiments are provided as examples only and are not intended to limit the scope of the claims in any way.

EXAMPLES

A. Karyotyping of Chromosomes 2, 3, 4, 5, 6, 20 and 22

The primers and probes used to interrogate the targets of interest described below were designed using masked genomic DNA sequences (the human genome assembly B36) by an Applied Biosytems proprietary TaqMan® Copy Number Assay Design Pipeline. The existing pre-designed TaqMan® copy number assay protocols were utilized. TaqMan® copy number assays targeting chromosomal regions located outside of copy number variable regions (CNVR) on each of the 24 chromosomes were designed (the data shown below, however, relates only to chromosomes 2, 3, 4, 5, 6, 20 and 22.) As described above, to cover all 24 chromosomes on a 384 well plate or TaqMan® array card (TLDA), four assays can be selected for each chromosome, using two assays on each arm of each chromosome whenever possible. The assays were run as duplex TaqMan® real-time PCR reactions. A FAM™ dye-based assay was used to detect test target loci and the VIC® dye-based assay was used for the reference locus RNase P (PN 4316844 from Applied Biosystems). Each assay utilized 10 ng gDNA, 1× TaqMan® probe/primer mix (900 nM of each primer, 250 nM of each probe) in 1× TaqMan® Genotyping Master Mix in a 10 µl reaction (run in quadruplicate). PCR reactions were incubated in an Applied Biosystems 7900HT SDS instrument for 10 minutes at 95° C., followed by 40 cycles of 15 seconds at 95° C. and 60 seconds at 60° C. Real-time data was collected by the SDS 2.3 software. The relative quantification analysis was performed to calculate estimated copy number of each sample for the gene of interest by CopyCaller™ software.

These methods were used to interrogate loci on chromosomes 2, 3, 4, 5, 6, 20 and 22 of human gDNA samples (a set of 92 African American and Caucasian gDNA samples from Coriell Institute) using the following primer sets and probes:

TABLE 5

| Chromosome | SEQ ID NO. (primer pairs) | Probe | SEQ ID NO. (probe) | Amplified sequence (amplicon) | SEQ ID NO. (amplicon) |
| --- | --- | --- | --- | --- | --- |
| 2 | 9/10 | AACCACCA ACAAAGGG ATTCT | 197 | TGACAGCTTTTGGCTCAGAAAT TAGAAAATGAAATGATAACCAC CAACAAAGGGATTCTGCAGCTG AGTATGGATTTCCTCCCAGTGA CAGG | 293 |
|  | 11/12 | ACCTTCCC AGTTTGAT AAGCAC | 198 | CACGATGAGGGTTGAGGGAAAA ACAGTTGGTAGGAACAAGTGCT TATCAAACTGGGAAGGTGCTCT TATTTACAGCTGCTGGCTCAAG AATC | 294 |
|  | 13/14 | CTGGCCTG TGTGTACT TCT | 199 | GCCAGGATGCTCCATGTAGTAT TGCATTATAACATGGTCTCAGC TGGCCTGTGTGTACTTCTACAA CATGAACCGTCAGAATAATCCT T | 295 |
|  | 15/16 | ACCCATGC CTCTTTCT AATAAC | 200 | AGGTGAAAAAAGTACTTATGAG GATGATGAATAGTTGGAAAAAC TAGTAAAATAGGGTTGGTTATT AGAAAGAGGCATGGGTAGTTGA TAGAGCCATAAGCTTTGATCAA | 296 |

TABLE 5-continued

| Chromosome | SEQ ID NO. (primer pairs) | Probe | SEQ ID NO. (probe) | Amplified sequence (amplicon) | SEQ ID NO. (amplicon) |
|---|---|---|---|---|---|
| 3 | 17/18 | CCTGCCTACCAAAGAGGATACA | 201 | AAACAGGAGAATGAATGAATGAATATGCTAATACAACCACCTCTGTATCCTCTTTGGTAGGCAGGAGGCAAGAAGCAGGCTAATCTGTCTATGG | 297 |
|  | 19/20 | TCCCAGCCCACTGTAAATG | 202 | GCCATCCTCCTTTTTCTCATCCTGTGGGGCTACTTATGATGTGATGCCATTTACAGTGGGCTGGGATTACAGGTGTGAGGCACCAAACCCA | 298 |
|  | 21/22 | AATGCCACCAGTGACCTTCAG | 203 | TGGCATGTGAGATGTGTTCAAGAAACTCAAGACTAAGGGAATGAATGAATGCCACCAGTGACCTTCAGTGCCTCTCTAGTGGTACCCTTT | 299 |
|  | 23/24 | TCTTCTTTGCTCCTGAGACCTC | 204 | TCCCTCAAGTTTATTCAGTCTCCTTATGTAATCAGTAATTCTATCAAATCCTCTTCTTTGCTCCTGAGACCTCACCTACTTCAATTTGGACGTCTTGCTCT | 300 |
| 4 | 25/26 | ATAGGTGTCCCTGTAAAGCAAC | 205 | CATTTCCAAGTACAGTAACTCCACAGTACTATCCTGTTGCTTTACAGGGACACCTATGCCTTTTTTCTTCAGAATAAAGAACATTGCAAACTGTTTTTGCACCACTGAGG | 301 |
|  | 27/28 | TCCTGCTGCCCACTGACCTG | 206 | CCCAAGCACCTGTAGCATCATCGTCCACGTCCTGCTGCCCACTGACCTGTCCGGCTCCACACATGAAGGCAGATGTTTGAGG | 302 |
|  | 29/30 | CCACACAGGCTCCTTGGAGTAA | 207 | GGAATGTTACCACGTTGCTAAGCTATGTAACATATCTTAACAACCAGGGAGCCACACAGGCTCCTTGGAGTAAGAGTGTGAGAAACTGGATGAAGACAGCTG | 303 |
|  | 31/32 | TTGCTGTTGGCTGAATCACT | 208 | TTTCTGGGAGCCATCTGAATCATCTTTGCTGTTGGCTGAATCACTCAGAGCTGAGAGGGAGGATGAGAGGGGCTATTTGATTCGCTG | 304 |
| 5 | 33/34 | AATGGAGAAGGGAAAATTAC | 209 | GGTATGACCTGGACACATTAAGCATTCGTAATTTTCCCTTCTCCATTACTAGATACAGTGCTTACATTTCTCATTATTTTATCTCCCTCCT | 305 |
|  | 35/36 | CAGGGAGACAAAACAGAAATAT | 210 | GCAAGCCACAGGAAGAGGAAGCCCAAAGGCAGGGAGACAAAACAGAAATATGCTTCTGGCACCAAGTCAAATTGTACA | 306 |
|  | 37/38 | CCGGAGCCGCTGCACAT | 211 | GCGGAACAAGCCAGACTGAAAAAAAAAAAAAAACCCTCACCGAAATGTGCAGCGGCTCCGGAGCGAGAACAGCGCTCGAACCTC | 307 |
|  | 39/40 | CTAGGTACTGCGCCACTTTT | 212 | GTTTTAGAAGGAAGAGGGCTAGGAAGAAAAGTGGCGCAGTACCTAGTAGGTAAGTATAATCTGGATGCTCCCAGTAATTCTGAGTGTTGACTGCACATTCT | 308 |
| 6 | 41/42 | ATGCAACTCATGCTGAATTTA | 213 | GTATAGGCAGCGACAGCACTTGTAAATTCAGCATGAGTTGCATGGTTGGCCAATGTTGGTGAGTCCTGTGGAGATCT | 309 |

TABLE 5-continued

| Chromosome | SEQ ID NO. (primer pairs) | Probe | SEQ ID NO. (probe) | Amplified sequence (amplicon) | SEQ ID NO. (amplicon) |
|---|---|---|---|---|---|
| | 43/44 | CCTCAAGC TCCGACCC CTCCT | 214 | GAAAACCAAAGCAACAAGGTGA GTCCTCAGGAGGGGTCGGAGCT TGAGGTTTTGGAGTTTGGAACT TACTCCCATCTCCC | 310 |
| | 45/46 | CATGTATA GCTGCATA GATTTC | 215 | GGGTTGCAGGGATGGTGTACAA CAGGTCCTAGCATGTATAGCTG CATAGATTTCTTCACCTGATCT TTGTGTGGAAGATCAGAATGAA TGCA | 311 |
| | 47/48 | CAGTCTGA TGGTCCCA AGTTGA | 216 | GGGATCTGTAACTTGACCAAGG TCAAAGAGCTTGAAATTTCAAC TTGGGACCATCAGACTGAAAAC CTGCAATCTGAAACACTTTGCT GTGCTGC | 312 |
| 20 | 153/154 | CAGTGAAG CCACCTTT AAATCA | 269 | CCACTTCCCTCAATCATGTGAC ACCACTTCAGTGAAGCCACCTT TAAATCATCTGTTTTTGAATTT GTCTGGAATCCAGAAAAGTTG GCAAAACCC | 365 |
| | 155/156 | AATGGGCA TCATCATC AACTTT | 270 | GTGCGAAGGTTAGTTTCTGAGG AAGGAAAAAGTTGATGATGAT GCCCATTGTCAGGTCTGTAACT AACTTGCTGGGTTCCTCTC | 366 |
| | 157/158 | CCCACCAC CAGAATAG TCTTT | 271 | CCCATGGGAGATGCTCTTGAGA AAGACTATTCTGGTGGTGGGTG CGGGATCCTGTCAGGGGGAAGA GATGGAACCAGGAGACC | 367 |
| | 159/160 | CTGTGTGC AGATGTCG AAAAT | 272 | GCCCTGTCCCTGCTTCTGGAAA AAGAATTTTCGACATCTGCACA CAGACAGTTGTGAAAAAGGAGG AGAAGCAGCTACTGGCTAAGGG GCACCT | 368 |
| 22 | 169/170 | CCCAGACC AGAAGAGT TCCAC | 277 | CCTTACCCATCCCAACTAGCCT TACCCATCCTCGCCTCTCTCCT CAGCCCAGACCAGAAGAGTTCC ACCAGCGATCCAACGTCACACT CACTCTAC | 373 |
| | 171/172 | CTGTGCAT CGGCCTCC TGC | 278 | CCTCCTGATCATACTCTGGTAC CTGGCCTGTGCATCGGCCTCCT GCTTCATGTCAACCTCCTACTC CTGCCAGGGAATGTG | 374 |
| | 173/174 | CCAGCAGC CTCGATTT CAGAC | 279 | CACATGAGGCTTTCGGAGGAAT AAATTGGTCTGAAATCGAGGCT GCTGGCTTTTGTGTTAATAANT GTGTAAAAGCTATCCAGGGCAT CAAGG | 375 |
| | 175/176 | CTGCTTGC AGCGTTCC ACGTC | 280 | CCATCCCTCTCCACAGCAAGGA TGACGTGGAACGCTGCAAGCAG AAGGACCTACTGGAGCAGATGA TGGCCGAGATGATTGGCGAGTT CCCAGAC | 376 |

Figure 2:
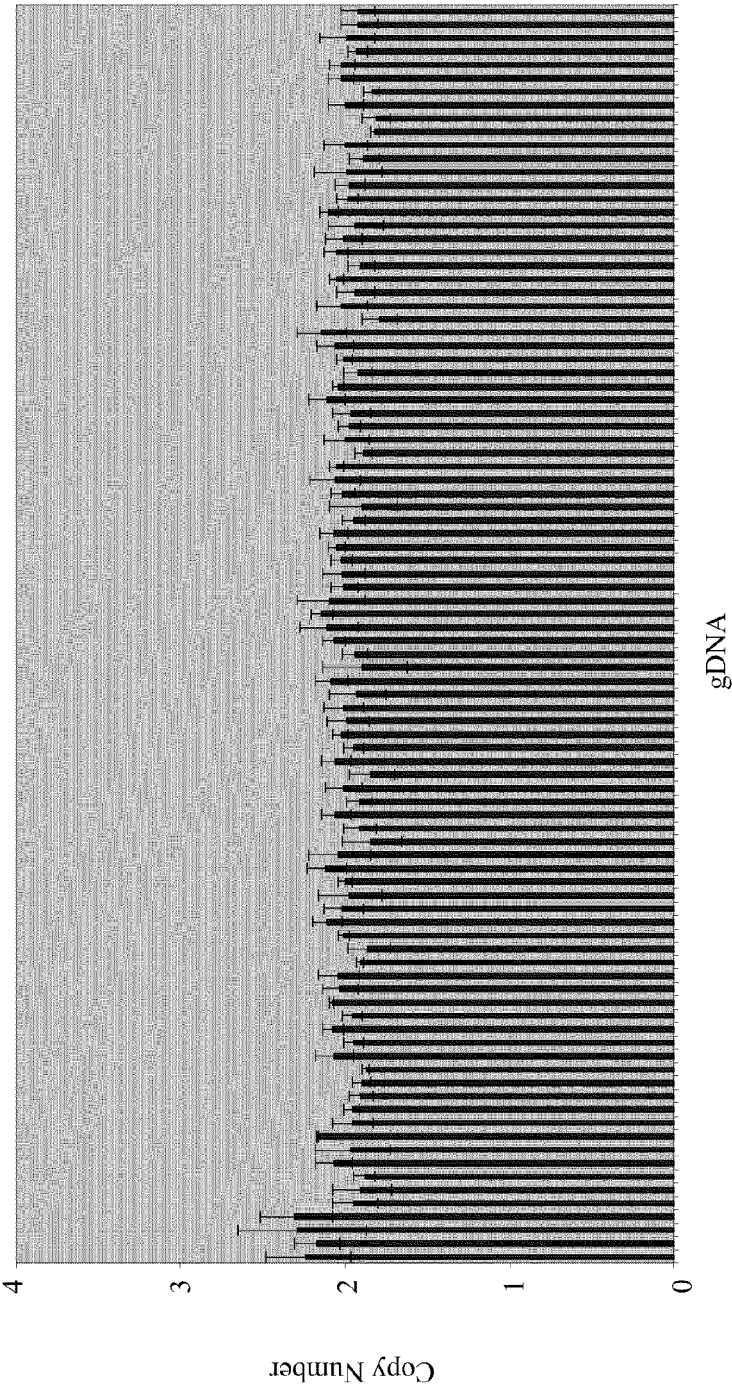
FIG. 2. Results of exemplary assay of chromosome 3.
Figure 3:
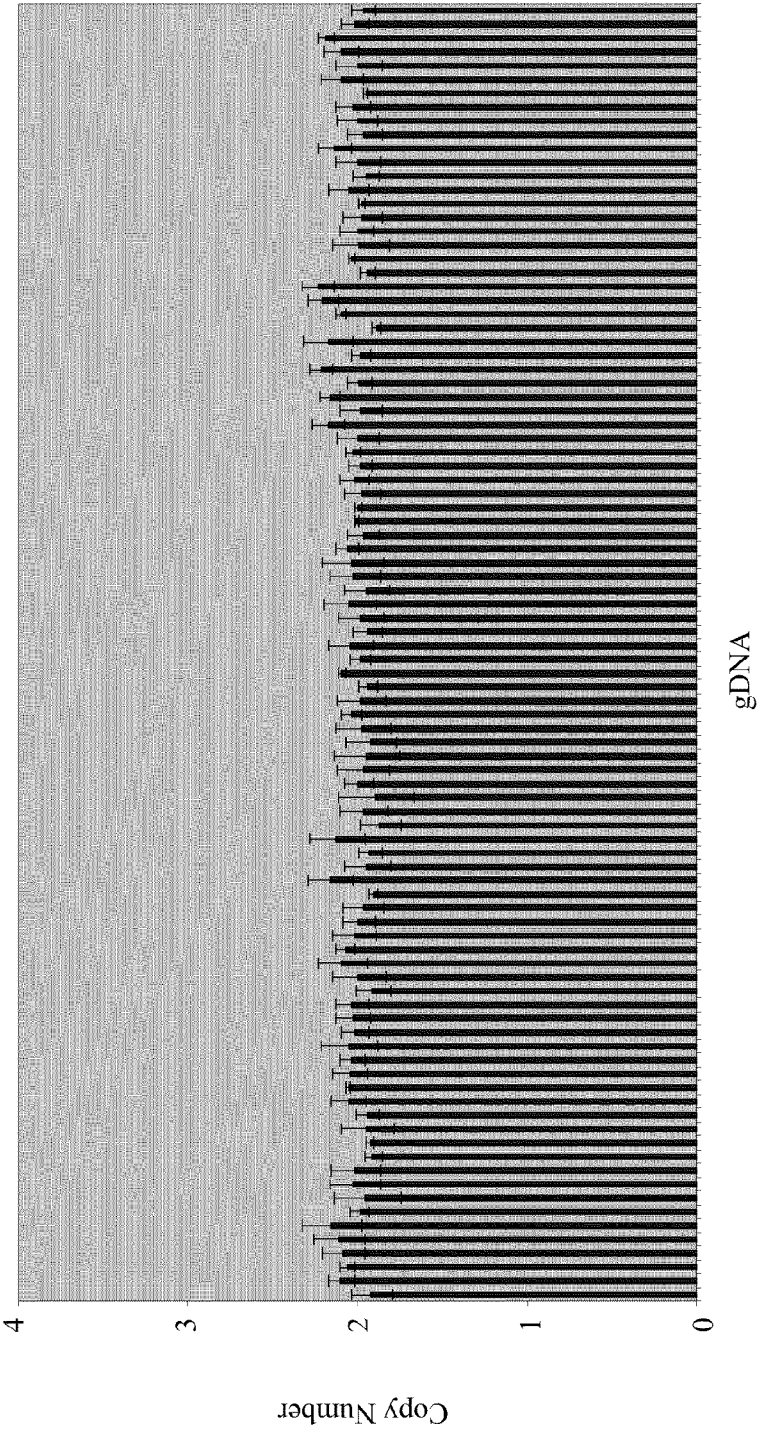
FIG. 3. Results of exemplary assay of chromosome 4.
Figure 4:
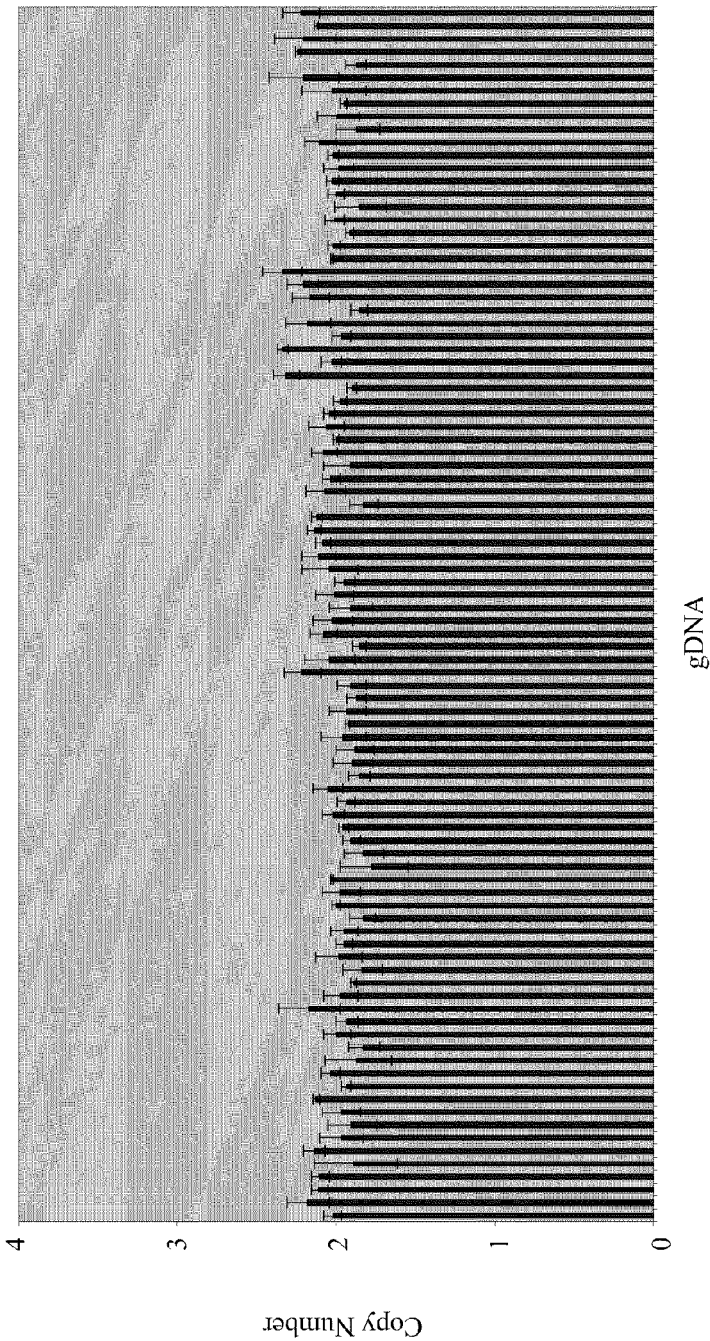
FIG. 4. Results of exemplary assay of chromosome 5.
Figure 5:
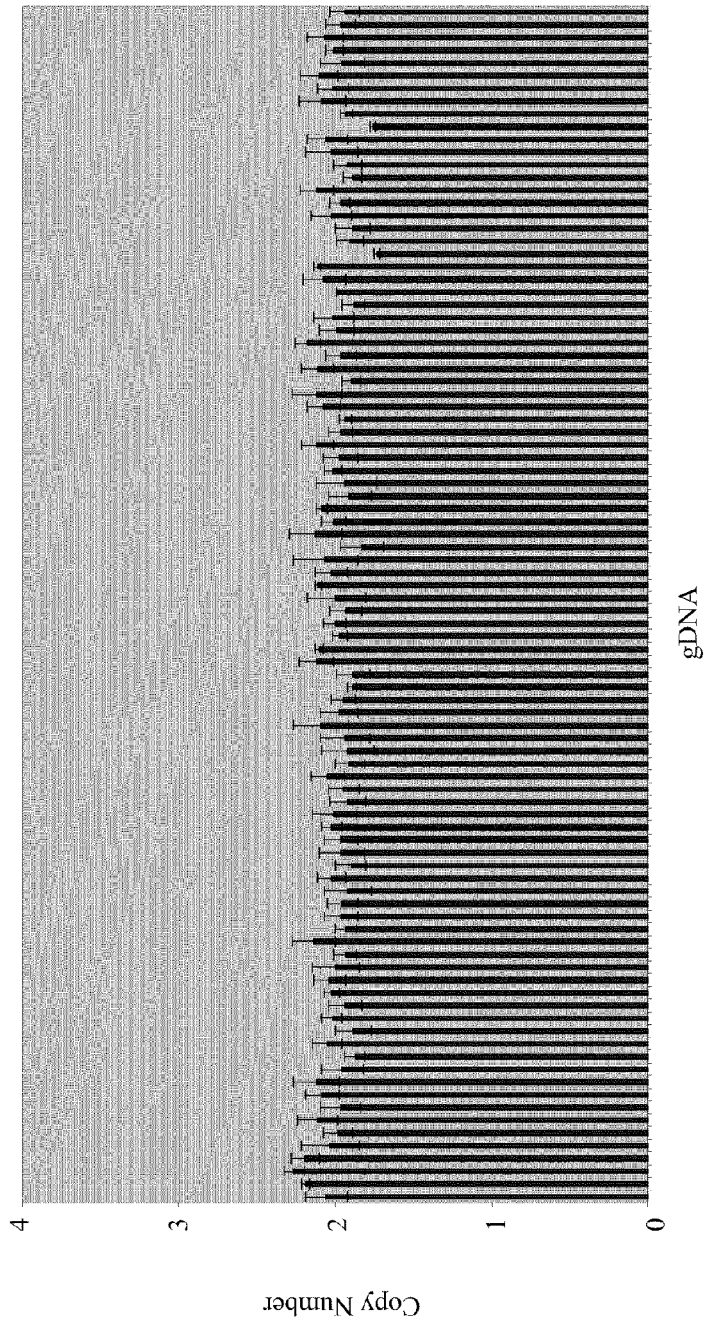
FIG. 5. Results of exemplary assay of chromosome 6.
Figure 6:
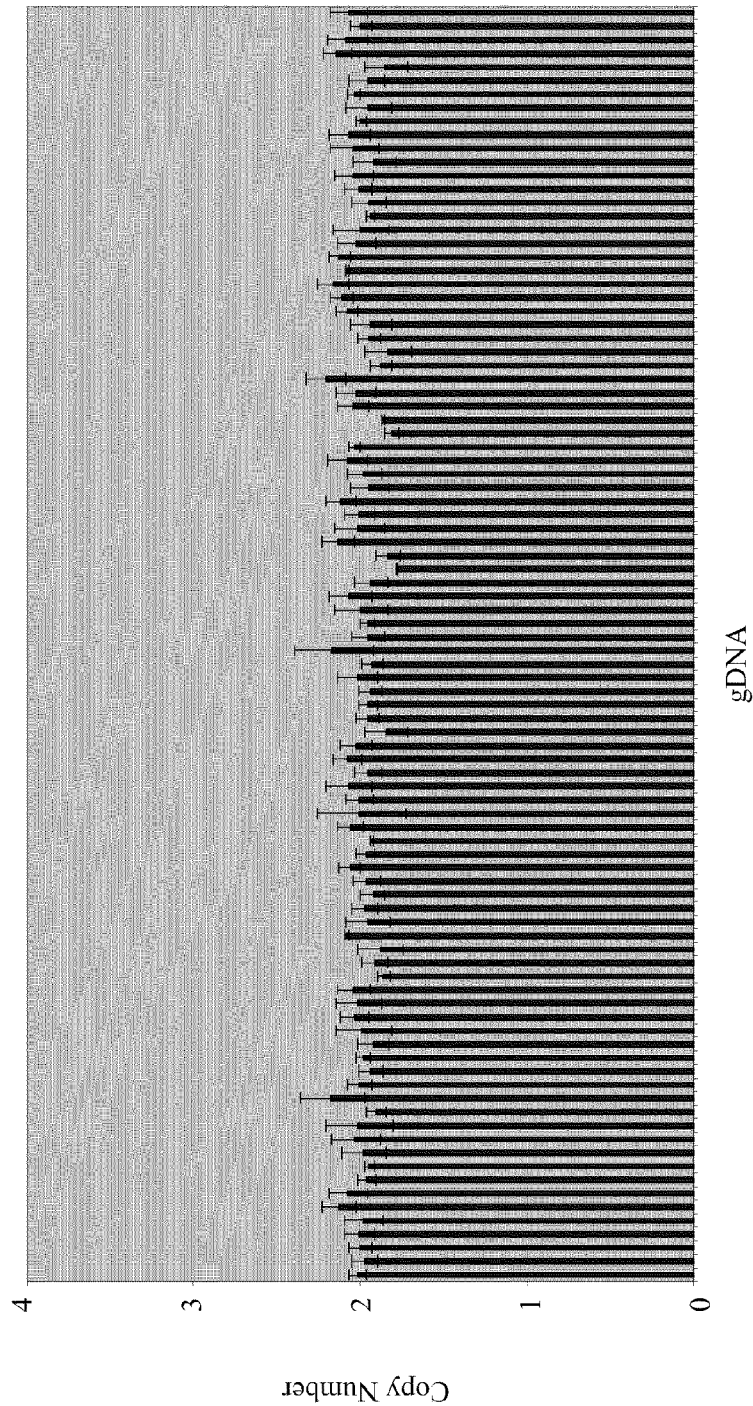
FIG. 6. Results of exemplary assay of chromosome 20.
Figure 7:
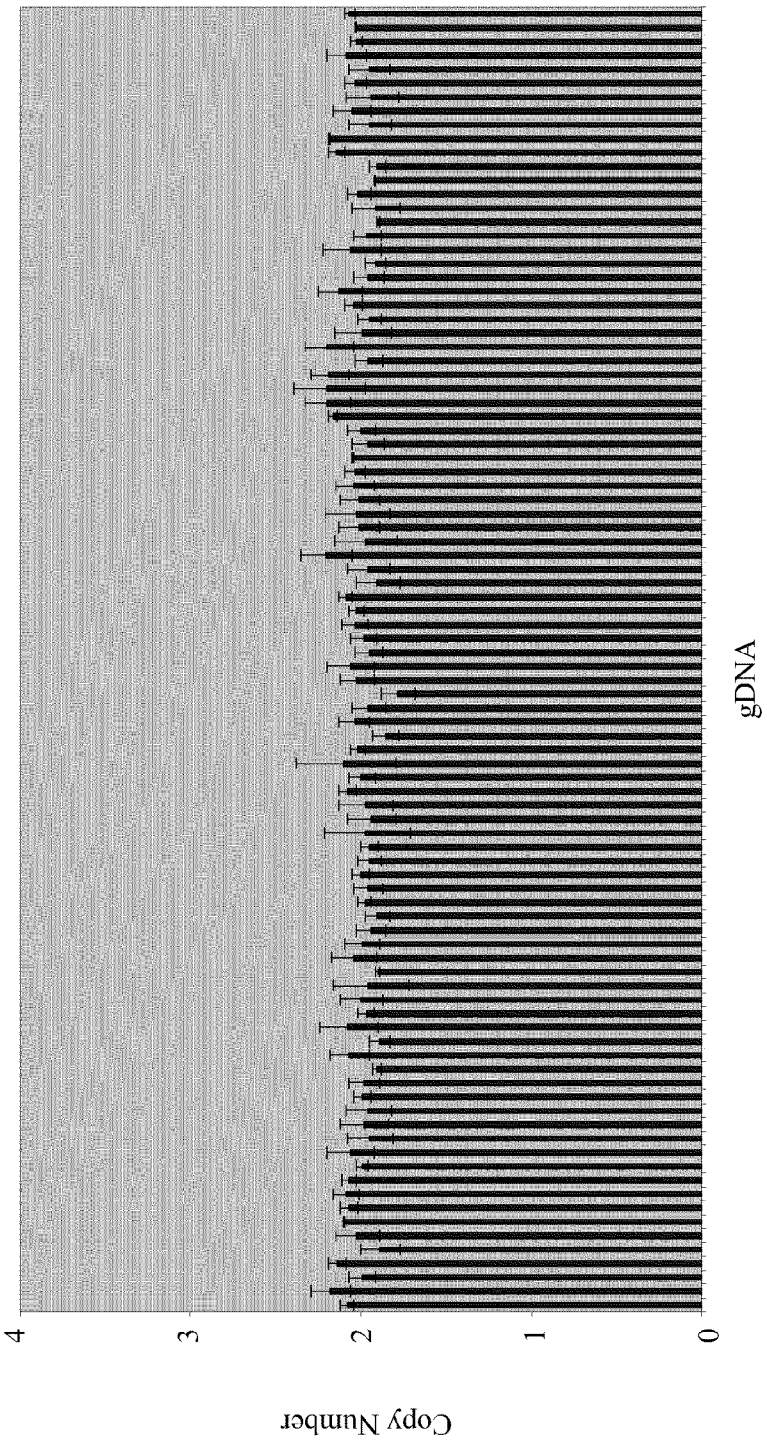
FIG. 7. Results of additional exemplary assay of chromosome 20.
Figure 8:
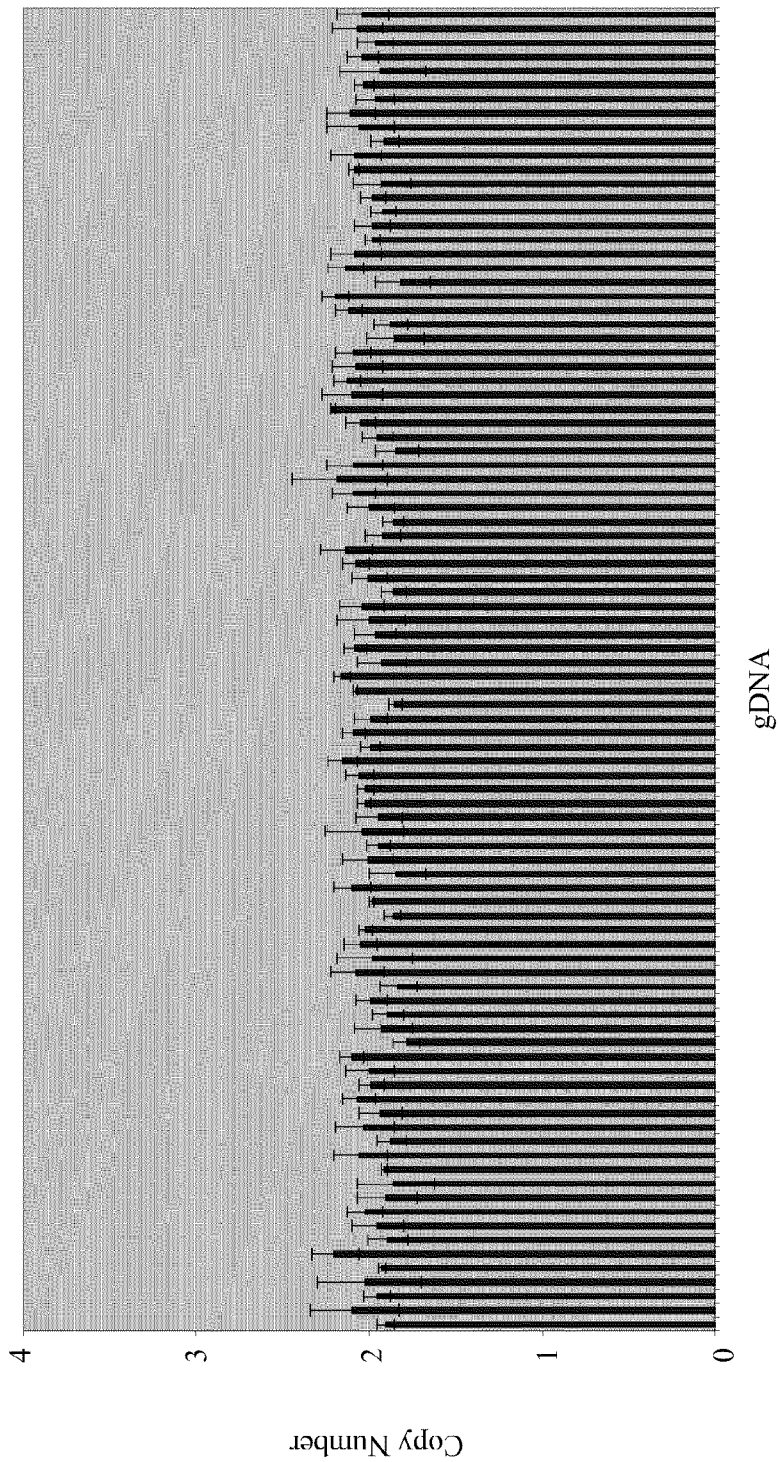
FIG. 8. Results of exemplary assay of chromosome 22.

The resultant data is shown in FIG. 1 (chromosome 2), FIG. 2 (chromosome 3), FIG. 3 (chromosome 4), FIG. 4 (chromosome 5), FIG. 5 (chromosome 6), FIG. 6 (chromosome 20), FIG. 7 (chromosome 20), and FIG. 8 (chromosome 22). As shown therein, the methods described herein (e.g., interrogating target loci located outside CNVRs) has been used to accurately karyotype various chromosomes found within the human genome.

B. Detection of Disease Pathology by Karyotype Analysis

Many forms of cancer have been associated with various chromosomal abnormalities (see discussion hereinabove). Detection of diseases or susceptibility to diseases is critical for proper diagnosis or treatment. For example, certain breast and ovarian cancers are associated with abnormalities in chromosome 13. Primers and probes useful for interrogation of non-CNVR loci of chromosome 13 can be used to determine whether a patient has or is susceptible to having a breast or ovarian cancer.

The primers and probes used to interrogate the chromosome 13 target loci are designed using masked genomic DNA sequences (the human genome assembly B36) by an Applied Biosystems proprietary TaqMan® Copy Number Assay Design Pipeline and interrogated using copy number assays of format 1 and using virtual calibrator assay no. 1. Test samples are obtained from normal and tumor cell and tissue. As described above, four assays are selected for chromosome 13, using two assays on each arm of the chromosome. The assays are run as duplex TaqMan® real-time PCR reactions. A FAM™ dye-based assay is used to detect test target loci and the VIC® dye-based assay is used for the reference locus RNase P (PN 4316844 from Applied Biosystems) in assay format 1. Each assay uses 10 ng gDNA, 1× TaqMan® probe/primer mix (900 nM of each primer, 250 nM of each probe) in 1× TaqMan® Genotyping Master Mix in a 10 µl reaction (run in quadruplicate). PCR reactions are incubated in an Applied Biosystems 7900HT SDS instrument for 10 minutes at 95° C., followed by 40 cycles of 15 seconds at 95° C. and 60 seconds at 60° C. Real-time data is collected by the SDS 2.3 software. The relative quantification analysis is performed as described herein above to calculate estimated copy number of each sample for the gene of interest by CopyCaller™ software.

Identification of abnormal chromosomal copy number and karyotype of chromosome 13 indicates the presence or susceptibility to the breast or ovarian cancer associated with chromosome 13.

While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A method for determining the copy number of at least one test locus on at least one chromosome in a test sample, the method comprising:
   interrogating at least one test locus on at least one chromosome in the test sample with at least one primer and at least one probe, wherein the interrogating includes quantifying the copy number of at least one test locus, and wherein the at least one test locus is located on a region of the chromosome that is not within a copy number variable region (CNVR) on the chromosome; and
   determining the copy number of at least one chromosome in the test sample on which at least one of the interrogated test loci is located.

2. The method of claim 1, wherein the determining of the copy number of at least one chromosome in the test sample comprises determining the copy number of more than one chromosome in the test sample.

3. The method of claim 1, wherein the copy number of more than one test loci in the test sample is quantified.

4. The method of claim 1, further comprising quantifying the copy number of the interrogated test locus relative to the copy number of at least one of the reference loci of the calibrator sample, wherein the calibrator sample is a virtual calibrator sample derived by a method comprising the steps of:
   (a) interrogating one or more test loci in each test sample using one or more copy number assays and calculating an average $C_T$ for each of said copy number assays;
   (b) interrogating one or more reference loci in each test sample using one or more copy number reference assays and calculating an average $C_T$ from each of said copy number reference assays;
   (c) averaging the copy number assay average $C_T$ values of (a);
   (d) averaging the copy number reference assay average $C_T$ values of (b);
   (e) calculating the relative quantity using values of (c) and (d); and
   (f) determining the copy number for each test locus by multiplying the relative quantity by the copy number of the calibrator sample.

5. The method of claim 1, wherein the test sample comprises genomic DNA.

6. The method of claim 1, wherein at least one of the interrogated test loci and at least one of the reference loci correspond to the same location on a chromosome.

7. The method of claim 1, wherein at least one of the interrogated test loci and at least one of the reference loci correspond to different locations on the chromosome.

8. The method of claim 1, further comprising the steps of:
   (a) amplifying from a first genomic DNA sample at least one or more test loci from at least one chromosome and at least one or more reference loci from at least one chromosome;
   (b) amplifying from a second test genomic DNA sample at least one or more target loci from at least one chromosome and at least one or more reference loci from at least one chromosome;
   (c) calculating the average $C_T$ values for each of amplifications (a) and (b);
   (d) calculating the average of the average $C_T$ values for each of amplifications (a) and (b); and
   (e) calculating the relative copy number from the calculations in (d),
   wherein the one or more test loci from (a) and (b) are located on a region of the chromosome that is not within a copy number variable region on the chromosome.

9. The method of claim 1, further comprising the steps of:
   (a) amplifying from a first genomic DNA sample one or more target loci on a chromosome;
   (b) amplifying from a second genomic DNA sample one or more target loci on a chromosome;
   (c) amplifying from the genomic DNA sample one or more reference loci on a chromosome that is different from the target loci in (a) and (b);
   (d) calculating the average $C_T$ values for each of amplifications (a), (b), and (c);
   (e) calculating the average of the average $C_T$ values for each of amplifications (a), (b), and (c);
   (f) calculating the $\Delta C_T$ value from the average calculated in (e) for amplifications (a) and (c);
   (g) calculating the relative copy number from the calculations in (f) in the genomic DNA sample,
   wherein the target loci are located on a region of the chromosome that is not within a copy number variable region on the chromosome.

10. The method of claim 1, further comprising the steps of:
(a) amplifying from a genomic DNA sample one or more test loci on a chromosome;
(b) performing a second amplification from the genomic DNA sample one or more test loci on a chromosome;
(c) calculating the average $C_T$ values for each of amplifications (a) and (b);
(d) calculating the average of the average $C_T$ values for each of amplifications (a) and (b);
(e) calculating the $\Delta C_T$ value by subtracting the average calculated in (d) for amplification (b) from the average calculated in (d) for amplification (a); and
(f) calculating the relative copy number from the calculations in (e) in the genomic DNA sample,
wherein the target loci are located on a region of the chromosome that is not within a copy number variable region on the chromosome.

11. The method of claim 1, wherein the at least one test locus is amplified using the polymerase chain reaction to produce amplicons.

12. The method of claim 11, wherein the amplification efficiency of each amplicon amplified from the test genome is within about ten percent of any other amplicon.

13. The method of claim 12, wherein at least two target loci are amplified from each arm of each chromosome being interrogated.

14. The method of claim 13, wherein at least four target loci are amplified from each chromosome being assayed.

15. The method of claim 11, wherein multiple target loci are amplified and each is from any other target loci on the arm by approximately the same number of nucleotides.

16. The method of claim 11, wherein the amplicons are less than or equal to about 110 nucleotides in length.

17. The method of claim 16, wherein the amplicons are about 70 to 110 nucleotides in length.

18. The method of claim 11, wherein primers utilized in the polymerase chain reaction are specific for regions outside of a copy number variable region.

19. A method for determining the copy number of at least one test locus on at least one chromosome in a test sample, the method comprising: interrogating at least one test locus on at least one chromosome in the test sample with at least one primer and at least one probe; wherein the interrogating includes quantifying the copy number of at least one test locus, and wherein the at least one test locus is located on a region of the chromosome that is not within a copy number variable region (CNVR) on the chromosome, wherein primers utilized in the polymerase chain reaction are specific for regions outside of a copy number variable region and wherein the primers are selected from the group consisting of SEQ ID NOS. 1-192.

20. The method of claim 19, further comprising diagnosing a disease resulting from a chromosomal abnormality based on the copy number of the at least on test locus.

21. The method of claim 2, further comprising diagnosing a disease resulting from a chromosomal abnormality based on the copy number of the at least one test locus.

* * * * *